United States Patent
Goodman et al.

(10) Patent No.: US 11,746,136 B2
(45) Date of Patent: Sep. 5, 2023

(54) COMPOSITION AND METHODS FOR DISRUPTION OF BACTERIAL BIOFILMS WITHOUT ACCOMPANYING INFLAMMATION

(71) Applicant: Research Institute at Nationwide Children's Hospital, Columbus, OH (US)

(72) Inventors: Steven David Goodman, Hilliard, OH (US); Lauren O. Bakaletz, Hilliard, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 137 days.

(21) Appl. No.: 16/492,582

(22) PCT Filed: Mar. 14, 2018

(86) PCT No.: PCT/US2018/022508
§ 371 (c)(1),
(2) Date: Sep. 9, 2019

(87) PCT Pub. No.: WO2018/170178
PCT Pub. Date: Sep. 20, 2018

(65) Prior Publication Data
US 2021/0139551 A1    May 13, 2021

Related U.S. Application Data

(60) Provisional application No. 62/471,834, filed on Mar. 15, 2017.

(51) Int. Cl.
| | | |
|---|---|---|
| *C07K 14/52* | (2006.01) | |
| *A61P 31/04* | (2006.01) | |
| *A01N 63/50* | (2020.01) | |
| *A61K 38/19* | (2006.01) | |
| *A61K 45/06* | (2006.01) | |

(52) U.S. Cl.
CPC .............. *C07K 14/52* (2013.01); *A01N 63/50* (2020.01); *A61K 38/19* (2013.01); *A61K 45/06* (2013.01); *A61P 31/04* (2018.01)

(58) Field of Classification Search
None
See application file for complete search history.

(56) References Cited

U.S. PATENT DOCUMENTS

| | | |
|---|---|---|
| 8,933,029 B2 | 1/2015 | McNicol et al. |
| 8,999,291 B2 | 4/2015 | Goodman et al. |
| 9,017,656 B2 | 4/2015 | Hancock et al. |
| 9,155,792 B2 | 10/2015 | Cottarel et al. |
| 9,745,366 B2 | 8/2017 | Goodman et al. |
| 10,595,530 B2 | 3/2020 | Goodman et al. |
| 2002/0132753 A1 | 9/2002 | Rosen et al. |
| 2003/0060410 A1 | 3/2003 | Tracey et al. |
| 2003/0099602 A1 | 5/2003 | Levin et al. |
| 2003/0229065 A1 | 12/2003 | Levy et al. |
| 2004/0202670 A1 | 10/2004 | Apicella |
| 2005/0131222 A1 | 6/2005 | Fleischmann et al. |
| 2005/0221439 A1 | 10/2005 | Bakaletz et al. |
| 2006/0030539 A1 | 2/2006 | Nick et al. |
| 2006/0099207 A1 | 5/2006 | Wu et al. |
| 2006/0121047 A1 | 6/2006 | Tracey |
| 2006/0228384 A1 | 10/2006 | Eldridge |
| 2007/0154529 A1 | 7/2007 | Bullerdiek |
| 2007/0264256 A1 | 11/2007 | Bakaletz et al. |
| 2009/0029929 A1 | 1/2009 | Nakajima et al. |
| 2010/0291177 A1 | 11/2010 | Hermans et al. |
| 2011/0236306 A1 | 9/2011 | Goodman et al. |
| 2012/0128701 A1 | 5/2012 | Goodman et al. |
| 2015/0086542 A1 | 3/2015 | Goodman et al. |
| 2015/0166641 A1 | 6/2015 | Goodman et al. |
| 2016/0095316 A1 | 4/2016 | Goodman et al. |
| 2016/0175440 A1 | 6/2016 | Goodman et al. |
| 2021/0139610 A1 | 5/2021 | Goodman et al. |
| 2021/0340198 A1 | 11/2021 | Goodman et al. |

FOREIGN PATENT DOCUMENTS

| | | |
|---|---|---|
| JP | 2006-506441 A | 2/2006 |
| JP | 2006-506467 | 2/2006 |
| JP | 2008-520552 | 6/2008 |
| WO | WO-00/47104 A2 | 8/2000 |
| WO | WO-03/026691 A1 | 4/2003 |
| WO | WO-03/026691 A2 | 4/2003 |

(Continued)

OTHER PUBLICATIONS

Park and Littman "Redox State-Dependent Interaction of HMGB1 and Cisplatin-Modified DNA" Biochemistry 50:2567-2574. (Year: 2011).*

U.S. Appl. No. 17/150,731, filed Jan. 15, 2021, The Research Institute at Nationwide Children's Hospital.

Andersson, U. et al. (2011) "HMGB1 Is a Therapeutic Target for Sterile Inflammation and Infection," Annu. Rev. Immunol. 29:139-162.

(Continued)

*Primary Examiner* — Sudhakar Katakam
*Assistant Examiner* — Zachary J Miknis
(74) *Attorney, Agent, or Firm* — Foley & Lardner LLP

(57) ABSTRACT

Methods of breaking down a biofilm or inhibiting, preventing or treating a microbial infection that produces a biofilm are disclosed, which involves administration of a polypeptide that has one or more modified HMG-box 1 domains to a subject suffering from the infection or having the biofilm. By competing with microbial proteins that bind to DNA scaffold in the biofilm, these polypeptides destabilize the biofilm leading to destruction and removal of the biofilm by the immune system.

6 Claims, 9 Drawing Sheets
Specification includes a Sequence Listing.

(56) References Cited

FOREIGN PATENT DOCUMENTS

| | | | |
|---|---|---|---|
| WO | WO-2004/014418 A2 | 2/2004 | |
| WO | WO-2004/046345 A2 | 6/2004 | |
| WO | WO-2004/072094 A2 | 8/2004 | |
| WO | WO-2005/025604 A2 | 3/2005 | |
| WO | WO-2005/111066 A2 | 11/2005 | |
| WO | WO-2006/017816 A2 | 2/2006 | |
| WO | WO-2006/083301 A2 | 8/2006 | |
| WO | WO-2006/114805 A2 | 11/2006 | |
| WO | WO-2007/001422 A2 | 1/2007 | |
| WO | WO 2012/034090 A1 | 3/2012 | |
| WO | WO-2012034090 A1 * | 3/2012 | ............. A61P 37/04 |
| WO | WO 2014/016417 A1 | 1/2014 | |
| WO | WO-2014016417 A1 * | 1/2014 | ............. A61P 21/00 |
| WO | WO 2016/184795 A1 | 11/2016 | |

OTHER PUBLICATIONS

Barve et al., "Cloning and characterization of the mating type (MAT) locus from Ascochyta rabiei (teleomorph: *Didymella rabiei*) and a MAT phylogeny of legume-associated *Ascochyta* spp.," Fungal Genetics and Biology, vol. 39, No. 2, Feb. 10, 2003, pp. 151-167.

Brandstetter et al., "Antibodies Directed Against Integration Host Factor Mediate Biofilm Clearance From Nasopore," The Laryngoscope, vol. 12, No. 11, Nov. 2013, pp. 2626-2632.

Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258, Supplementary Material, 6 pages.

Cho et al., "The modulation of the biological activities of mitochondrial histone Abf2p by yeast PKA and its possible role in the regulation of mitochondrial DNA content during glucose repression," Biochimica et Biophysica Acta, vol. 1522, No. 3, Oct. 4, 2001, pp. 175-186.

Devaraj et al., "DNABII proteins play a central role in UPEC biofilm structure", Molecular Microbiology, 2015, vol. 96, vol. 6, Jun. 2015, pp. 1119-1135.

E. Melloni, et al, "Extracellular release of the 'differentiation enhancing factor', a HMG 1 protein type, is an early step in murine erythroleukemia cell differentiation" FEBS Letters 368, Year 1995, pp. 466-470.

Falciola et al., "Mutational analysis of the DNA binding domain A of chromosomal protein HMG1," Nucleic Acids Research, vol. 22, No. 3, Jan. 10, 1994, pp. 285-292.

Goodman et al., "Replacement of Integration Host Factor Protein-induced DNA Bending by Flexible Regions of DNA," The Journal of Biological Chemistry, vol. 274, No. 52, Aug. 6, 1999, pp. 37004-37011.

Granston et al., "Characterization of a Set of Integration Host Factor Mutants Deficient for DNA Binding," J. Mol. Biol., vol. 234, Jun. 21, 1993, pp. 45-59.

Harley et al., "The Molecular Action and Regulation of the Testis-Determining Factors, SRY (Sex-Determining Region on the Y Chromosome) and SOX9 [SRY-Related High-Mobility Group (HMG) Box 9]," Endocrine Reviews, vol. 24, No. 4, Aug. 2003, pp. 466-487.

Hirotaka Kazama, et al., "Immune Tolerance Induction By Apoptotic Cells Requires Caspase-Dependent Oxidation of HMGB1",NIH Public Access, Immunity., Jul. 18, 2008, pp. 1-25.

Jurcisek et al., "Biofilms Formed by Nontypeable Haemophilus influenzae In Vivo Contain both Double-Stranded DNA and Type IV Pilin Protein," Journal of Bacteriology, vol. 189, No. 10, Feb. 15, 2007, pp. 3868-3875.

Kamashev et al., "The histone-like protein HU binds specifically to DNA recombination and repair intermediates," The EMBO Journal, vol. 19, No. 23, Oct. 13, 2000, pp. 6527-6535.

Kornblit et al., "The genetic variation of the human HMG1 gene," Tissue Antigens, vol. 70, Apr. 12, 2007, pp. 151-156.

Labbé et al., "Association of Smads with lymphoid enhancer binding factor 1/T cell-specific factor mediates cooperative signaling by the transforming growth factor-β and Wnt pathways," Proc. Natl. Acad. Sci. USA, vol. 97, No. 15, Jul. 18, 2000, pp. 8358-8363.

Lee, H. et al. (2010) Analysis of nuclear high mobility group box I (HMGBI)-binding proteins in colon cancer cells: clustering with proteins involved in secretion and extranuclear function. J Proteome Res 9: 4661-70.

Mo Freire, et al., "A Bacterial Biofilm Induced Oral Osteolytic Infection Can be Successfully Treated by Immuno-Targeting an Extracellular Nucleoid Associated Protein", Mol Oral Microbiol. Feb. 2017, p. 1-21.

Novotny, L.A., Clements, J.D., and Bakaletz, L.O. "Kinetic analysis and evaluation of the mechanisms involved in the resolution of experimental nontypeable Haemophilus influenzae-induced otitis media after transcutaneous immunization", Vaccine 31, Jul. 25, 2013, pp. 3417-3426.

Novotny, L.A., et al., "Transcutaneous immunization as preventative and therapeutic regimens to protect against experimental otitis media due to nontypeable Haemophilus influenzae", Mucosal Immunol vol. 5 No. 1, Jul. 2011, pp. 456-467.

Orlova, V.V. et al., "A novel pathway of HMGB1-mediated inflammatory cell recruitment that requires Mac-1-integrin", EMBO J, vol. 26, No. 4, Year 2007, pp. 1129-1139.

Paull, T.T., Haykinson, M.J., and Johnson, R.C., "The nonspecific DNA-binding and -bending proteins HMG1 and HMG2 promote the assembly of complex nucleoprotein structures", Genes Dev 7, Year 1993, pp. 1521-1534.

Penzo, M. et al., "Inhibitor of NF-kappa B kinases alpha and beta are both essential for high mobility group box 1-mediated chemotaxis", J Immunol 184, Apr. 15, 2010, pp. 4497-4509.

Pistoia, V. and Raffaghello, L., "Damage-associated molecular patterns (DAMPs) and mesenchymal stem cells: a matter of attraction and excitement", Eur J Immunol 41, Year 2011, pp. 1828-1831.

Ranzato, E., Patrone, M., Pedrazzi, M., and Burlando, B. (2009) HMGb1 promotes scratch wound closure of HaCaT keratinocytes via ERKI/2 activation. Mal Cell Biochem 332: 199-205.

Rui Kang, etal, "HMGB1 in Health and Disease", Mol Aspects Med., Dec. 2014, pp. 1-226.

Stefania Mardente, et al., "HMGB1 induces the overexpression of miR-222 and miR-221 and increases growth and motility in papillary thyroid cancer cells", Oncology Reports, vol. 28, Jul. 9, 2012, pp. 2285-2289.

Swinger et al., "IHF and HU: flexible architects of bent DNA," Current Opinion in Structural Biology, vol. 14, No. 1,2004, pp. 28-35.

Tang et al., "High Mobility Group Box 1 (HMGB1) Activates an Autophagic Response to Oxidative Stress", Antioxidants & Redox Signaling, vol. 15, No. 8, Oct. 15, 2011 (accepted Mar. 10, 2011), pp. 2185-2195.

Wang, H. et al. (1999) HMG-1 as a late mediator of endotoxin lethality in mice. Science 285, pp. 248-251.

Wei Gong, et al, "Amino acid residues 201-205 in C-terminal acidic tail region plays a crucial role in antibacterial activity of HMGB1", Journal of Biomedical Science, Sep. 14, 2009, pp. 1-10.

Yang, D., Chen, Q., Yang, H., Tracey, K.J., Bustin, M., and Oppenheim, J.J., "High mobility group box-1 protein induces the migration and activation of human dendritic cells and acts as an alarmin", J Leukoc Biol 81, Jan. 2007, pp. 59-66.

Yang, H. et al., "Redox modification of cysteine residues regulates the cytokine activity of high mobility group box-1 (HMGB1)", Mol Med 18, Year 2012, pp. 250-259.

Zetterstrom, C.K., Strand, M.L., and Soder, O., "The high mobility group box chromosomal protein 1 is expressed in the human and rat testis where it may function as an antibacterial factor", Hum Reprod 21, Year 2006, pp. 2801-2809.

International Search Report and Written Opinion issued in PCT Application No. PCT/US2018/022508 dated Jul. 18, 2018, 17 pages.

Andersson et al., "HMGB1 Is a Therapeutic Target for Sterile Inflammation and Infection", Annual Review of Immunology, vol. 29, No. 1, Jan. 1, 2011, pp. 139-162.

(56) References Cited

OTHER PUBLICATIONS

Andersson et al., "High Mobility Group 1 Protein (HMG-1) Stimulates Proinflammatory Cytokine Synthesis in Human Monocytes", The Journal of Experimental Medicine, vol. 192, No. 4, Aug. 21, 2000, pp. 565-570.
Goodman et al., "Biofilms can be dispersed by focusing the immune system on a common family of bacterial nucleoid-associated proteins", Advances in Mucosal Immunology, Jun. 29, 2011, pp. 1-13.
Estrela et al., "Combining Biofilm-Controlling Compounds and Antibiotics as a Promising New Way to Control Biofilm Infections", Pharmaceuticals, vol. 3, No. 5, May 1, 2010, pp. 1374-1393.
DATABASE Geneseq [Online] "Human high mobility group box-ABB (HMG-AB) protein, SEQ ID 29", Databased accession No. AGB07712, Jul. 26, 2007.
Novotny, et al., "Monoclonal antibodies against DNA-binding tips of DNABII proteins disrupt biofilms in vitro and induce bacterial clearance in vivo", EBioMedicine 10 (2016), pp. 33-44.
U.S. Appl. No. 15/999,215, filed Aug. 16, 2018, Goodman et al.
U.S. Appl. No. 16/297,094, filed Mar. 8, 2019, Goodman et al.
U.S. Appl. No. 16/475,654, filed Jul. 2, 2019, Bakaletz et al.
U.S. Appl. No. 16/475,656, filed Jul. 2, 2019, Bakaletz et al.
Bass, J.I.F et al. (2010) "Extracellular DNA: A Major Proinflammatory Component of Pseudomonas aeruginosa Biofilms," The Journal of Immunology 184:6386-6395.
Beech, I.B. et al. (2005) "Microbe-surface interactions in biofouling and biocorrosion processes," International Microbiology 8:157-168.
Brady, R.A. et al. (2006) "Identification of *Staphylococcus aureus* Proteins Recognized by the Antibody-Mediated Immune Response to a Biofilm Infection," Infection and Immunity 74(6):3415-3426.
Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258.
Catlin, "Extracellular Deoxyribonucleic Acid of Bacteria and a Deoxyribonuclease Inhibitor," Science, vol. 124, Sep. 7, 1956, pp. 441-442.
Ceri, H. et al. (1999) "The Calgary Biofilm Device: New Technology for Rapid Determination of Antibiotic Susceptibilities of Bacterial Biofilms," Journal of Clinical Microbiology 37(6):1771-1776.
Chen, C. et al. (2004) "Substrate specificity of Helicobacter pylori histone-like HU protein is determined by insufficient stabilization of DNA flexure points," Biochem J. 383:343-351.
Coenye, T. et al. (2010) "In vitro and in vivo model systems to study microbial biofilm formation," Journal of Microbiological Methods 83:89-105.
Collarini, E.J. et al. (2009) "Potent High-Affinity Antibodies for Treatment and Prophylaxis of Respiratory Syncytial Virus Derived from B Cells of Infected Patients," J Immunol 183:6338-6345.
Dalai, B. et al. (2009) "Histone-like protein H-NS regulates biofilm formation and virulence of Actinobacillus pheuropneumonia," Microbial Pathogenesis 46:128-134.
Darouiche, R.O. et al. (2004) "Treatment of Infections Associated with Surgical Implants," N Engl J Med 350:1422-1429.
Donlan, R.M. et al. (2002) "Biofilms: Survival Mechanisms of Clinically Relevant Microorganisms," Clinical Microbiology Reviews 15(2):167-193.
Durocher et al., "High-level and high-throughput recombinant protein production by transient transfection of suspension-growing human 293-EBNA1 cells," Nucleic Acids Research, vol. 30, No. 2, e9, Nov. 11, 2001, 9 pages.
Eboigbodin, K.E. et al. (2008) "Characterization of the Extracellular Plymeric Substances Produced by *Escherichia coli* Using Infrared Spectroscopic, Proteomic, and Aggregation Studies," Biomacromolecules 9:686-695.
Estrela et al., "Combining Biofilm-Controlling Compounds and Antibiotics as a Promising New Way to Control Biofilm Infections," Pharmaceuticals, vol. 3, May 11, 2010, pp. 1374-1393.
Fan, Z. et al. (2002) "HMG2 Interacts with the Nucleosome Assembly Protein SET and Is a Target of the Cytotoxic T-Lymphocyte Protease Granzyme A," Molecular and Cellular Biology 22(8):2810-2820.
Garcia-Contreras et al., "Protein Translation and Cell Death: The Role of Rare tRNAs in Biofilm Formation and in Activating Dormant Phage Killer Genes," PLoS ONE, vol. 3, No. 6, Jun. 11, 2008, e2394, 17 pages.
George et al., "Cystic fibrosis infections: treatment strategies and prospects," FEMS Microbiol Lett., vol. 300, Jun. 15, 2009, pp. 153-164.
Good et al., "Synthetic RNA silencing in bacteria—antimicrobial discovery and resistance breaking," Frontiers in Microbiology, vol. 2, No. 185, Sep. 12, 2011, pp. 1-11.
Goodman et al., "Biofilms can be dispersed by focusing the immune system on a common family of bacterial nucleoid-associated proteins," Mucosal Immunology, vol. 4, No. 6, Nov. 2011, pp. 625-637.
Goodman et al., "In Vitro Selection of Integration Host Factor Binding Sites," Journal of Bacteriology, vol. 181, No. 10, May 1999, pp. 3246-3255.
Govan et al., "Microbial pathogenesis in cystic fibrosis: mucoid Pseudomonas aeruginosa and Burkholderia cepacia," Microbiol. Rev., vol. 60, No. 3, Sep. 1996, pp. 539-574.
Gustave et al., "Targeting bacterial integration host factor to disrupt biofilms associated with cystic fibrosis," Journal of Cystic Fibrosis, vol. 12, No. 4, Nov. 17, 2012, pp. 384-389.
Hall-Stoodley et al., "Bacterial Biofilms: From the Natural Environment to Infectious Diseases," Nature Reviews, Microbiology, vol. 2, Feb. 2004, pp. 95-108.
Harriman, W.D. et al. (2008) "Antibody discovery via multiplexed single cell characterization," Journal of Immunological Methods 341:135-145.
Harrison, J.J. et al. (2010) "Microtiter susceptibility testing of microbes growing on peg lids: a miniaturized biofilm model for high-throughput screening," Nature Protocols 5(7):1236-1254.
Haruta et al.,"Long-term bacterial exposure can trigger nonsuppurative destructive cholangitis associated with multifocal epithelial inflammation," Laboratory Investigation, vol. 90, Apr. 2010, pp. 577-588.
Hoyle et al., "Bacterial Resistance to Antibiotics: The Role of Biofilms," Prog. Drug Res., vol. 37, 1991, pp. 91-105.
Janeway, "Manipulating the immune response to fight infection," Immunobiology: The Immune System in Health and Disease, 5th ed.; retrieved online from https://www.ncbi.nlm.nih.gov/books/NBK27131/, 2001, 13 pages.
Johnson et al., "Chapter 8: Bending and Compaction of DNA by Proteins," Protein-Nucleic Acid Interactions: Structural Biology, 2008, pp. 176-220.
Jurcisek et al., "Role of Sialic Acid and Complex Carbohydrate Biosynthesis in Biofilm Formation by Nontypeable Haemophilus influenzae in the Chinchilla Middle Ear," Infection and Immunity, vol. 73, Jun. 2005, pp. 3210-3218.
Khrapunov, S. et al. (2006) "Binding then bending: A mechanism for wrapping DNA," PNAS 103(51):19217-19218.
Kim et al., "Proteins Released by Helicobacter pylori In Vitro," Journal of Bacteriology, vol. 184, No. 22, Nov. 2002, pp. 6155-6162.
Kirketerp-Moller et al., "Distribution, Organization, and Ecology of Bacteria in Chronic Wounds," Journal of Clinical Microbiology, vol. 46, No. 8, Aug. 2008, pp. 2717-2722.
Kristian, S.A. et al. (2003) "Alanylation of Teichoic Acids Protects *Staphylococcus aureus* against Toll-like Receptor 2-Dependent Host Defense in a Mouse Tissue Cage Infection Model," The Journal of Infectoius Diseases 188:414-423.
Kyd et al., "Efficacy of the 26-Kilodalton Outer Membrane Protein and Two P5 Fimbrin-Derived Immunogens To Induce Clearance of Nontypeable Haemophilus influenzae from the Rat Middle Ear and Lungs as Well as from the Chinchilla Middle Ear and Nasopharynx," Infection and Immunity, vol. 71, No. 8, Aug. 2003, pp. 4691-4699.
Lebeaux et al., "From in vitro to in vivo Models of Bacterial Biofilm-Related Infections," Pathogens, vol. 2, May 13, 2013, pp. 288-356.

(56) References Cited

OTHER PUBLICATIONS

Li et al., "Retroviral eDNA Integration: Stimulation by Hmg I Family Proteins," Journal of Virology, vol. 74, No. 23, Dec. 2000, pp. 10965-10974.
Liu et al., "The essentiality and involvement of *Streptococcus intermedius* histone-like DNA-binding protein in bacterial viability and normal growth," Molecular Microbiology, vol. 68, No. 5, Apr. 21, 2008, pp. 1268-1282.
Liu, D. et al. (2008) "Histone-like DNA binding protein of *Streptococcus intermedius* induces the expression of pro-inflammatory cytokines in human monocytes via activation of ERK1/2 and JNK pathways," Cellular Microbiology 10(1):262-276.
Lunsford et al., "DNA-Binding Activities in *Streptococcus gordonii*: Indentification of a Receptor-Nickase and a Histonelike Protein," Current Microbiology, vol. 32, 1996, pp. 95-100.
Lutz, H.U. et al. (1990) "Covalent binding of detergent-solubilized membrane glycoproteins to 'Chemobond' plates for ELISA," Journal of Immunological Methods 129:211-220.
M. Elizabeth Brockson et al., "Evaluation of the kinetics and mechanism of action anti-integration host factor-mediated disruption of bacterial biofilms: Anti-IHF-mediated biofilm collapse", Molecular Microbiology., Aug. 19, 2014,pp. 1-22.
Mann, E.E. et al. (2009) "Modulation of eDNA Release and Degradation Affects *Staphylococcus aureus* Biofilm Maturation," PLoS ONE 4(6):e5822, 1-12.
MOUW et al., "Shaping the Borrelia burgdorferi genome: crystal structure and binding properties of the DNA-bending protein Hbb," Molecular Microbiology, vol. 63, No. 5, Jan. 22, 2007, pp. 1319-1330.
Mukherjee et al., "Quantitative protein expression and cell surface characteristics of *Escherichia coli* MG1655 biofilms," Proteomics, vol. 11, Nov. 1, 2010, pp. 339-351.
Murphy, T.F. et al. (2002) "Biofilm formation by nontypeable Haemophilus influenzae: strain variablitiy, outer membrane antigen expression and role of pili," BMC Microbiology 2:7, 1-8.
Nakamura et al., "HMG Box A in HMG3 Protein Functions as a Mediator of DNA Structural Alteration Together with BoxB," J. Biochem., vol. 129, No. 4, Feb. 5, 2001, pp. 643-651.
Nash et al., "Overproduction of *Escherichia coli* Integration Host Factor, a Protein with Nonidentical Subunits," Journal of Bacteriology, vol. 169, No. 9, Sep. 1987, pp. 4124-4127.
NCBI Genebank: P0A6Y1 (Sep. 13, 2005), 7 pages.
Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, pp. 279-289 (Dec. 10, 2009).
Novotny et al., "Structural Stability of Burkholderia cenocepacia Biofilms Is Reliant on eDNA Structure and Presence of a Bacterial Nucleic Acid Binding Protein," PLOS ONE, vol. 8, No. 6, e67629, Jun. 2013, 15 pages.
Novotny et al., "Detection and characterization of pediatric serum antibody to the OMP PS-homologous adhesin of nontypeable Haemophilus influenzae during acute otitis media," Vaccine, vol. 20, No. 29-30, Jun. 8, 2002, pp. 3590-3597.
Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, Aug. 22, 2009, pp. 279-289.
Novotny et al., "Epitope mapping of the Outer Membrane Protein P5-Homologous Fimbrin Adhesin of Nontypeable Haemophilus influenzae," Infection and Immunity, vol. 68, No. 4, Apr. 2000, pp. 2119-2128.
Novotny et al., "Passive immunization with human anti-protein D antibodies induced by polysaccharide protein D conjugates protects chinchillas against otitis media after intranasal challenge with Haemophilus influenzae," Vaccine, vol. 24, No. 22, Mar. 27, 2006, pp. 4804-4811.
Novotny et al., "The Fourth Surface-Exposed Region of the Outer Membrane Protein P5-Homologous Adhesin of the Nontypable Haemophilus influenzae Is an Immunodominant But Nonprotective Decoying Epitope," The Journal of Immunology, vol. 171, No. 4, Jun. 10, 2003, pp. 1978-1983.
Oberto et al., "Histones, HMG, HU, IHF: Même combat," Biochimie, vol. 76, 1994, pp. 901-908.
PDB ID: 1IHF: Rice, P.A. et al. (1996), 1 page; retrieved online from http://www.rcsb.org/pdb/explore.do?structureId=IHF, 2 pages.
Pedulla et al., "A novel host factor for integration of mycobacteriophage L5," Proc. Natl. Acad. Sci. USA, vol. 93, Dec. 1996, pp. 15411-15416.
Percival, S.L. et al. (2015) "Biofilms and Wounds: An Overview of the Evidence," Advances in Wound Care4(7):373-381.
Petersen et al., "Biofilm Mode of Growth of *Streptococcus intermedius* Favoreed by a Competence-Stimulating Signaling Peptide," Journal of Bacteriology, vol. 186, No. 18, Sep. 2004, pp. 6327-6331.
Pethe et al., "Mycobacterium smegmatis laminin-binding glycoprotein shares epitopes with Mycobacterium tuberculosis heparin-binding haemagglutinin," Molecular Microbiology, vol. 39, No. 1, 2001, pp. 89-99.
Rice et al., "Crystal Structure of an IHF-DNA Complex: A Protein-Induced DNA U-Turn," Cell, vol. 87, No. 7, pp. 1295-1306 (Dec. 27, 1996).
Rice et al., "Crystal Structure of an IHF-DNA Complex: A Protein-Induced DNA U-Turn," Cell, vol. 87, No. 7, Dec. 27, 1996, pp. 1295-1306.
Sapi et al., "Characterization of Biofilm Formation by Borrelia burgdorferi In Vitro," PLOS One, vol. 7, No. 10, Oct. 2012, pp. 1-11.
Segall et al., "Architectural elements in nucleoprotein complexes: interchangeability of specific and non-specific DNA binding proteins," The EMBO Journal, vol. 13, No. 19, 1994, pp. 4536-4548.
Shahrooei et al., "Inhibition of *Staphylococcus epidermidis* Biofilm Formation by Rabbit Polyclonal Antibodies against the SesC Protein," Infection and Immunity, vol. 77, No. 9, Sep. 2009, pp. 3670-3678.
Singh et al.."Quorum-sensing signals indicate that cystic fibrosis lungs are infected with bacterial biofilms," Nature, vol. 407, No. 12, Oct. 12, 2000, pp. 762-764.
Smith et al., "Cystic Fibrosis Airway Epithelia Fail to Kill Bacteria Because of Abnormal Airway Surface Fluid," Cell, vol. 85, Apr. 19, 1996, pp. 229-236.
Stros et al., "The HMG-box: a versatile protein domain occurring in a wide variety of DNA-binding proteins," Cell. Mol. Life Sci., vol. 64, No. 19-20, Jun. 29, 2007, pp. 2590-2606.
Sun et al.,"Inhibition of Biofilm Formation by Monoclonal Antibodies against *Staphylococcus epidermindis* RP62A Accumulation-Associated Protein," Clinical & Diagnostic Laboratory Immunology, vol. 12, No. 1, Jan. 2005, pp. 93-100.
Takeda, "Polyhistidine Affinity Chromatography for Purification and Biochemical Analysis of Fungal Cell Wall-Degrading Enzymes," Affinity Chromatography, Dr. Sameh Magdeldin (Ed.), ISBN: 978-953-51-0325-7, In Tech, 2012, pp. 177-186.
Taudte et al., "Alanine mutagenesis of high-mobility-group-protein-1 box B (HMG1-B)," Biochem. J., vol. 347, Feb. 25, 2000, pp. 807-814.
Teter et al., "DNA Bending and Twisting Properties of Integration Host Factor Determined by DNA Cyclization," Plasmid, vol. 43, 2000, pp. 73-84.
Thomas, "HMG1 and 2: architectural DNA-binding proteins," Biochemical Society Transactions, vol. 29, Pt. 4, Apr. 12, 2001, pp. 395-401.
Van Schaik et al., "DNA Binding: a Novel Function of Pseudomonas aeruginosa Type IV Pili," Journal of Bacteriology, vol. 187, No. 4, Feb. 2005, pp. 1455-1464.
Whitchurch et al., "Extracellular DNA Required for Bacterial Biofilm Formation," Science, vol. 295, No. 5559, Feb. 22, 2002, p. 1487, 1 page.
Whitchurch et al., "Extracellular DNA Required for Bacterial Biofilm Formation," Science, vol. 295, No. 5559, Feb. 22, 2002, Supplementary Material, 2 pages.

(56) References Cited

OTHER PUBLICATIONS

Winters et al., "Isolation and Characterization of a *Streptococcus pyogenes* Protein that Binds to Basal Laminae of Human Cardiac Muscle," Infection and Immunity, vol. 61, No. 8, Aug. 1993, pp. 3259-3264.
Yoshida, M. (1996) SEIKAGAKU Biochemistry 68(12):1829-1834.
Zimmerli et al., "Pathogenesis of Foreign Body Infection: Description and Characteristics of an Animal Model," The Journal of Infectious Diseases, vol. 146, No. 4, Oct. 1982, pp. 487-497.
Zimmerli, W. et al. (1984) "Pathogenesis of Foreign Body Infection," J. Clin. Invest. 73:1191-1200.
Zulianello et al., "The HimA and HimD subunits of integration host factor can specifically bind to DNA as homodimers," The EMBO Journal, vol. 13, No. 4, Apr. 1, 1994, pp. 1534-1540.

\* cited by examiner

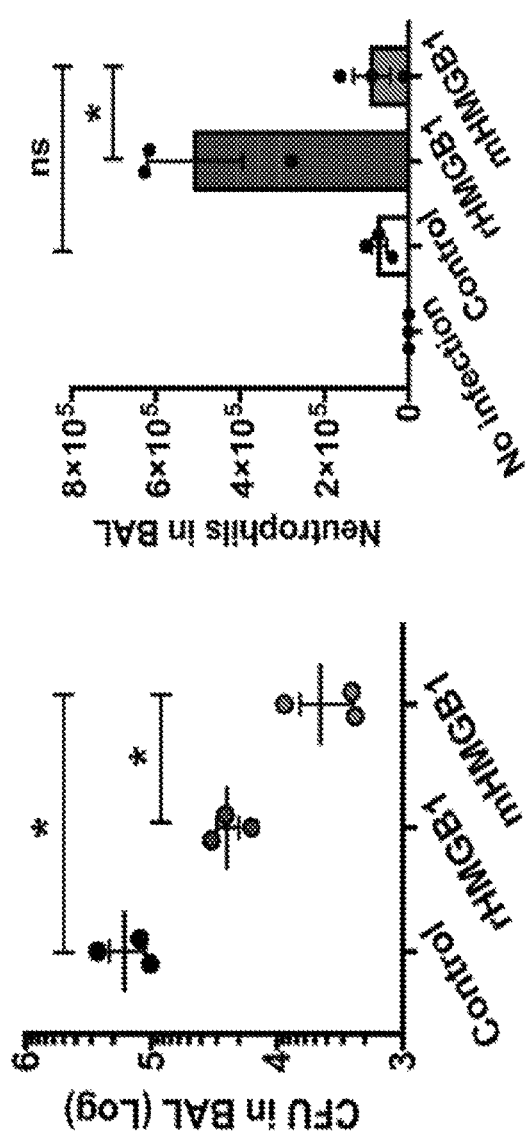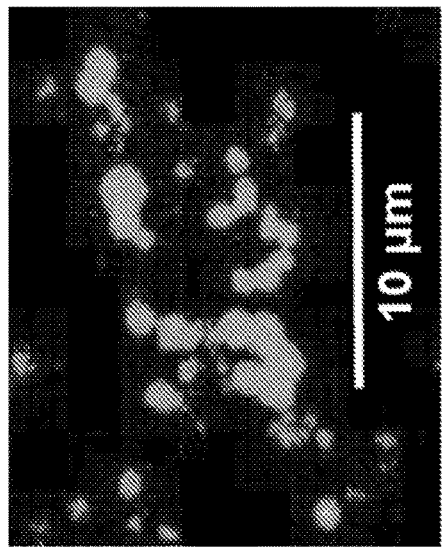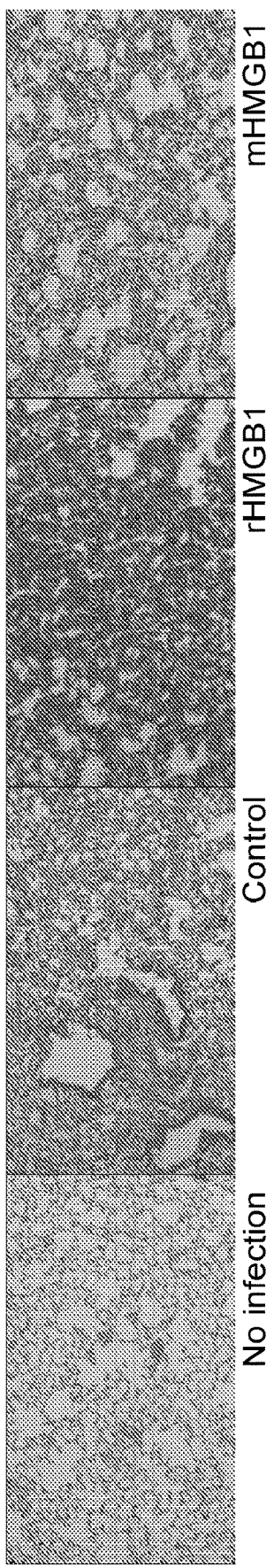
FIG. 7C
FIG. 7B
FIG. 7A
FIG. 7D

SEQUENCE LISTING

```
<160> NUMBER OF SEQ ID NOS: 86

<210> SEQ ID NO 1
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Gly Glu Glu
            180                 185                 190

Asp Glu Glu Asp Glu Glu Glu Glu Asp Glu Glu Glu Glu Asp Glu
        195                 200                 205

Glu Glu Asp Asp Asp Asp Glu
    210                 215
```

<210> SEQ ID NO 2
<211> LENGTH: 215
<212> TYPE: PRT
<213> ORGANISM: Homo sapiens

<400> SEQUENCE: 2

Met Gly Lys Gly Asp Pro Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Gly Glu
            180                 185                 190

Asp Glu Glu Asp Glu Glu Glu Glu Asp Glu Asp Glu Asp Glu
        195                 200                 205

Glu Glu Asp Asp Asp Asp Glu
    210                 215

<210> SEQ ID NO 3
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Gly Lys Gly Asp Pro Lys Pro Arg Gly Lys Met Ser Ser Tyr
1               5                   10                  15

Ala Phe Phe Val Gln Thr Ser Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys

```
                    85                  90                  95
Arg Pro Pro Ser Ala Phe Phe Leu Phe Cys Ser Glu Tyr Arg Pro Lys
            100                 105                 110
Ile Lys Gly Glu His Pro Gly Leu Ser Ile Gly Asp Val Ala Lys Lys
            115                 120                 125
Leu Gly Glu Met Trp Asn Asn Thr Ala Ala Asp Lys Gln Pro Tyr
            130                 135                 140
Glu Lys Lys Ala Ala Lys Leu Lys Glu Lys Tyr Glu Lys Asp Ile Ala
145                 150                 155                 160
Ala Tyr Arg Ala Lys Gly Lys Pro Asp Ala Ala Lys Lys Gly Val Val
                165                 170                 175
Lys Ala Glu Lys Ser Lys Lys Lys Glu Glu Glu Gly Glu Glu
            180                 185                 190
Asp Glu Glu Asp Glu Glu Glu Glu Asp Glu Asp Glu Asp Glu
            195                 200                 205
Glu Glu Asp Asp Asp Asp Glu
            210                 215

<210> SEQ ID NO 4
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Gly Lys Gly Asp Pro Lys Lys Pro Arg Gly Lys Met Ser Ser Tyr
1               5                   10                  15
Ala Phe Phe Val Gln Thr Cys Arg Glu Glu His Lys Lys Lys His Pro
                20                  25                  30
Asp Ala Ser Val Asn Phe Ser Glu Phe Ser Lys Lys Ser Ser Glu Arg
            35                  40                  45
Trp Lys Thr Met Ser Ala Lys Glu Lys Gly Lys Phe Glu Asp Met Ala
50              55                  60
Lys Ala Asp Lys Ala Arg Tyr Glu Arg Glu Met Lys Thr Tyr Ile Pro
65              70                  75                  80
Pro Lys Gly Glu Thr Lys Lys Lys Phe Lys Asp Pro Asn Ala Pro Lys
                85                  90                  95
Arg Pro Pro Ser Ala Phe Phe Leu Phe Cys Ser Glu Tyr Arg Pro Lys
            100                 105                 110
Ile Lys Gly Glu His Pro Gly Leu Ser Ile Gly Asp Val Ala Lys Lys
            115                 120                 125
Leu Gly Glu Met Trp Asn Asn Thr Ala Ala Asp Lys Gln Pro Tyr
            130                 135                 140
Glu Lys Lys Ala Ala Lys Leu Lys Glu Lys Tyr Glu Lys Asp Ile Ala
145                 150                 155                 160
Ala Tyr Arg Ala Lys Gly Lys Pro Asp Ala Ala Lys Lys Gly Val Val
                165                 170                 175
Lys Ala Glu Lys Ser Lys Lys Lys Glu Glu Glu Gly Glu Glu
            180                 185                 190
Asp Glu Glu Asp Glu Glu Glu Glu Asp Glu Asp Glu Asp Glu
            195                 200                 205
Glu Glu Asp Asp Asp Asp Glu
            210                 215
```

<210> SEQ ID NO 5
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Ser Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Gly Glu Glu
            180                 185                 190

Asp Glu Glu Asp Glu Glu Glu Glu Asp Glu Glu Glu Glu Asp Glu Asp
        195                 200                 205

Glu Glu Asp Asp Asp Asp Glu
    210                 215
```

<210> SEQ ID NO 6
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Met Gly Lys Gly Asp Pro Lys Lys Pro Arg Gly Lys Met Ser Ser Tyr
1               5                   10                  15

Ala Phe Phe Val Gln Thr Ser Arg Glu Glu His Lys Lys Lys His Pro
                20                  25                  30

Asp Ala Ser Val Asn Phe Ser Glu Phe Ser Lys Lys Ser Ser Glu Arg
            35                  40                  45

Trp Lys Thr Met Ser Ala Lys Glu Lys Gly Lys Phe Glu Asp Met Ala
50                  55                  60
```

```
Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Gly Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
        210                 215
```

<210> SEQ ID NO 7
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

```
Met Gly Lys Gly Asp Pro Lys Lys Pro Arg Gly Lys Met Ser Ser Tyr
 1               5                  10                  15

Ala Phe Phe Val Gln Thr Ser Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Ser Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Gly Glu Glu
            180                 185                 190

Asp Glu Glu Asp Glu Glu Glu Glu Glu Asp Glu Glu Asp Glu Asp Glu
```

Glu Glu Asp Asp Asp Asp Glu
    210             215

<210> SEQ ID NO 8
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Ser Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Ser Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Gly Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210             215

<210> SEQ ID NO 9
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Gly Lys Gly Asp Pro Lys Lys Pro Arg Gly Lys Met Ser Ser Tyr
1               5                   10                  15

Ala Phe Phe Val Gln Thr Ser Arg Glu Glu His Lys Lys Lys His Pro
            20                  25                  30

Asp Ala Ser Val Asn Phe Ser Glu Phe Ser Lys Lys Ser Ser Glu Arg
        35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
             85                  90                  95

Arg Pro Pro Ser Ala Phe Phe Leu Phe Ser Ser Glu Tyr Arg Pro Lys
             100                 105                 110

Ile Lys Gly Glu His Pro Gly Leu Ser Ile Gly Asp Val Ala Lys Lys
             115                 120                 125

Leu Gly Glu Met Trp Asn Asn Thr Ala Ala Asp Asp Lys Gln Pro Tyr
 130                 135                 140

Glu Lys Lys Ala Ala Lys Leu Lys Glu Lys Tyr Glu Lys Asp Ile Ala
 145                 150                 155                 160

Ala Tyr Arg Ala Lys Gly Lys Pro Asp Ala Ala Lys Lys Gly Val Val
             165                 170                 175

Lys Ala Glu Lys Ser Lys Lys Lys Lys Glu Glu Glu Glu Gly Glu
             180                 185                 190

Asp Glu Glu Asp Glu Glu Glu Glu Asp Glu Glu Asp Glu Asp Glu
             195                 200                 205

Glu Glu Asp Asp Asp Asp Glu
 210                 215

<210> SEQ ID NO 10
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
atgggcaaag gagatcctaa gaagccgaga ggcaaaatgt catcatatgc attttttgtg      60
caaactagtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaggcggaa caaggcccgt tatgaaagag aaatgaaaac ctatatccct     240
cccaaagggg agacaaaaaa gaagttcaag gatcccaatg cacccaagag gcctccttcg     300
gccttcttcc tcttctgctc tgagtatcgc ccaaaaatca aggagaacaa tcctggcctg     360
tccattggtg atgttgcgaa gaaactggga gagatgtgga ataacactgc tgcagatgac     420
aagcagccct tgaaaagaa ggctgcgaag ctgaaggaaa aatacgaaaa ggatattgct     480
gcatatcgag ctaaggaaa gcctgatgca gcaaaaaagg gagttgtcaa ggctgaaaaa     540
agcaagaaaa agaaggaaga ggaggaaggt gaggaagatg aagaggatga ggaggaggag     600
gaagatgaag aagatgaaga tgaagaagaa gatgatgatg atgaa                    645

<210> SEQ ID NO 11
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

```
atgggcaaag gagatcctaa gaagccgaga ggcaaaatgt catcatatgc attttttgtg      60
caaacttgtc gggaggagca taagaagaag cacccagatg cttcagtcaa cttctcagag     120
ttttctaaga agagttcaga gaggtggaag accatgtctg ctaaagagaa aggaaaattt     180
gaagatatgg caaaggcgga caaggcccgt tatgaaagag aaatgaaaac ctatatccct     240
cccaaagggg agacaaaaaa gaagttcaag gatcccaatg cacccaagag gcctccttcg     300
gccttcttcc tcttctgctc tgagtatcgc ccaaaaatca aggagaaca tcctggcctg      360 tccattggtg atgttgcgaa gaaactggga gagatgtgga ataacactgc tgcagatgac     420
aagcagcctt atgaaaagaa ggctgcgaag ctgaaggaaa atacgaaaa ggatattgct      480 gcatatcgag ctaaaggaaa gcctgatgca gcaaaaaagg gagttgtcaa ggctgaaaaa     540
agcaagaaaa agaaggaaga ggaggaaggt gaggaagatg aagaggatga ggaggaggag     600
gaagatgaag aagatgaaga tgaagaagaa gatgatgatg atgaa                     645
```

<210> SEQ ID NO 12
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
atgggcaaag gagatcctaa gaagccgaga ggcaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaaggcgga caaggcccgt tatgaaagag aaatgaaaac ctatatccct     240
cccaaagggg agacaaaaaa gaagttcaag gatcccaatg cacccaagag gcctccttcg     300
gccttcttcc tcttcagctc tgagtatcgc ccaaaaatca aggagaaca tcctggcctg      360 tccattggtg atgttgcgaa gaaactggga gagatgtgga ataacactgc tgcagatgac     420
aagcagcctt atgaaaagaa ggctgcgaag ctgaaggaaa atacgaaaa ggatattgct      480 gcatatcgag ctaaaggaaa gcctgatgca gcaaaaaagg gagttgtcaa ggctgaaaaa     540
agcaagaaaa agaaggaaga ggaggaaggt gaggaagatg aagaggatga ggaggaggag     600
gaagatgaag aagatgaaga tgaagaagaa gatgatgatg atgaa                     645
```

<210> SEQ ID NO 13
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
atgggcaaag gagatcctaa gaagccgaga ggcaaaatgt catcatatgc attttttgtg      60
caaactagtc gggaggagca taagaagaag cacccagatg cttcagtcaa cttctcagag     120
ttttctaaga agagttcaga gaggtggaag accatgtctg ctaaagagaa aggaaaattt     180
gaagatatgg caaaggcgga caaggcccgt tatgaaagag aaatgaaaac ctatatccct     240
cccaaagggg agacaaaaaa gaagttcaag gatcccaatg cacccaagag gcctccttcg     300
```

```
gccttcttcc tcttctgctc tgagtatcgc ccaaaaatca aggagaaca tcctggcctg    360 tccattggtg atgttgcgaa gaaactggga gagatgtgga ataacactgc tgcagatgac    420
aagcagcctt atgaaaagaa ggctgcgaag ctgaaggaaa aatacgaaaa ggatattgct    480
gcatatcgag ctaaaggaaa gcctgatgca gcaaaaaagg gagttgtcaa ggctgaaaaa    540
agcaagaaaa agaaggaaga ggaggaaggt gaggaagatg aagaggatga ggaggaggag    600
gaagatgaag aagatgaaga tgaagaagaa gatgatgatg atgaa               645
```

```
<210> SEQ ID NO 14
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
atgggcaaag gagatcctaa gaagccgaga ggcaaaatgt catcatatgc atttttgtg     60 caaactagtc gggaggagca taagaagaag cacccagatg cttcagtcaa cttctcagag    120
ttttctaaga agtgctcaga gaggtggaag accatgtctg ctaaagagaa aggaaaattt    180
gaagatatgg caaaggcgga caaggcccgt tatgaaagag aaatgaaaac ctatatccct    240
cccaaggggg agacaaaaaa gaagttcaag gatcccaatg cacccaagag gcctccttcg    300
gccttcttcc tcttcagctc tgagtatcgc ccaaaaatca aggagaaca tcctggcctg    360 tccattggtg atgttgcgaa gaaactggga gagatgtgga ataacactgc tgcagatgac    420
aagcagcctt atgaaaagaa ggctgcgaag ctgaaggaaa aatacgaaaa ggatattgct    480
gcatatcgag ctaaaggaaa gcctgatgca gcaaaaaagg gagttgtcaa ggctgaaaaa    540
agcaagaaaa agaaggaaga ggaggaaggt gaggaagatg aagaggatga ggaggaggag    600
gaagatgaag aagatgaaga tgaagaagaa gatgatgatg atgaa               645
```

```
<210> SEQ ID NO 15
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
atgggcaaag gagatcctaa gaagccgaga ggcaaaatgt catcatatgc atttttgtg     60 caaacttgtc gggaggagca taagaagaag cacccagatg cttcagtcaa cttctcagag    120
ttttctaaga agagttcaga gaggtggaag accatgtctg ctaaagagaa aggaaaattt    180
gaagatatgg caaaggcgga caaggcccgt tatgaaagag aaatgaaaac ctatatccct    240
cccaaggggg agacaaaaaa gaagttcaag gatcccaatg cacccaagag gcctccttcg    300
gccttcttcc tcttcagctc tgagtatcgc ccaaaaatca aggagaaca tcctggcctg    360 tccattggtg atgttgcgaa gaaactggga gagatgtgga ataacactgc tgcagatgac    420
aagcagcctt atgaaaagaa ggctgcgaag ctgaaggaaa aatacgaaaa ggatattgct    480
gcatatcgag ctaaaggaaa gcctgatgca gcaaaaaagg gagttgtcaa ggctgaaaaa    540
agcaagaaaa agaaggaaga ggaggaaggt gaggaagatg aagaggatga ggaggaggag    600
gaagatgaag aagatgaaga tgaagaagaa gatgatgatg atgaa               645
```

<210> SEQ ID NO 16
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

```
atgggcaaag gagatcctaa gaagccgaga ggcaaaatgt catcatatgc attttttgtg      60
caaactagtc gggaggagca taagaagaag cacccagatg cttcagtcaa cttctcagag     120
ttttctaaga gagttcaga gaggtggaag accatgtctg ctaaagagaa aggaaaattt     180
gaagatatgg caaaggcgga caaggcccgt tatgaaagag aaatgaaaac ctatatccct     240
cccaaagggg agacaaaaaa gaagttcaag gatcccaatg cacccaagag gcctccttcg     300
gccttcttcc tcttcagctc tgagtatcgc ccaaaaatca aggagaacat cctggcctg     360
tccattggtg atgttgcgaa gaaactggga gagatgtgga ataacactgc tgcagatgac     420
aagcagcctt atgaaaagaa ggctgcgaag ctgaaggaaa atacgaaaa ggatattgct     480
gcatatcgag ctaaaggaaa gcctgatgca gcaaaaaagg gagttgtcaa ggctgaaaaa     540
agcaagaaaa agaaggaaga ggaggaaggt gaggaagatg aagaggatga ggaggaggag     600
gaagatgaag aagatgaaga tgaagaagaa gatgatgatg atgaa                     645
```

<210> SEQ ID NO 17
<211> LENGTH: 209
<212> TYPE: PRT
<213> ORGANISM: Homo sapiens

<400> SEQUENCE: 17

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp Glu
        195                 200                 205

Glu

<210> SEQ ID NO 18
<211> LENGTH: 209
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Gly Lys Gly Asp Pro Asn Lys Pro Arg Gly Lys Met Ser Ser Tyr
1               5                   10                  15

Ala Phe Phe Val Gln Thr Ser Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp Glu
        195                 200                 205

Glu

<210> SEQ ID NO 19
<211> LENGTH: 209
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Ser Ser Glu Arg
        35                  40                  45

```
Trp Lys Thr Met Ser Ala Lys Glu Lys Ser Lys Phe Glu Asp Met Ala
 50                  55                  60

Lys Ser Asp Lys Ala Arg Tyr Asp Arg Glu Met Lys Asn Tyr Val Pro
 65                  70                  75                  80

Pro Lys Gly Asp Lys Lys Gly Lys Lys Asp Pro Asn Ala Pro Lys
                 85                  90                  95

Arg Pro Pro Ser Ala Phe Phe Leu Phe Cys Ser Glu His Arg Pro Lys
                100                 105                 110

Ile Lys Ser Glu His Pro Gly Leu Ser Ile Gly Asp Thr Ala Lys Lys
                115                 120                 125

Leu Gly Glu Met Trp Ser Glu Gln Ser Ala Lys Asp Lys Gln Pro Tyr
130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
                180                 185                 190

Glu Glu Glu Glu Glu Asp Glu Asp Glu Glu Glu Asp Glu Asp Glu
                195                 200                 205

Glu
```

<210> SEQ ID NO 20
<211> LENGTH: 209
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Met Gly Lys Gly Asp Pro Asn Lys Pro Arg Gly Lys Met Ser Ser Tyr
 1                   5                  10                  15

Ala Phe Phe Val Gln Thr Cys Arg Glu Glu His Lys Lys Lys His Pro
                 20                  25                  30

Asp Ser Ser Val Asn Phe Ala Glu Phe Ser Lys Lys Cys Ser Glu Arg
                 35                  40                  45

Trp Lys Thr Met Ser Ala Lys Glu Lys Ser Lys Phe Glu Asp Met Ala
 50                  55                  60

Lys Ser Asp Lys Ala Arg Tyr Asp Arg Glu Met Lys Asn Tyr Val Pro
 65                  70                  75                  80

Pro Lys Gly Asp Lys Lys Gly Lys Lys Asp Pro Asn Ala Pro Lys
                 85                  90                  95

Arg Pro Pro Ser Ala Phe Phe Leu Phe Ser Ser Glu His Arg Pro Lys
                100                 105                 110

Ile Lys Ser Glu His Pro Gly Leu Ser Ile Gly Asp Thr Ala Lys Lys
                115                 120                 125

Leu Gly Glu Met Trp Ser Glu Gln Ser Ala Lys Asp Lys Gln Pro Tyr
130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
                180                 185                 190
```

```
Glu Glu Glu Glu Glu Asp Glu Asp Glu Glu Glu Asp Glu Asp Glu
            195                 200                 205

Glu
```

<210> SEQ ID NO 21
<211> LENGTH: 209
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

```
Met Gly Lys Gly Asp Pro Asn Lys Pro Arg Gly Lys Met Ser Ser Tyr
1               5                   10                  15

Ala Phe Phe Val Gln Thr Ser Arg Glu Glu His Lys Lys Lys His Pro
                20                  25                  30

Asp Ser Ser Val Asn Phe Ala Glu Phe Ser Lys Ser Ser Glu Arg
            35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
            115                 120                 125

Leu Gly Glu Met Trp Ser Glu Gln Ser Ala Lys Asp Lys Gln Pro Tyr
130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp Glu
            195                 200                 205

Glu
```

<210> SEQ ID NO 22
<211> LENGTH: 209
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

```
Met Gly Lys Gly Asp Pro Asn Lys Pro Arg Gly Lys Met Ser Ser Tyr
1               5                   10                  15

Ala Phe Phe Val Gln Thr Ser Arg Glu Glu His Lys Lys Lys His Pro
                20                  25                  30

Asp Ser Ser Val Asn Phe Ala Glu Phe Ser Lys Lys Cys Ser Glu Arg
            35                  40                  45
```

```
Trp Lys Thr Met Ser Ala Lys Glu Lys Ser Lys Phe Glu Asp Met Ala
 50                  55                  60

Lys Ser Asp Lys Ala Arg Tyr Asp Arg Glu Met Lys Asn Tyr Val Pro
 65                  70                  75                  80

Pro Lys Gly Asp Lys Lys Gly Lys Lys Lys Asp Pro Asn Ala Pro Lys
                 85                  90                  95

Arg Pro Pro Ser Ala Phe Phe Leu Phe Ser Ser Glu His Arg Pro Lys
                100                 105                 110

Ile Lys Ser Glu His Pro Gly Leu Ser Ile Gly Asp Thr Ala Lys Lys
                115                 120                 125

Leu Gly Glu Met Trp Ser Glu Gln Ser Ala Lys Asp Lys Gln Pro Tyr
                130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
                180                 185                 190

Glu Glu Glu Glu Glu Asp Glu Asp Glu Glu Glu Asp Glu Asp
                195                 200                 205

Glu
```

<210> SEQ ID NO 23
<211> LENGTH: 209
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Met Gly Lys Gly Asp Pro Asn Lys Pro Arg Gly Lys Met Ser Ser Tyr
 1                5                  10                  15

Ala Phe Phe Val Gln Thr Cys Arg Glu Glu His Lys Lys Lys His Pro
                 20                  25                  30

Asp Ser Ser Val Asn Phe Ala Glu Phe Ser Lys Lys Ser Ser Glu Arg
                 35                  40                  45

Trp Lys Thr Met Ser Ala Lys Glu Lys Ser Lys Phe Glu Asp Met Ala
 50                  55                  60

Lys Ser Asp Lys Ala Arg Tyr Asp Arg Glu Met Lys Asn Tyr Val Pro
 65                  70                  75                  80

Pro Lys Gly Asp Lys Lys Gly Lys Lys Lys Asp Pro Asn Ala Pro Lys
                 85                  90                  95

Arg Pro Pro Ser Ala Phe Phe Leu Phe Ser Ser Glu His Arg Pro Lys
                100                 105                 110

Ile Lys Ser Glu His Pro Gly Leu Ser Ile Gly Asp Thr Ala Lys Lys
                115                 120                 125

Leu Gly Glu Met Trp Ser Glu Gln Ser Ala Lys Asp Lys Gln Pro Tyr
                130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
```

180                 185                 190

Glu Glu Glu Glu Glu Asp Glu Asp Glu Glu Glu Asp Glu Asp Glu
        195                 200                 205

Glu

<210> SEQ ID NO 24
<211> LENGTH: 209
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Gly Lys Gly Asp Pro Asn Lys Pro Arg Gly Lys Met Ser Ser Tyr
1               5                   10                  15

Ala Phe Phe Val Gln Thr Ser Arg Glu Glu His Lys Lys Lys His Pro
            20                  25                  30

Asp Ser Val Asn Phe Ala Glu Phe Ser Lys Lys Ser Glu Arg
        35                  40                  45

Trp Lys Thr Met Ser Ala Lys Glu Lys Ser Lys Phe Glu Asp Met Ala
50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Ser Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp Glu
        195                 200                 205

Glu

<210> SEQ ID NO 25
<211> LENGTH: 630
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
atgggtaaag gagaccccaa caagccgcgg ggcaaaatgt cctcgtacgc cttcttcgtg     60
cagaccagtc gggaagagca caagaagaaa cacccggact cttccgtcaa tttcgcggaa   120
ttctccaaga agtgttcgga gagatggaag accatgtctg caaggagaa gtcgaagttt   180 gaagatatgg caaaaagtga caaagctcgc tatgacaggg agatgaaaaa ttacgttcct   240

```
cccaaggtg  ataagaaggg  gaagaaaaag  gaccccaatg  ctcctaaaag  gccaccatct    300
gccttcttcc  tgttttgctc  tgaacatcgc  ccaaagatca  aaagtgaaca  ccctggccta    360
tccattgggg  atactgcaaa  gaaattgggt  gaaatgtggt  ctgagcagtc  agccaaagat    420
aaacaaccat  atgaacagaa  agcagctaag  ctaaaggaga  aatatgaaaa  ggatattgct    480
gcatatcgtg  ccaagggcaa  aagtgaagca  ggaaagaagg  gccctggcag  gccaacaggc    540
tcaaagaaga  agaacgaacc  agaagatgag  gaggaggagg  aggaagaaga  agatgaagat    600
gaggaggaag  aggatgaaga  tgaagaataa                                       630
```

<210> SEQ ID NO 26
<211> LENGTH: 630
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
atgggtaaag  gagaccccaa  caagccgcgg  ggcaaaatgt  cctcgtacgc  cttcttcgtg     60
cagacctgcc  gggaagagca  caagaagaaa  cacccggact  cttccgtcaa  tttcgcggaa    120
ttctccaaga  gagttcgga   gagatggaag  accatgtctg  caaggagaa   gtcgaagttt    180 gaagatatgg  caaaaagtga  caaagctcgc  tatgacaggg  agatgaaaaa  ttacgttcct    240
cccaaaggtg  ataagaaggg  gaagaaaaag  gaccccaatg  ctcctaaaag  gccaccatct    300
gccttcttcc  tgttttgctc  tgaacatcgc  ccaaagatca  aaagtgaaca  ccctggccta    360
tccattgggg  atactgcaaa  gaaattgggt  gaaatgtggt  ctgagcagtc  agccaaagat    420
aaacaaccat  atgaacagaa  agcagctaag  ctaaaggaga  aatatgaaaa  ggatattgct    480
gcatatcgtg  ccaagggcaa  aagtgaagca  ggaaagaagg  gccctggcag  gccaacaggc    540
tcaaagaaga  agaacgaacc  agaagatgag  gaggaggagg  aggaagaaga  agatgaagat    600
gaggaggaag  aggatgaaga  tgaagaataa                                       630
```

<210> SEQ ID NO 27
<211> LENGTH: 630
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27

```
atgggtaaag  gagaccccaa  caagccgcgg  ggcaaaatgt  cctcgtacgc  cttcttcgtg     60
cagacctgcc  gggaagagca  caagaagaaa  cacccggact  cttccgtcaa  tttcgcggaa    120
ttctccaaga  agtgttcgga  gagatggaag  accatgtctg  caaggagaa   gtcgaagttt    180 gaagatatgg  caaaaagtga  caaagctcgc  tatgacaggg  agatgaaaaa  ttacgttcct    240
cccaaaggtg  ataagaaggg  gaagaaaaag  gaccccaatg  ctcctaaaag  gccaccatct    300
gccttcttcc  tgtttagctc  tgaacatcgc  ccaaagatca  aaagtgaaca  ccctggccta    360
tccattgggg  atactgcaaa  gaaattgggt  gaaatgtggt  ctgagcagtc  agccaaagat    420
aaacaaccat  atgaacagaa  agcagctaag  ctaaaggaga  aatatgaaaa  ggatattgct    480
gcatatcgtg  ccaagggcaa  aagtgaagca  ggaaagaagg  gccctggcag  gccaacaggc    540
```

```
tcaaagaaga agaacgaacc agaagatgag gaggaggagg aggaagaaga agatgaagat    600
gaggaggaag aggatgaaga tgaagaataa                                    630
```

<210> SEQ ID NO 28
<211> LENGTH: 630
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28

```
atgggtaaag gagaccccaa caagccgcgg ggcaaaatgt cctcgtacgc cttcttcgtg     60
cagaccagtc gggaagagca caagaagaaa caccccggact cttccgtcaa tttcgcggaa   120
ttctccaaga agagttcgga gagatggaag accatgtctg caaggagaa gtcgaagttt    180 gaagatatgg caaaaagtga caaagctcgc tatgacaggg agatgaaaaa ttacgttcct    240
cccaaaggtg ataagaaggg gaagaaaaag gaccccaatg ctcctaaaag gccaccatct    300
gccttcttcc tgttttgctc tgaacatcgc ccaaagatca aagtgaaca ccctggccta    360 tccattgggg atactgcaaa gaaattgggt gaaatgtggt ctgagcagtc agccaaagat    420
aaacaaccat atgaacagaa agcagctaag ctaaaggaga aatatgaaaa ggatattgct    480
gcatatcgtg ccaagggcaa aagtgaagca ggaaagaagg ccctggcag gccaacaggc    540 tcaaagaaga agaacgaacc agaagatgag gaggaggagg aggaagaaga agatgaagat    600
gaggaggaag aggatgaaga tgaagaataa                                    630
```

<210> SEQ ID NO 29
<211> LENGTH: 630
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29

```
atgggtaaag gagaccccaa caagccgcgg ggcaaaatgt cctcgtacgc cttcttcgtg     60
cagaccagtc gggaagagca caagaagaaa caccccggact cttccgtcaa tttcgcggaa   120
ttctccaaga agtgttcgga gagatggaag accatgtctg caaggagaa gtcgaagttt    180 gaagatatgg caaaaagtga caaagctcgc tatgacaggg agatgaaaaa ttacgttcct    240
cccaaaggtg ataagaaggg gaagaaaaag gaccccaatg ctcctaaaag gccaccatct    300
gccttcttcc tgtttagctc tgaacatcgc ccaaagatca aagtgaaca ccctggccta    360 tccattgggg atactgcaaa gaaattgggt gaaatgtggt ctgagcagtc agccaaagat    420
aaacaaccat atgaacagaa agcagctaag ctaaaggaga aatatgaaaa ggatattgct    480
gcatatcgtg ccaagggcaa aagtgaagca ggaaagaagg ccctggcag gccaacaggc    540 tcaaagaaga agaacgaacc agaagatgag gaggaggagg aggaagaaga agatgaagat    600
gaggaggaag aggatgaaga tgaagaataa                                    630
```

<210> SEQ ID NO 30
<211> LENGTH: 630
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 30

| | | | | | |
|---|---|---|---|---|---|
| atgggtaaag | gagaccccaa | caagccgcgg | ggcaaaatgt | cctcgtacgc | cttcttcgtg | 60 |
| cagacctgcc | gggaagagca | caagaagaaa | cacccggact | cttccgtcaa | tttcgcggaa | 120 |
| ttctccaaga | gagttcgga | gagatggaag | accatgtctg | caaggagaa | gtcgaagttt | 180 |
| gaagatatgg | caaaaagtga | caaagctcgc | tatgacaggg | agatgaaaaa | ttacgttcct | 240 |
| cccaaaggtg | ataagaaggg | gaagaaaaag | gaccccaatg | ctcctaaaag | gccaccatct | 300 |
| gccttcttcc | tgtttagctc | tgaacatcgc | ccaaagatca | aaagtgaaca | ccctggccta | 360 |
| tccattgggg | atactgcaaa | gaaattgggt | gaaatgtggt | ctgagcagtc | agccaaagat | 420 |
| aaacaaccat | atgaacagaa | agcagctaag | ctaaaggaga | aatatgaaaa | ggatattgct | 480 |
| gcatatcgtg | ccaagggcaa | aagtgaagca | ggaaagaagg | gccctggcag | gccaacaggc | 540 |
| tcaaagaaga | gaacgaacc | agaagatgag | gaggaggagg | aggaagaaga | agatgaagat | 600 |
| gaggaggaag | aggatgaaga | tgaagaataa | | | | 630 |

<210> SEQ ID NO 31
<211> LENGTH: 630
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 31

| | | | | | |
|---|---|---|---|---|---|
| atgggtaaag | gagaccccaa | caagccgcgg | ggcaaaatgt | cctcgtacgc | cttcttcgtg | 60 |
| cagaccagtc | gggaagagca | caagaagaaa | cacccggact | cttccgtcaa | tttcgcggaa | 120 |
| ttctccaaga | gagttcgga | gagatggaag | accatgtctg | caaggagaa | gtcgaagttt | 180 |
| gaagatatgg | caaaaagtga | caaagctcgc | tatgacaggg | agatgaaaaa | ttacgttcct | 240 |
| cccaaaggtg | ataagaaggg | gaagaaaaag | gaccccaatg | ctcctaaaag | gccaccatct | 300 |
| gccttcttcc | tgtttagctc | tgaacatcgc | ccaaagatca | aaagtgaaca | ccctggccta | 360 |
| tccattgggg | atactgcaaa | gaaattgggt | gaaatgtggt | ctgagcagtc | agccaaagat | 420 |
| aaacaaccat | atgaacagaa | agcagctaag | ctaaaggaga | aatatgaaaa | ggatattgct | 480 |
| gcatatcgtg | ccaagggcaa | aagtgaagca | ggaaagaagg | gccctggcag | gccaacaggc | 540 |
| tcaaagaaga | gaacgaacc | agaagatgag | gaggaggagg | aggaagaaga | agatgaagat | 600 |
| gaggaggaag | aggatgaaga | tgaagaataa | | | | 630 |

<210> SEQ ID NO 32
<211> LENGTH: 200
<212> TYPE: PRT
<213> ORGANISM: Homo sapiens

<400> SEQUENCE: 32

```
Met Ala Lys Gly Asp Pro Lys Lys Pro Lys Gly Lys Met Ser Ala Tyr
1               5                   10                  15

Ala Phe Phe Val Gln Thr Cys Arg Glu Glu His Lys Lys Lys Asn Pro
            20                  25                  30

Glu Val Pro Val Asn Phe Ala Glu Phe Ser Lys Lys Cys Ser Glu Arg
        35                  40                  45

Trp Lys Thr Met Ser Gly Lys Glu Lys Ser Lys Phe Asp Glu Met Ala
```

```
                 50                  55                  60
Lys Ala Asp Lys Val Arg Tyr Asp Arg Glu Met Lys Asp Tyr Gly Pro
 65                  70                  75                  80

Ala Lys Gly Gly Lys Lys Lys Asp Pro Asn Ala Pro Lys Arg Pro
                 85                  90                  95

Pro Ser Gly Phe Phe Leu Phe Cys Ser Glu Phe Arg Pro Lys Ile Lys
                100                 105                 110

Ser Thr Asn Pro Gly Ile Ser Ile Gly Asp Val Ala Lys Lys Leu Gly
                115                 120                 125

Glu Met Trp Asn Asn Leu Asn Asp Ser Glu Lys Gln Pro Tyr Ile Thr
            130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Asp Glu Glu Glu Glu Glu Glu Glu Glu
            180                 185                 190

Glu Glu Glu Glu Glu Glu Asp Glu
            195                 200

<210> SEQ ID NO 33
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Ala Lys Gly Asp Pro Lys Lys Pro Lys Gly Lys Met Ser Ala Tyr
  1               5                  10                  15

Ala Phe Phe Val Gln Thr Ser Arg Glu Glu His Lys Lys Lys Asn Pro
                 20                  25                  30

Glu Val Pro Val Asn Phe Ala Glu Phe Ser Lys Lys Cys Ser Glu Arg
                 35                  40                  45

Trp Lys Thr Met Ser Gly Lys Glu Lys Ser Lys Phe Asp Glu Met Ala
 50                  55                  60

Lys Ala Asp Lys Val Arg Tyr Asp Arg Glu Met Lys Asp Tyr Gly Pro
 65                  70                  75                  80

Ala Lys Gly Gly Lys Lys Lys Asp Pro Asn Ala Pro Lys Arg Pro
                 85                  90                  95

Pro Ser Gly Phe Phe Leu Phe Cys Ser Glu Phe Arg Pro Lys Ile Lys
                100                 105                 110

Ser Thr Asn Pro Gly Ile Ser Ile Gly Asp Val Ala Lys Lys Leu Gly
                115                 120                 125

Glu Met Trp Asn Asn Leu Asn Asp Ser Glu Lys Gln Pro Tyr Ile Thr
            130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Asp Glu Glu Glu Glu Glu Glu Glu Glu
            180                 185                 190

Glu Glu Glu Glu Glu Glu Asp Glu
            195                 200
```

<210> SEQ ID NO 34
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

```
Met Ala Lys Gly Asp Pro Lys Pro Lys Gly Lys Met Ser Ala Tyr
 1               5                  10                  15

Ala Phe Phe Val Gln Thr Cys Arg Glu Glu His Lys Lys Lys Asn Pro
                20                  25                  30

Glu Val Pro Val Asn Phe Ala Glu Phe Ser Lys Lys Ser Ser Glu Arg
            35                  40                  45

Trp Lys Thr Met Ser Gly Lys Glu Lys Ser Lys Phe Asp Glu Met Ala
        50                  55                  60

Lys Ala Asp Lys Val Arg Tyr Asp Arg Glu Met Lys Asp Tyr Gly Pro
65                  70                  75                  80

Ala Lys Gly Gly Lys Lys Lys Asp Pro Asn Ala Pro Lys Arg Pro
                85                  90                  95

Pro Ser Gly Phe Phe Leu Phe Cys Ser Glu Phe Arg Pro Lys Ile Lys
                100                 105                 110

Ser Thr Asn Pro Gly Ile Ser Ile Gly Asp Val Ala Lys Lys Leu Gly
            115                 120                 125

Glu Met Trp Asn Asn Leu Asn Asp Ser Glu Lys Gln Pro Tyr Ile Thr
        130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Asp Glu Glu Glu Glu Glu Glu
            180                 185                 190

Glu Glu Glu Glu Glu Glu Asp Glu
        195                 200
```

<210> SEQ ID NO 35
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

```
Met Ala Lys Gly Asp Pro Lys Pro Lys Gly Lys Met Ser Ala Tyr
 1               5                  10                  15

Ala Phe Phe Val Gln Thr Cys Arg Glu Glu His Lys Lys Lys Asn Pro
                20                  25                  30

Glu Val Pro Val Asn Phe Ala Glu Phe Ser Lys Lys Cys Ser Glu Arg
            35                  40                  45

Trp Lys Thr Met Ser Gly Lys Glu Lys Ser Lys Phe Asp Glu Met Ala
        50                  55                  60

Lys Ala Asp Lys Val Arg Tyr Asp Arg Glu Met Lys Asp Tyr Gly Pro
65                  70                  75                  80
```

```
Ala Lys Gly Gly Lys Lys Lys Asp Pro Asn Ala Pro Lys Arg Pro
            85                  90                  95

Pro Ser Gly Phe Phe Leu Phe Ser Ser Glu Phe Arg Pro Lys Ile Lys
        100                 105                 110

Ser Thr Asn Pro Gly Ile Ser Ile Gly Asp Val Ala Lys Lys Leu Gly
        115                 120                 125

Glu Met Trp Asn Asn Leu Asn Asp Ser Glu Lys Gln Pro Tyr Ile Thr
        130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Asp Glu Glu Glu Glu Glu Glu Glu Glu
                180                 185                 190

Glu Glu Glu Glu Glu Glu Asp Glu
        195                 200
```

<210> SEQ ID NO 36
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Met Ala Lys Gly Asp Pro Lys Lys Pro Lys Gly Lys Met Ser Ala Tyr
1               5                   10                  15

Ala Phe Phe Val Gln Thr Ser Arg Glu Glu His Lys Lys Lys Asn Pro
            20                  25                  30

Glu Val Pro Val Asn Phe Ala Glu Phe Ser Lys Lys Ser Ser Glu Arg
        35                  40                  45

Trp Lys Thr Met Ser Gly Lys Glu Lys Ser Lys Phe Asp Glu Met Ala
    50                  55                  60

Lys Ala Asp Lys Val Arg Tyr Asp Arg Glu Met Lys Asp Tyr Gly Pro
65                  70                  75                  80

Ala Lys Gly Gly Lys Lys Lys Asp Pro Asn Ala Pro Lys Arg Pro
            85                  90                  95

Pro Ser Gly Phe Phe Leu Phe Cys Ser Glu Phe Arg Pro Lys Ile Lys
        100                 105                 110

Ser Thr Asn Pro Gly Ile Ser Ile Gly Asp Val Ala Lys Lys Leu Gly
        115                 120                 125

Glu Met Trp Asn Asn Leu Asn Asp Ser Glu Lys Gln Pro Tyr Ile Thr
        130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Asp Glu Glu Glu Glu Glu Glu Glu Glu
                180                 185                 190

Glu Glu Glu Glu Glu Glu Asp Glu
        195                 200
```

<210> SEQ ID NO 37
<211> LENGTH: 384
<212> TYPE: PRT

<213> ORGANISM: Homo sapiens

<400> SEQUENCE: 37

```
Ala Pro Thr Lys Ala Pro Asp Val Phe Pro Ile Ile Ser Gly Cys Arg
1               5                  10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Ser Pro Gln Pro Ala Thr
            340                 345                 350

Tyr Thr Cys Val Val Ser His Glu Asp Ser Arg Thr Leu Leu Asn Ala
        355                 360                 365

Ser Arg Ser Leu Glu Val Ser Tyr Val Thr Asp His Gly Pro Met Lys
    370                 375                 380
```

<210> SEQ ID NO 38
<211> LENGTH: 330

<212> TYPE: PRT
<213> ORGANISM: Homo sapiens

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 39
<211> LENGTH: 326
<212> TYPE: PRT
<213> ORGANISM: Homo sapiens

<400> SEQUENCE: 39

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 40
<211> LENGTH: 377
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                      40                  45

Gly Val His Thr Phe Pro Ala Val Leu Gln Ser Ser Gly Leu Tyr Ser
         50                  55                  60
```

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
            85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
            370                 375

<210> SEQ ID NO 41
<211> LENGTH: 452
<212> TYPE: PRT
<213> ORGANISM: Homo sapiens

<400> SEQUENCE: 41

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys

```
                50                  55                  60
Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
        435                 440                 445

Gly Thr Cys Tyr
    450

<210> SEQ ID NO 42
```

```
<211> LENGTH: 327
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 43
<211> LENGTH: 353
<212> TYPE: PRT
<213> ORGANISM: Homo sapiens

<400> SEQUENCE: 43

Ala Ser Pro Thr Ser Pro Lys Val Phe Pro Leu Ser Leu Cys Ser Thr
1               5                   10                  15
```

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 44
<211> LENGTH: 340
<212> TYPE: PRT
<213> ORGANISM: Homo sapiens

<400> SEQUENCE: 44

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

-continued

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
 50                  55                  60

Thr Thr Ser Ser Gln Leu Thr Leu Pro Ala Thr Gln Cys Pro Asp Gly
 65                  70                  75                  80

Lys Ser Val Thr Cys His Val Lys His Tyr Thr Asn Pro Ser Gln Asp
                 85                  90                  95

Val Thr Val Pro Cys Pro Val Pro Pro Pro Pro Cys Cys His Pro Arg
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Met Ala Glu Val Asp
                325                 330                 335

Gly Thr Cys Tyr
            340

<210> SEQ ID NO 45
<211> LENGTH: 106
<212> TYPE: PRT
<213> ORGANISM: Homo sapiens

<400> SEQUENCE: 45

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr

```
Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 46
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Met Ala Lys Gly Asp Pro Lys Lys Pro Lys Gly Lys Met Ser Ala Tyr
1               5                   10                  15

Ala Phe Phe Val Gln Thr Ser Arg Glu Glu His Lys Lys Lys Asn Pro
                20                  25                  30

Glu Val Pro Val Asn Phe Ala Glu Phe Ser Lys Lys Cys Ser Glu Arg
            35                  40                  45

Trp Lys Thr Met Ser Gly Lys Glu Lys Ser Lys Phe Asp Glu Met Ala
50                  55                  60

Lys Ala Asp Lys Val Arg Tyr Asp Arg Glu Met Lys Asp Tyr Gly Pro
65                  70                  75                  80

Ala Lys Gly Gly Lys Lys Lys Asp Pro Asn Ala Pro Lys Arg Pro
                85                  90                  95

Pro Ser Gly Phe Phe Leu Phe Ser Glu Phe Arg Pro Lys Ile Lys
            100                 105                 110

Ser Thr Asn Pro Gly Ile Ser Ile Gly Asp Val Ala Lys Lys Leu Gly
            115                 120                 125

Glu Met Trp Asn Asn Leu Asn Asp Ser Glu Lys Gln Pro Tyr Ile Thr
130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Asp Glu Glu Glu Glu Glu Glu Glu Glu
            180                 185                 190

Glu Glu Glu Glu Glu Glu Asp Glu
            195                 200
```

<210> SEQ ID NO 47
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Met Ala Lys Gly Asp Pro Lys Lys Pro Lys Gly Lys Met Ser Ala Tyr
1               5                   10                  15

Ala Phe Phe Val Gln Thr Cys Arg Glu Glu His Lys Lys Lys Asn Pro
                20                  25                  30
```

```
Glu Val Pro Val Asn Phe Ala Glu Phe Ser Lys Lys Ser Ser Glu Arg
            35                  40                  45

Trp Lys Thr Met Ser Gly Lys Glu Lys Ser Lys Phe Asp Glu Met Ala
 50                  55                  60

Lys Ala Asp Lys Val Arg Tyr Asp Arg Glu Met Lys Asp Tyr Gly Pro
 65                  70                  75                  80

Ala Lys Gly Gly Lys Lys Lys Asp Pro Asn Ala Pro Lys Arg Pro
                85                  90                  95

Pro Ser Gly Phe Phe Leu Phe Ser Ser Glu Phe Arg Pro Lys Ile Lys
            100                 105                 110

Ser Thr Asn Pro Gly Ile Ser Ile Gly Asp Val Ala Lys Lys Leu Gly
            115                 120                 125

Glu Met Trp Asn Asn Leu Asn Asp Ser Glu Lys Gln Pro Tyr Ile Thr
            130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Asp Glu Glu Glu Glu Glu Glu Glu Glu
            180                 185                 190

Glu Glu Glu Glu Glu Glu Asp Glu
            195                 200

<210> SEQ ID NO 48
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Met Ala Lys Gly Asp Pro Lys Pro Lys Gly Lys Met Ser Ala Tyr
 1               5                  10                  15

Ala Phe Phe Val Gln Thr Ser Arg Glu Glu His Lys Lys Lys Asn Pro
                20                  25                  30

Glu Val Pro Val Asn Phe Ala Glu Phe Ser Lys Lys Ser Ser Glu Arg
            35                  40                  45

Trp Lys Thr Met Ser Gly Lys Glu Lys Ser Lys Phe Asp Glu Met Ala
 50                  55                  60

Lys Ala Asp Lys Val Arg Tyr Asp Arg Glu Met Lys Asp Tyr Gly Pro
 65                  70                  75                  80

Ala Lys Gly Gly Lys Lys Lys Asp Pro Asn Ala Pro Lys Arg Pro
                85                  90                  95

Pro Ser Gly Phe Phe Leu Phe Ser Ser Glu Phe Arg Pro Lys Ile Lys
            100                 105                 110

Ser Thr Asn Pro Gly Ile Ser Ile Gly Asp Val Ala Lys Lys Leu Gly
            115                 120                 125

Glu Met Trp Asn Asn Leu Asn Asp Ser Glu Lys Gln Pro Tyr Ile Thr
            130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175
```

Arg Lys Lys Val Glu Glu Glu Asp Glu Glu Glu Glu Glu Glu
            180                 185                 190
Glu Glu Glu Glu Glu Glu Asp Glu
        195                 200

<210> SEQ ID NO 49
<211> LENGTH: 604
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49

| | | | | | | |
|---|---|---|---|---|---|---|
| atggctaaag | gtgaccccaa | gaaaccaaag | ggcaagatgt | ccgcttatgc | cttctttgtg | 60 |
| cagacaagtc | agagaagaac | ataagaagaa | aacccagag | gtccctgtca | attttgcgga | 120 |
| attttccaag | aagtgctctg | agaggtggaa | gacgatgtcc | gggaaagaga | aatctaaatt | 180 |
| tgatgaaatg | gcaaaggcag | ataaagtgcg | ctatgatcgg | gaaatgaagg | attatggacc | 240 |
| agctaaggga | ggcaagaaga | agaaggatcc | taatgctccc | aaaaggccac | cgtctggatt | 300 |
| cttcctgttc | tgttcagaat | tccgccccaa | gatcaaatcc | acaaccccg | gcatctctat | 360 |
| tggagacgtg | gcaaaaaagc | tgggtgagat | gtggaataat | ttaaatgaca | gtgaaaagca | 420 |
| gccttacatc | actaaggcgg | caaagctgaa | ggagaagtat | gagaaggatg | ttgctgacta | 480 |
| taagtcgaaa | ggaaagtttg | atggtgcaaa | gggtcctgct | aaagttgccc | ggaaaaaggt | 540 |
| ggaagaggaa | gatgaagaag | aggaggagga | agaagaggag | gaggaggagg | aggaggatga | 600 |
| ataa | | | | | | 604 |

<210> SEQ ID NO 50
<211> LENGTH: 604
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50

| | | | | | | |
|---|---|---|---|---|---|---|
| atggctaaag | gtgaccccaa | gaaaccaaag | ggcaagatgt | ccgcttatgc | cttctttgtg | 60 |
| cagacatgcc | agagaagaac | ataagaagaa | aacccagag | gtccctgtca | attttgcgga | 120 |
| attttccaag | aagagttctg | agaggtggaa | gacgatgtcc | gggaaagaga | aatctaaatt | 180 |
| tgatgaaatg | gcaaaggcag | ataaagtgcg | ctatgatcgg | gaaatgaagg | attatggacc | 240 |
| agctaaggga | ggcaagaaga | agaaggatcc | taatgctccc | aaaaggccac | cgtctggatt | 300 |
| cttcctgttc | tgttcagaat | tccgccccaa | gatcaaatcc | acaaccccg | gcatctctat | 360 |
| tggagacgtg | gcaaaaaagc | tgggtgagat | gtggaataat | ttaaatgaca | gtgaaaagca | 420 |
| gccttacatc | actaaggcgg | caaagctgaa | ggagaagtat | gagaaggatg | ttgctgacta | 480 |
| taagtcgaaa | ggaaagtttg | atggtgcaaa | gggtcctgct | aaagttgccc | ggaaaaaggt | 540 |
| ggaagaggaa | gatgaagaag | aggaggagga | agaagaggag | gaggaggagg | aggaggatga | 600 |
| ataa | | | | | | 604 |

<210> SEQ ID NO 51
<211> LENGTH: 604
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 51
atggctaaag gtgaccccaa gaaaccaaag ggcaagatgt ccgcttatgc cttctttgtg    60
cagacatgcc agagaagaac ataagaagaa aaacccagag gtccctgtca attttgcgga  120
attttccaag aagtgctctg agaggtggaa gacgatgtcc gggaaagaga aatctaaatt  180
tgatgaaatg gcaaaggcag ataaagtgcg ctatgatcgg gaaatgaagg attatggacc  240
agctaaggga ggcaagaaga gaaggatcc taatgctccc aaaaggccac cgtctggatt    300
cttcctgttc agctcagaat tccgccccaa gatcaaatcc acaaaccccg gcatctctat  360
tggagacgtg gcaaaaaagc tgggtgagat gtggaataat ttaaatgaca gtgaaaagca  420
gccttacatc actaaggcgg caaagctgaa ggagaagtat gagaaggatg ttgctgacta  480
taagtcgaaa ggaaagtttg atggtgcaaa gggtcctgct aaagttgccc ggaaaaaggt  540
ggaagaggaa gatgaagaag aggaggagga agaagaggag gaggaggagg aggaggatga  600
ataa                                                                604

<210> SEQ ID NO 52
<211> LENGTH: 604
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52
atggctaaag gtgaccccaa gaaaccaaag ggcaagatgt ccgcttatgc cttctttgtg    60
cagacaagtc agagaagaac ataagaagaa aaacccagag gtccctgtca attttgcgga  120
attttccaag aagagttctg agaggtggaa gacgatgtcc gggaaagaga aatctaaatt  180
tgatgaaatg gcaaaggcag ataaagtgcg ctatgatcgg gaaatgaagg attatggacc  240
agctaaggga ggcaagaaga gaaggatcc taatgctccc aaaaggccac cgtctggatt    300
cttcctgttc tgttcagaat tccgccccaa gatcaaatcc acaaaccccg gcatctctat  360
tggagacgtg gcaaaaaagc tgggtgagat gtggaataat ttaaatgaca gtgaaaagca  420
gccttacatc actaaggcgg caaagctgaa ggagaagtat gagaaggatg ttgctgacta  480
taagtcgaaa ggaaagtttg atggtgcaaa gggtcctgct aaagttgccc ggaaaaaggt  540
ggaagaggaa gatgaagaag aggaggagga agaagaggag gaggaggagg aggaggatga  600
ataa                                                                604

<210> SEQ ID NO 53
<211> LENGTH: 604
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
atggctaaag gtgaccccaa gaaaccaaag ggcaagatgt ccgcttatgc cttctttgtg    60
cagacaagtc agagaagaac ataagaagaa aaacccagag gtccctgtca attttgcgga  120
```
attttccaag aagtgctctg agaggtggaa gacgatgtcc gggaaagaga aatctaaatt    180
tgatgaaatg gcaaaggcag ataaagtgcg ctatgatcgg gaaatgaagg attatggacc    240
agctaaggga ggcaagaaga agaaggatcc taatgctccc aaaaggccac cgtctggatt    300
cttcctgttc agctcagaat tccgccccaa gatcaaatcc acaaacccg gcatctctat    360 tggagacgtg gcaaaaaagc tgggtgagat gtggaataat ttaaatgaca gtgaaaagca    420
gccttacatc actaaggcgg caaagctgaa ggagaagtat gagaaggatg ttgctgacta    480
taagtcgaaa ggaaagtttg atggtgcaaa gggtcctgct aaagttgccc ggaaaaaggt    540
ggaagaggaa gatgaagaag aggaggagga agaagaggag gaggaggagg aggaggatga    600
ataa                                                                604

<210> SEQ ID NO 54
<211> LENGTH: 604
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
atggctaaag gtgaccccaa gaaaccaaag ggcaagatgt ccgcttatgc cttctttgtg     60
cagacatgcc agagaagaac ataagaagaa aaacccagag gtccctgtca attttgcgga    120
attttccaag aagagttctg agaggtggaa gacgatgtcc gggaaagaga aatctaaatt    180
tgatgaaatg gcaaaggcag ataaagtgcg ctatgatcgg gaaatgaagg attatggacc    240
agctaaggga ggcaagaaga agaaggatcc taatgctccc aaaaggccac cgtctggatt    300
cttcctgttc agctcagaat tccgccccaa gatcaaatcc acaaacccg gcatctctat    360 tggagacgtg gcaaaaaagc tgggtgagat gtggaataat ttaaatgaca gtgaaaagca    420
gccttacatc actaaggcgg caaagctgaa ggagaagtat gagaaggatg ttgctgacta    480
taagtcgaaa ggaaagtttg atggtgcaaa gggtcctgct aaagttgccc ggaaaaaggt    540
ggaagaggaa gatgaagaag aggaggagga agaagaggag gaggaggagg aggaggatga    600
ataa                                                                604

<210> SEQ ID NO 55
<211> LENGTH: 604
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
atggctaaag gtgaccccaa gaaaccaaag ggcaagatgt ccgcttatgc cttctttgtg     60
cagacaagtc agagaagaac ataagaagaa aaacccagag gtccctgtca attttgcgga    120
attttccaag aagagttctg agaggtggaa gacgatgtcc gggaaagaga aatctaaatt    180
tgatgaaatg gcaaaggcag ataaagtgcg ctatgatcgg gaaatgaagg attatggacc    240
agctaaggga ggcaagaaga agaaggatcc taatgctccc aaaaggccac cgtctggatt    300
cttcctgttc agctcagaat tccgccccaa gatcaaatcc acaaacccg gcatctctat    360 tggagacgtg gcaaaaaagc tgggtgagat gtggaataat ttaaatgaca gtgaaaagca    420
gccttacatc actaaggcgg caaagctgaa ggagaagtat gagaaggatg ttgctgacta    480

```
taagtcgaaa ggaaagtttg atggtgcaaa gggtcctgct aaagttgccc ggaaaaaggt    540
ggaagaggaa gatgaagaag aggaggagga agaagaggag gaggaggagg aggaggatga    600
ataa                                                                 604
```

<210> SEQ ID NO 56
<211> LENGTH: 186
<212> TYPE: PRT
<213> ORGANISM: Homo sapiens

<400> SEQUENCE: 56

```
Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Cys Ser Glu Lys
        35                  40                  45

Trp Arg Ser Ile Ser Lys His Glu Lys Ala Lys Tyr Glu Ala Leu Ala
    50                  55                  60

Lys Leu Asp Lys Ala Arg Tyr Gln Glu Glu Met Met Asn Tyr Val Gly
65                  70                  75                  80

Lys Arg Lys Lys Arg Arg Lys Arg Asp Pro Gln Glu Pro Arg Arg Pro
                85                  90                  95

Pro Ser Ser Phe Leu Leu Phe Cys Gln Asp His Tyr Ala Gln Leu Lys
            100                 105                 110

Arg Glu Asn Pro Asn Trp Ser Val Val Gln Val Ala Lys Ala Thr Gly
        115                 120                 125

Lys Met Trp Ser Thr Ala Thr Asp Leu Glu Lys His Pro Tyr Glu Gln
    130                 135                 140

Arg Val Ala Leu Leu Arg Ala Lys Tyr Phe Glu Glu Leu Glu Leu Tyr
145                 150                 155                 160

Arg Lys Gln Cys Asn Ala Arg Lys Lys Tyr Arg Met Ser Ala Arg Asn
                165                 170                 175

Arg Cys Arg Gly Lys Arg Val Arg Gln Ser
            180                 185
```

<210> SEQ ID NO 57
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

```
Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Ser Ser Glu Lys
        35                  40                  45

Trp Arg Ser Ile Ser Lys His Glu Lys Ala Lys Tyr Glu Ala Leu Ala
    50                  55                  60

Lys Leu Asp Lys Ala Arg Tyr Gln Glu Glu Met Met Asn Tyr Val Gly
65                  70                  75                  80

Lys Arg Lys Lys Arg Arg Lys Arg Asp Pro Gln Glu Pro Arg Arg Pro
```

```
                    85                  90                  95
Pro Ser Ser Phe Leu Leu Phe Cys Gln Asp His Tyr Ala Gln Leu Lys
            100                 105                 110

Arg Glu Asn Pro Asn Trp Ser Val Val Gln Val Ala Lys Ala Thr Gly
            115                 120                 125

Lys Met Trp Ser Thr Ala Thr Asp Leu Glu Lys His Pro Tyr Glu Gln
            130                 135                 140

Arg Val Ala Leu Leu Arg Ala Lys Tyr Phe Glu Glu Leu Glu Leu Tyr
145                 150                 155                 160

Arg Lys Gln Cys Asn Ala Arg Lys Lys Tyr Arg Met Ser Ala Arg Asn
                165                 170                 175

Arg Cys Arg Gly Lys Arg Val Arg Gln Ser
            180                 185

<210> SEQ ID NO 58
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Cys Ser Glu Lys
        35                  40                  45

Trp Arg Ser Ile Ser Lys His Glu Lys Ala Lys Tyr Glu Ala Leu Ala
    50                  55                  60

Lys Leu Asp Lys Ala Arg Tyr Gln Glu Glu Met Met Asn Tyr Val Gly
65                  70                  75                  80

Lys Arg Lys Lys Arg Arg Lys Arg Asp Pro Gln Glu Pro Arg Arg Pro
                85                  90                  95

Pro Ser Ser Phe Leu Leu Phe Ser Gln Asp His Tyr Ala Gln Leu Lys
            100                 105                 110

Arg Glu Asn Pro Asn Trp Ser Val Val Gln Val Ala Lys Ala Thr Gly
            115                 120                 125

Lys Met Trp Ser Thr Ala Thr Asp Leu Glu Lys His Pro Tyr Glu Gln
            130                 135                 140

Arg Val Ala Leu Leu Arg Ala Lys Tyr Phe Glu Glu Leu Glu Leu Tyr
145                 150                 155                 160

Arg Lys Gln Cys Asn Ala Arg Lys Lys Tyr Arg Met Ser Ala Arg Asn
                165                 170                 175

Arg Cys Arg Gly Lys Arg Val Arg Gln Ser
            180                 185

<210> SEQ ID NO 59
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59
```

```
Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Cys Ser Glu Lys
                35                  40                  45

Trp Arg Ser Ile Ser Lys His Glu Lys Ala Lys Tyr Glu Ala Leu Ala
        50                  55                  60

Lys Leu Asp Lys Ala Arg Tyr Gln Glu Glu Met Met Asn Tyr Val Gly
65                  70                  75                  80

Lys Arg Lys Lys Arg Lys Arg Asp Pro Gln Glu Pro Arg Arg Pro
                85                  90                  95

Pro Ser Ser Phe Leu Leu Phe Cys Gln Asp His Tyr Ala Gln Leu Lys
                100                 105                 110

Arg Glu Asn Pro Asn Trp Ser Val Val Gln Val Ala Lys Ala Thr Gly
            115                 120                 125

Lys Met Trp Ser Thr Ala Thr Asp Leu Glu Lys His Pro Tyr Glu Gln
130                 135                 140

Arg Val Ala Leu Leu Arg Ala Lys Tyr Phe Glu Glu Leu Glu Leu Tyr
145                 150                 155                 160

Arg Lys Gln Ser Asn Ala Arg Lys Lys Tyr Arg Met Ser Ala Arg Asn
                165                 170                 175

Arg Cys Arg Gly Lys Arg Val Arg Gln Ser
                180                 185

<210> SEQ ID NO 60
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Cys Ser Glu Lys
                35                  40                  45

Trp Arg Ser Ile Ser Lys His Glu Lys Ala Lys Tyr Glu Ala Leu Ala
        50                  55                  60

Lys Leu Asp Lys Ala Arg Tyr Gln Glu Glu Met Met Asn Tyr Val Gly
65                  70                  75                  80

Lys Arg Lys Lys Arg Lys Arg Asp Pro Gln Glu Pro Arg Arg Pro
                85                  90                  95

Pro Ser Ser Phe Leu Leu Phe Cys Gln Asp His Tyr Ala Gln Leu Lys
                100                 105                 110

Arg Glu Asn Pro Asn Trp Ser Val Val Gln Val Ala Lys Ala Thr Gly
            115                 120                 125

Lys Met Trp Ser Thr Ala Thr Asp Leu Glu Lys His Pro Tyr Glu Gln
130                 135                 140

Arg Val Ala Leu Leu Arg Ala Lys Tyr Phe Glu Glu Leu Glu Leu Tyr
145                 150                 155                 160
```

Arg Lys Gln Cys Asn Ala Arg Lys Lys Tyr Arg Met Ser Ala Arg Asn
                165                 170                 175

Arg Ser Arg Gly Lys Arg Val Arg Gln Ser
            180                 185

<210> SEQ ID NO 61
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Ser Ser Glu Lys
        35                  40                  45

Trp Arg Ser Ile Ser Lys His Glu Lys Ala Lys Tyr Glu Ala Leu Ala
50                  55                  60

Lys Leu Asp Lys Ala Arg Tyr Gln Glu Glu Met Met Asn Tyr Val Gly
65                  70                  75                  80

Lys Arg Lys Lys Arg Lys Arg Asp Pro Gln Glu Pro Arg Arg Pro
                85                  90                  95

Pro Ser Ser Phe Leu Leu Phe Ser Gln Asp His Tyr Ala Gln Leu Lys
            100                 105                 110

Arg Glu Asn Pro Asn Trp Ser Val Val Gln Val Ala Lys Ala Thr Gly
        115                 120                 125

Lys Met Trp Ser Thr Ala Thr Asp Leu Glu Lys His Pro Tyr Glu Gln
130                 135                 140

Arg Val Ala Leu Leu Arg Ala Lys Tyr Phe Glu Glu Leu Glu Leu Tyr
145                 150                 155                 160

Arg Lys Gln Cys Asn Ala Arg Lys Lys Tyr Arg Met Ser Ala Arg Asn
                165                 170                 175

Arg Cys Arg Gly Lys Arg Val Arg Gln Ser
            180                 185

<210> SEQ ID NO 62
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Ser Ser Glu Lys
        35                  40                  45

Trp Arg Ser Ile Ser Lys His Glu Lys Ala Lys Tyr Glu Ala Leu Ala
50                  55                  60

Lys Leu Asp Lys Ala Arg Tyr Gln Glu Glu Met Met Asn Tyr Val Gly

```
                65                  70                  75                  80
Lys Arg Lys Lys Arg Arg Lys Arg Asp Pro Gln Glu Pro Arg Arg Pro
                    85                  90                  95

Pro Ser Ser Phe Leu Leu Phe Cys Gln Asp His Tyr Ala Gln Leu Lys
                    100                 105                 110

Arg Glu Asn Pro Asn Trp Ser Val Gln Val Ala Lys Ala Thr Gly
                    115                 120                 125

Lys Met Trp Ser Thr Ala Thr Asp Leu Glu Lys His Pro Tyr Glu Gln
                    130                 135                 140

Arg Val Ala Leu Leu Arg Ala Lys Tyr Phe Glu Leu Glu Leu Tyr
145                 150                 155                 160

Arg Lys Gln Ser Asn Ala Arg Lys Lys Tyr Arg Met Ser Ala Arg Asn
                    165                 170                 175

Arg Cys Arg Gly Lys Arg Val Arg Gln Ser
                    180                 185

<210> SEQ ID NO 63
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
                    20                  25                  30

Asn Thr Tyr Val Gly Phe Lys Glu Phe Ser Arg Lys Ser Ser Glu Lys
                    35                  40                  45

Trp Arg Ser Ile Ser Lys His Glu Lys Ala Lys Tyr Glu Ala Leu Ala
                    50                  55                  60

Lys Leu Asp Lys Ala Arg Tyr Gln Glu Glu Met Met Asn Tyr Val Gly
65                  70                  75                  80

Lys Arg Lys Lys Arg Arg Lys Arg Asp Pro Gln Glu Pro Arg Arg Pro
                    85                  90                  95

Pro Ser Ser Phe Leu Leu Phe Cys Gln Asp His Tyr Ala Gln Leu Lys
                    100                 105                 110

Arg Glu Asn Pro Asn Trp Ser Val Gln Val Ala Lys Ala Thr Gly
                    115                 120                 125

Lys Met Trp Ser Thr Ala Thr Asp Leu Glu Lys His Pro Tyr Glu Gln
                    130                 135                 140

Arg Val Ala Leu Leu Arg Ala Lys Tyr Phe Glu Leu Glu Leu Tyr
145                 150                 155                 160

Arg Lys Gln Cys Asn Ala Arg Lys Lys Tyr Arg Met Ser Ala Arg Asn
                    165                 170                 175

Arg Ser Arg Gly Lys Arg Val Arg Gln Ser
                    180                 185

<210> SEQ ID NO 64
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 64

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Cys Ser Glu Lys
        35                  40                  45

Trp Arg Ser Ile Ser Lys His Glu Lys Ala Lys Tyr Glu Ala Leu Ala
    50                  55                  60

Lys Leu Asp Lys Ala Arg Tyr Gln Glu Glu Met Met Asn Tyr Val Gly
65                  70                  75                  80

Lys Arg Lys Lys Arg Arg Lys Arg Asp Pro Gln Glu Pro Arg Arg Pro
                85                  90                  95

Pro Ser Ser Phe Leu Leu Phe Ser Gln Asp His Tyr Ala Gln Leu Lys
            100                 105                 110

Arg Glu Asn Pro Asn Trp Ser Val Val Gln Val Ala Lys Ala Thr Gly
        115                 120                 125

Lys Met Trp Ser Thr Ala Thr Asp Leu Glu Lys His Pro Tyr Glu Gln
    130                 135                 140

Arg Val Ala Leu Leu Arg Ala Lys Tyr Phe Glu Glu Leu Glu Leu Tyr
145                 150                 155                 160

Arg Lys Gln Ser Asn Ala Arg Lys Lys Tyr Arg Met Ser Ala Arg Asn
                165                 170                 175

Arg Cys Arg Gly Lys Arg Val Arg Gln Ser
            180                 185

<210> SEQ ID NO 65
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Cys Ser Glu Lys
        35                  40                  45

Trp Arg Ser Ile Ser Lys His Glu Lys Ala Lys Tyr Glu Ala Leu Ala
    50                  55                  60

Lys Leu Asp Lys Ala Arg Tyr Gln Glu Glu Met Met Asn Tyr Val Gly
65                  70                  75                  80

Lys Arg Lys Lys Arg Arg Lys Arg Asp Pro Gln Glu Pro Arg Arg Pro
                85                  90                  95

Pro Ser Ser Phe Leu Leu Phe Ser Gln Asp His Tyr Ala Gln Leu Lys
            100                 105                 110

Arg Glu Asn Pro Asn Trp Ser Val Val Gln Val Ala Lys Ala Thr Gly
        115                 120                 125

Lys Met Trp Ser Thr Ala Thr Asp Leu Glu Lys His Pro Tyr Glu Gln
    130                 135                 140

Arg Val Ala Leu Leu Arg Ala Lys Tyr Phe Glu Leu Glu Leu Tyr
145                 150                 155                 160

Arg Lys Gln Cys Asn Ala Arg Lys Lys Tyr Arg Met Ser Ala Arg Asn
                165                 170                 175

Arg Ser Arg Gly Lys Arg Val Arg Gln Ser
            180                 185

<210> SEQ ID NO 66
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Cys Ser Glu Lys
        35                  40                  45

Trp Arg Ser Ile Ser Lys His Glu Lys Ala Lys Tyr Glu Ala Leu Ala
50                  55                  60

Lys Leu Asp Lys Ala Arg Tyr Gln Glu Glu Met Met Asn Tyr Val Gly
65                  70                  75                  80

Lys Arg Lys Lys Arg Lys Arg Asp Pro Gln Glu Pro Arg Arg Pro
                85                  90                  95

Pro Ser Ser Phe Leu Leu Phe Cys Gln Asp His Tyr Ala Gln Leu Lys
            100                 105                 110

Arg Glu Asn Pro Asn Trp Ser Val Val Gln Val Ala Lys Ala Thr Gly
        115                 120                 125

Lys Met Trp Ser Thr Ala Thr Asp Leu Glu Lys His Pro Tyr Glu Gln
    130                 135                 140

Arg Val Ala Leu Leu Arg Ala Lys Tyr Phe Glu Glu Leu Glu Leu Tyr
145                 150                 155                 160

Arg Lys Gln Ser Asn Ala Arg Lys Lys Tyr Arg Met Ser Ala Arg Asn
                165                 170                 175

Arg Ser Arg Gly Lys Arg Val Arg Gln Ser
            180                 185

<210> SEQ ID NO 67
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Ser Ser Glu Lys
        35                  40                  45

Trp Arg Ser Ile Ser Lys His Glu Lys Ala Lys Tyr Glu Ala Leu Ala

```
                    50                  55                  60

Lys Leu Asp Lys Ala Arg Tyr Gln Glu Glu Met Met Asn Tyr Val Gly
 65                  70                  75                  80

Lys Arg Lys Lys Arg Arg Lys Arg Asp Pro Gln Glu Pro Arg Arg Pro
                     85                  90                  95

Pro Ser Ser Phe Leu Leu Phe Ser Gln Asp His Tyr Ala Gln Leu Lys
                    100                 105                 110

Arg Glu Asn Pro Asn Trp Ser Val Val Gln Val Ala Lys Ala Thr Gly
                115                 120                 125

Lys Met Trp Ser Thr Ala Thr Asp Leu Glu Lys His Pro Tyr Glu Gln
            130                 135                 140

Arg Val Ala Leu Leu Arg Ala Lys Tyr Phe Glu Glu Leu Glu Leu Tyr
145                 150                 155                 160

Arg Lys Gln Ser Asn Ala Arg Lys Lys Tyr Arg Met Ser Ala Arg Asn
                165                 170                 175

Arg Cys Arg Gly Lys Arg Val Arg Gln Ser
            180                 185

<210> SEQ ID NO 68
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Met Gly Lys Glu Ile Gln Leu Lys Pro Lys Ala Asn Val Ser Ser Tyr
  1               5                  10                  15

Val His Phe Leu Leu Asn Tyr Arg Asn Lys Phe Lys Glu Gln Gln Pro
                 20                  25                  30

Asn Thr Tyr Val Gly Phe Lys Glu Phe Ser Arg Lys Ser Ser Glu Lys
             35                  40                  45

Trp Arg Ser Ile Ser Lys His Glu Lys Ala Lys Tyr Glu Ala Leu Ala
 50                  55                  60

Lys Leu Asp Lys Ala Arg Tyr Gln Glu Glu Met Met Asn Tyr Val Gly
 65                  70                  75                  80

Lys Arg Lys Lys Arg Arg Lys Arg Asp Pro Gln Glu Pro Arg Arg Pro
                     85                  90                  95

Pro Ser Ser Phe Leu Leu Phe Ser Gln Asp His Tyr Ala Gln Leu Lys
                    100                 105                 110

Arg Glu Asn Pro Asn Trp Ser Val Val Gln Val Ala Lys Ala Thr Gly
                115                 120                 125

Lys Met Trp Ser Thr Ala Thr Asp Leu Glu Lys His Pro Tyr Glu Gln
            130                 135                 140

Arg Val Ala Leu Leu Arg Ala Lys Tyr Phe Glu Glu Leu Glu Leu Tyr
145                 150                 155                 160

Arg Lys Gln Cys Asn Ala Arg Lys Lys Tyr Arg Met Ser Ala Arg Asn
                165                 170                 175

Arg Ser Arg Gly Lys Arg Val Arg Gln Ser
            180                 185

<210> SEQ ID NO 69
<211> LENGTH: 186
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 69
```

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Ser Ser Glu Lys
        35                  40                  45

Trp Arg Ser Ile Ser Lys His Glu Lys Ala Lys Tyr Glu Ala Leu Ala
    50                  55                  60

Lys Leu Asp Lys Ala Arg Tyr Gln Glu Glu Met Met Asn Tyr Val Gly
65                  70                  75                  80

Lys Arg Lys Lys Arg Arg Lys Arg Asp Pro Gln Glu Pro Arg Arg Pro
                85                  90                  95

Pro Ser Ser Phe Leu Leu Phe Cys Gln Asp His Tyr Ala Gln Leu Lys
            100                 105                 110

Arg Glu Asn Pro Asn Trp Ser Val Val Gln Val Ala Lys Ala Thr Gly
        115                 120                 125

Lys Met Trp Ser Thr Ala Thr Asp Leu Glu Lys His Pro Tyr Glu Gln
130                 135                 140

Arg Val Ala Leu Leu Arg Ala Lys Tyr Phe Glu Glu Leu Glu Leu Tyr
145                 150                 155                 160

Arg Lys Gln Ser Asn Ala Arg Lys Lys Tyr Arg Met Ser Ala Arg Asn
                165                 170                 175

Arg Ser Arg Gly Lys Arg Val Arg Gln Ser
            180                 185

```
<210> SEQ ID NO 70
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70
```

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Cys Ser Glu Lys
        35                  40                  45

Trp Arg Ser Ile Ser Lys His Glu Lys Ala Lys Tyr Glu Ala Leu Ala
    50                  55                  60

Lys Leu Asp Lys Ala Arg Tyr Gln Glu Glu Met Met Asn Tyr Val Gly
65                  70                  75                  80

Lys Arg Lys Lys Arg Arg Lys Arg Asp Pro Gln Glu Pro Arg Arg Pro
                85                  90                  95

Pro Ser Ser Phe Leu Leu Phe Ser Gln Asp His Tyr Ala Gln Leu Lys
            100                 105                 110

Arg Glu Asn Pro Asn Trp Ser Val Val Gln Val Ala Lys Ala Thr Gly
        115                 120                 125

```
Lys Met Trp Ser Thr Ala Thr Asp Leu Glu Lys His Pro Tyr Glu Gln
            130                 135                 140

Arg Val Ala Leu Leu Arg Ala Lys Tyr Phe Glu Leu Glu Leu Tyr
145                 150                 155                 160

Arg Lys Gln Ser Asn Ala Arg Lys Lys Tyr Arg Met Ser Ala Arg Asn
            165                 170                 175

Arg Ser Arg Gly Lys Arg Val Arg Gln Ser
            180                 185
```

<210> SEQ ID NO 71
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

```
Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
            20                  25                  30

Asn Thr Tyr Val Gly Phe Lys Glu Phe Ser Arg Lys Ser Ser Glu Lys
        35                  40                  45

Trp Arg Ser Ile Ser Lys His Glu Lys Ala Lys Tyr Glu Ala Leu Ala
50                  55                  60

Lys Leu Asp Lys Ala Arg Tyr Gln Glu Glu Met Met Asn Tyr Val Gly
65                  70                  75                  80

Lys Arg Lys Lys Arg Lys Arg Asp Pro Gln Glu Pro Arg Arg Pro
            85                  90                  95

Pro Ser Ser Phe Leu Leu Phe Ser Gln Asp His Tyr Ala Gln Leu Lys
                100                 105                 110

Arg Glu Asn Pro Asn Trp Ser Val Val Gln Val Ala Lys Ala Thr Gly
            115                 120                 125

Lys Met Trp Ser Thr Ala Thr Asp Leu Glu Lys His Pro Tyr Glu Gln
            130                 135                 140

Arg Val Ala Leu Leu Arg Ala Lys Tyr Phe Glu Leu Glu Leu Tyr
145                 150                 155                 160

Arg Lys Gln Ser Asn Ala Arg Lys Lys Tyr Arg Met Ser Ala Arg Asn
            165                 170                 175

Arg Ser Arg Gly Lys Arg Val Arg Gln Ser
            180                 185
```

<210> SEQ ID NO 72
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 72

```
atgggaaaag aaatccagct aaagcctaag gcaaatgtct cttcttacgt tcactttttg      60
ctgaattaca gaaacaaatt caaggagcag cagccaaata cctatgttgg ctttaaagag     120
ttctctagaa agagttcgga aaatggaga tccatctcaa agcatgaaaa ggccaaatat      180
gaagccctgg ccaaactcga caaagcccga taccaggaag aaatgatgaa ttatgttggc     240
```

```
aagaggaaga aacggagaaa gcgggatccc caggaaccca gacggcctcc atcatccttc        300
ctactcttct gccaagacca ctatgctcag ctgaagaggg agaacccgaa ctggtcggtg        360
gtgcaggtgg ccaaggccac agggaagatg tggtcaacag cgacagacct ggagaagcac        420
ccttatgagc aaagagtggc tctcctgaga gctaagtact tcgaggaact tgaactctac        480
cgtaaacatg taatgccagg aagaagtacc gaatgtcagc tagaaaccgg tgcagaggga        540
aaagagtcag gcagagctga                                                     560

<210> SEQ ID NO 73
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
atgggaaaag aaatccagct aaagcctaag gcaaatgtct cttcttacgt tcactttttg         60
ctgaattaca gaaacaaatt caaggagcag cagccaaata cctatgttgg ctttaaagag        120
ttctctagaa agtgttcgga aaaatggaga tccatctcaa agcatgaaaa ggccaaatat        180
gaagccctgg ccaaactcga caaagcccga taccaggaag aaatgatgaa ttatgttggc        240
aagaggaaga aacggagaaa gcgggatccc caggaaccca gacggcctcc atcatccttc        300
ctactcttca gtcaagacca ctatgctcag ctgaagaggg agaacccgaa ctggtcggtg        360
gtgcaggtgg ccaaggccac agggaagatg tggtcaacag cgacagacct ggagaagcac        420
ccttatgagc aaagagtggc tctcctgaga gctaagtact tcgaggaact tgaactctac        480
cgtaaacatg taatgccagg aagaagtacc gaatgtcagc tagaaaccgg tgcagaggga        540
aaagagtcag gcagagctga                                                     560

<210> SEQ ID NO 74
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
atgggaaaag aaatccagct aaagcctaag gcaaatgtct cttcttacgt tcactttttg         60
ctgaattaca gaaacaaatt caaggagcag cagccaaata cctatgttgg ctttaaagag        120
ttctctagaa agtgttcgga aaaatggaga tccatctcaa agcatgaaaa ggccaaatat        180
gaagccctgg ccaaactcga caaagcccga taccaggaag aaatgatgaa ttatgttggc        240
aagaggaaga aacggagaaa gcgggatccc caggaaccca gacggcctcc atcatccttc        300
ctactcttct gccaagacca ctatgctcag ctgaagaggg agaacccgaa ctggtcggtg        360
gtgcaggtgg ccaaggccac agggaagatg tggtcaacag cgacagacct ggagaagcac        420
ccttatgagc aaagagtggc tctcctgaga gctaagtact tcgaggaact tgaactctac        480
cgtaaacaag taatgccagg aagaagtacc gaatgtcagc tagaaaccgg tgcagaggga        540
aaagagtcag gcagagctga                                                     560

<210> SEQ ID NO 75
```

```
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
atgggaaaag aaatccagct aaagcctaag gcaaatgtct cttcttacgt tcactttttg      60
ctgaattaca gaaacaaatt caaggagcag cagccaaata cctatgttgg ctttaaagag     120
ttctctagaa agtgttcgga aaatggaga tccatctcaa agcatgaaaa ggccaaatat      180
gaagccctgg ccaaactcga caaagcccga taccaggaag aaatgatgaa ttatgttggc     240
aagaggaaga acggagaaa gcgggatccc caggaaccca gacggcctcc atcatccttc      300
ctactcttct gccaagacca ctatgctcag ctgaagaggg agaacccgaa ctggtcggtg     360
gtgcaggtgg ccaaggccac agggaagatg tggtcaacag cgacagacct ggagaagcac     420
ccttatgagc aaagagtggc tctcctgaga gctaagtact tcgaggaact tgaactctac     480
cgtaaacatg taatgccagg aagaagtacc gaatgtcagc tagaaaccgg agcagaggga     540
aaagagtcag gcagagctga                                                 560

<210> SEQ ID NO 76
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76
atgggaaaag aaatccagct aaagcctaag gcaaatgtct cttcttacgt tcactttttg      60
ctgaattaca gaaacaaatt caaggagcag cagccaaata cctatgttgg ctttaaagag     120
ttctctagaa agagttcgga aaatggaga tccatctcaa agcatgaaaa ggccaaatat      180
gaagccctgg ccaaactcga caaagcccga taccaggaag aaatgatgaa ttatgttggc     240
aagaggaaga acggagaaa gcgggatccc caggaaccca gacggcctcc atcatccttc      300
ctactcttca gtcaagacca ctatgctcag ctgaagaggg agaacccgaa ctggtcggtg     360
gtgcaggtgg ccaaggccac agggaagatg tggtcaacag cgacagacct ggagaagcac     420
ccttatgagc aaagagtggc tctcctgaga gctaagtact tcgaggaact tgaactctac     480
cgtaaacatg taatgccagg aagaagtacc gaatgtcagc tagaaaccgg tgcagaggga     540
aaagagtcag gcagagctga                                                 560

<210> SEQ ID NO 77
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77
atgggaaaag aaatccagct aaagcctaag gcaaatgtct cttcttacgt tcactttttg      60
ctgaattaca gaaacaaatt caaggagcag cagccaaata cctatgttgg ctttaaagag     120
ttctctagaa agagttcgga aaatggaga tccatctcaa agcatgaaaa ggccaaatat      180
```
gaagccctgg ccaaactcga caaagcccga taccaggaag aaatgatgaa ttatgttggc    240
aagaggaaga aacggagaaa gcgggatccc caggaaccca gacggcctcc atcatccttc    300
ctactcttct gccaagacca ctatgctcag ctgaagaggg agaacccgaa ctggtcggtg    360
gtgcaggtgg ccaaggccac agggaagatg tggtcaacag cgacagacct ggagaagcac    420
ccttatgagc aaagagtggc tctcctgaga gctaagtact tcgaggaact tgaactctac    480
cgtaaacaag taatgccagg aagaagtacc gaatgtcagc tagaaaccgg tgcagaggga    540
aaagagtcag gcagagctga                                               560

<210> SEQ ID NO 78
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
atgggaaaag aaatccagct aaagcctaag gcaaatgtct cttcttacgt tcacttttttg    60 ctgaattaca gaaacaaatt caaggagcag cagccaaata cctatgttgg ctttaaagag   120
ttctctagaa agagttcgga aaatggaga tccatctcaa agcatgaaaa ggccaaatat    180
gaagccctgg ccaaactcga caaagcccga taccaggaag aaatgatgaa ttatgttggc    240
aagaggaaga aacggagaaa gcgggatccc caggaaccca gacggcctcc atcatccttc    300
ctactcttct gccaagacca ctatgctcag ctgaagaggg agaacccgaa ctggtcggtg    360
gtgcaggtgg ccaaggccac agggaagatg tggtcaacag cgacagacct ggagaagcac    420
ccttatgagc aaagagtggc tctcctgaga gctaagtact tcgaggaact tgaactctac    480
cgtaaacatg taatgccagg aagaagtacc gaatgtcagc tagaaaccgg agcagaggga    540
aaagagtcag gcagagctga                                               560

<210> SEQ ID NO 79
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79
atgggaaaag aaatccagct aaagcctaag gcaaatgtct cttcttacgt tcactttttg     60
ctgaattaca gaaacaaatt caaggagcag cagccaaata cctatgttgg ctttaaagag   120
ttctctagaa agtgttcgga aaatggaga tccatctcaa agcatgaaaa ggccaaatat    180
gaagccctgg ccaaactcga caaagcccga taccaggaag aaatgatgaa ttatgttggc    240
aagaggaaga aacggagaaa gcgggatccc caggaaccca gacggcctcc atcatccttc    300
ctactcttca gtcaagacca ctatgctcag ctgaagaggg agaacccgaa ctggtcggtg    360
gtgcaggtgg ccaaggccac agggaagatg tggtcaacag cgacagacct ggagaagcac    420
ccttatgagc aaagagtggc tctcctgaga gctaagtact tcgaggaact tgaactctac    480
cgtaaacaag taatgccagg aagaagtacc gaatgtcagc tagaaaccgg tgcagaggga    540
aaagagtcag gcagagctga                                               560

<210> SEQ ID NO 80
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 80

```
atgggaaaag aaatccagct aaagcctaag gcaaatgtct cttcttacgt tcactttttg      60
ctgaattaca gaaacaaatt caaggagcag cagccaaata cctatgttgg ctttaaagag     120
ttctctagaa agtgttcgga aaaatggaga tccatctcaa agcatgaaaa ggccaaatat     180
gaagccctgg ccaaactcga caaagcccga taccaggaag aaatgatgaa ttatgttggc     240
aagaggaaga aacggagaaa gcgggatccc caggaaccca gacggcctcc atcatccttc     300
ctactcttca gtcaagacca ctatgctcag ctgaagaggg agaacccgaa ctggtcggtg     360
gtgcaggtgg ccaaggccac agggaagatg tggtcaacag cgacagacct ggagaagcac     420
ccttatgagc aaagagtggc tctcctgaga gctaagtact tcgaggaact tgaactctac     480
cgtaaacatg taatgccagg aagaagtacc gaatgtcagc tagaaaccgg agcagaggga     540
aaagagtcag gcagagctga                                                 560
```

<210> SEQ ID NO 81
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
atgggaaaag aaatccagct aaagcctaag gcaaatgtct cttcttacgt tcactttttg      60
ctgaattaca gaaacaaatt caaggagcag cagccaaata cctatgttgg ctttaaagag     120
ttctctagaa agtgttcgga aaaatggaga tccatctcaa agcatgaaaa ggccaaatat     180
gaagccctgg ccaaactcga caaagcccga taccaggaag aaatgatgaa ttatgttggc     240
aagaggaaga aacggagaaa gcgggatccc caggaaccca gacggcctcc atcatccttc     300
ctactcttct gccaagacca ctatgctcag ctgaagaggg agaacccgaa ctggtcggtg     360
gtgcaggtgg ccaaggccac agggaagatg tggtcaacag cgacagacct ggagaagcac     420
ccttatgagc aaagagtggc tctcctgaga gctaagtact tcgaggaact tgaactctac     480
cgtaaacaag taatgccagg aagaagtacc gaatgtcagc tagaaaccgg agcagaggga     540
aaagagtcag gcagagctga                                                 560
```

<210> SEQ ID NO 82
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 82

```
atgggaaaag aaatccagct aaagcctaag gcaaatgtct cttcttacgt tcactttttg      60
ctgaattaca gaaacaaatt caaggagcag cagccaaata cctatgttgg ctttaaagag     120
```
ttctctagaa agagttcgga aaaatggaga tccatctcaa agcatgaaaa ggccaaatat    180
gaagccctgg ccaaactcga caaagcccga taccaggaag aaatgatgaa ttatgttggc    240
aagaggaaga aacggagaaa gcgggatccc caggaaccca gacggcctcc atcatccttc    300
ctactcttca gtcaagacca ctatgctcag ctgaagaggg agaacccgaa ctggtcggtg    360
gtgcaggtgg ccaaggccac agggaagatg tggtcaacag cgacagacct ggagaagcac    420
ccttatgagc aaagagtggc tctcctgaga gctaagtact tcgaggaact tgaactctac    480
cgtaaacaag taatgccagg aagaagtacc gaatgtcagc tagaaaccgg tgcagaggga    540
aaagagtcag gcagagctga                                                560

<210> SEQ ID NO 83
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
atgggaaaag aaatccagct aaagcctaag gcaaatgtct cttcttacgt tcacttttg     60 ctgaattaca gaaacaaatt caaggagcag cagccaaata cctatgttgg ctttaaagag    120
ttctctagaa agagttcgga aaaatggaga tccatctcaa agcatgaaaa ggccaaatat    180
gaagccctgg ccaaactcga caaagcccga taccaggaag aaatgatgaa ttatgttggc    240
aagaggaaga aacggagaaa gcgggatccc caggaaccca gacggcctcc atcatccttc    300
ctactcttca gtcaagacca ctatgctcag ctgaagaggg agaacccgaa ctggtcggtg    360
gtgcaggtgg ccaaggccac agggaagatg tggtcaacag cgacagacct ggagaagcac    420
ccttatgagc aaagagtggc tctcctgaga gctaagtact tcgaggaact tgaactctac    480
cgtaaacatg taatgccagg aagaagtacc gaatgtcagc tagaaaccgg agcagaggga    540
aaagagtcag gcagagctga                                                560

<210> SEQ ID NO 84
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
atgggaaaag aaatccagct aaagcctaag gcaaatgtct cttcttacgt tcacttttg     60 ctgaattaca gaaacaaatt caaggagcag cagccaaata cctatgttgg ctttaaagag    120
ttctctagaa agagttcgga aaaatggaga tccatctcaa agcatgaaaa ggccaaatat    180
gaagccctgg ccaaactcga caaagcccga taccaggaag aaatgatgaa ttatgttggc    240
aagaggaaga aacggagaaa gcgggatccc caggaaccca gacggcctcc atcatccttc    300
ctactcttct gccaagacca ctatgctcag ctgaagaggg agaacccgaa ctggtcggtg    360
gtgcaggtgg ccaaggccac agggaagatg tggtcaacag cgacagacct ggagaagcac    420
ccttatgagc aaagagtggc tctcctgaga gctaagtact tcgaggaact tgaactctac    480
cgtaaacaag taatgccagg aagaagtacc gaatgtcagc tagaaaccgg agcagaggga    540

-continued

```
aaagagtcag gcagagctga                                          560

<210> SEQ ID NO 85
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
atgggaaaag aaatccagct aaagcctaag gcaaatgtct cttcttacgt tcactttttg    60
ctgaattaca gaaacaaatt caaggagcag cagccaaata cctatgttgg ctttaaagag   120
ttctctagaa agtgttcgga aaaatggaga tccatctcaa agcatgaaaa ggccaaatat   180
gaagccctgg ccaaactcga caaagcccga taccaggaag aaatgatgaa ttatgttggc   240
aagaggaaga aacggagaaa gcgggatccc caggaaccca gacggcctcc atcatccttc   300
ctactcttca gtcaagacca ctatgctcag ctgaagaggg agaacccgaa ctggtcggtg   360
gtgcaggtgg ccaaggccac agggaagatg tggtcaacag cgacagacct ggagaagcac   420
ccttatgagc aaagagtggc tctcctgaga gctaagtact tcgaggaact tgaactctac   480
cgtaaacaag taatgccagg aagaagtacc gaatgtcagc tagaaaccgg agcagaggga   540
aaagagtcag gcagagctga                                              560

<210> SEQ ID NO 86
<211> LENGTH: 560
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
atgggaaaag aaatccagct aaagcctaag gcaaatgtct cttcttacgt tcactttttg    60
ctgaattaca gaaacaaatt caaggagcag cagccaaata cctatgttgg ctttaaagag   120
ttctctagaa agagttcgga aaaatggaga tccatctcaa agcatgaaaa ggccaaatat   180
gaagccctgg ccaaactcga caaagcccga taccaggaag aaatgatgaa ttatgttggc   240
aagaggaaga aacggagaaa gcgggatccc caggaaccca gacggcctcc atcatccttc   300
ctactcttca gtcaagacca ctatgctcag ctgaagaggg agaacccgaa ctggtcggtg   360
gtgcaggtgg ccaaggccac agggaagatg tggtcaacag cgacagacct ggagaagcac   420
ccttatgagc aaagagtggc tctcctgaga gctaagtact tcgaggaact tgaactctac   480
cgtaaacaag taatgccagg aagaagtacc gaatgtcagc tagaaaccgg agcagaggga   540
aaagagtcag gcagagctga                                              560
```

COMPOSITION AND METHODS FOR DISRUPTION OF BACTERIAL BIOFILMS WITHOUT ACCOMPANYING INFLAMMATION

CROSS REFERENCE TO RELATED APPLICATION

This application is a National Stage Application of PCT/US2018/022508, filed Mar. 14, 2018, which claims the benefit under 35 U.S.C. § 119(e) to U.S. Provisional Application No. 62/471,834, filed Mar. 15, 2017, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 29, 2018, is named 106887-0961_SL.txt and is 139,022 bytes in size.

BACKGROUND

Bacteria persisting in a biofilm in the human body cause about two-thirds of all chronic/recurrent diseases. These biofilms are comprised of bacteria protected by an outer "slime" that is often comprised primarily of DNA which prevents the innate and adaptive immune systems, antibiotics and other antibacterial agents from gaining access to the bacteria inside the biofilm. Biofilms make it extremely difficult to clear the infection from the body. Furthermore, biofilms can act as a reservoir for future acute infections often with lethal consequences.

At least one protein from the DNABII family of proteins is found in all known eubacteria and are naturally found outside of the bacterial cell. While they elicit a strong innate immune response, host subjects fail to naturally produce specific antibody to family members as a result of infection. The major problem with bacterial biofilms is the inability of the host immune system and/or antibiotics and other antimicrobials to gain access to the bacteria protected within the biofilm.

Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes which impede filters and orifices. Biofilm and biofilm organisms also cause corrosion of pipeline and petroleum process equipment. These problems can be manifested throughout an oil or gas production facility to the point where fouling and corrosive biofilm organisms have even been found on the surfaces of final product storage tanks.

In the home, biofilms are found in or on any surface that supports microbial growth, e.g., in drains, on food preparation surfaces, in toilets and in swimming pools and spas.

Biofilms are implicated in a wide range of water processes, both domestic and industrial. They can grow on the surface of process equipment and impede the performance of the equipment, such as degradation of heat transfer or plugging of filters and membranes. Biofilms growing on cooling tower fill can add enough weight to cause collapse of the fill. Biofilms cause corrosion of even highly specialized stainless steels. Biofilms in a water process can degrade the value of a final product. Biofilms growing in drinking water distribution systems can harbor potential pathogenic organisms, corrosive organisms or bacteria that degrade the aesthetic quality of the water.

Thus, a need exists to break through the protective barrier of biofilms to treat or kill the associated bacterial infections and clear them from surfaces and in water systems. This invention satisfies this need and provides related advantages as well.

SUMMARY

HMGB1, a eukyotic protein, was discovered as a non-histone chromatin protein, four decades ago (Goodwin et al. 1973). HMGB1 is a ubiquitously expressed nuclear protein that functions as a structural component in a gamut of nucleoprotein interactions including DNA replication, repair and gene regulation by virtue of its ability to bind DNA. It also facilitates protein-protein interactions in various cancers, autophagy (Tang et al. 2011), and non-canonical secretory pathway (Lee et al. 2010). Although HMGB1 is primarily in the nucleus, it can be secreted and/or released into the extracellular space by several cell types including activated immune cells (macrophages, monocytes, neutrophils, dendritic cells and natural killer cells), epithelial cells and fibroblasts (Yang et al. 2007). Extracellular HMGB1 exhibits cytokine-inducing, chemokine-like and proangiogenic functions (Melloni et al. 1995a; 1995b; Pistoia and Raffaghello 2011) (Ranzato et al. 2009) (Abraham et al. 2000; Agnello et al. 2002) (Mardente et al. 2012) (Wang et al. 1999). It also participates in bacterial killing (Gong et al. 2009; Zetterstrom et al. 2006), and cellular senescence (Davalos et al. 2013). HMGB1 is associated with Neutrophil extracellular traps (NETs) released by neutrophils to combat microbial infection.

Antibiotics are the first line of treatment for bacterial infections. Biofilm is a necessary component of approximately 80% of all bacterial infections and is strongly implicated in the chronic and recurrent nature of infectious diseases. Also, bacteria in a biofilm are up to a 1000-fold more resistant to antibiotics. The chronic and recurrent nature of biofilm-mediated bacterial infections demand excessive use of antibiotics that, in turn, has led to the sobering emergence of multiple antibiotic resistant bacteria. This confounding collateral damage as a consequence of excessive use of antibiotics results in failure of antibiotic therapy and difficulty/inability to treat infections. Also, the major side effect of antibiotics is that it negatively impacts the commensal microbiota which can result in secondary infections.

HMGB1 has two tandem DNA binding domains (A and B box) and a highly acidic C-terminal tail. HMGB1 functions as a monomer and employs the two tandem DNA binding domains to bind in the DNA minor groove and bend DNA. HMGB1 also has a C-terminal domain consisting of ~30 acidic amino acid residues that possesses antimicrobial activity on bacteria in the planktonic state (Gong et al. 2009). Applicants have previously demonstrated that DNABII proteins that bind to and bend DNA are integral to the structure of biofilms formed by multiple human pathogens (Brandstetter et al. 2013; Brockson et al. 2014; Devaraj et al. 2015; Freire et al. 2016; Goodman et al. 2011; Gustave et al. 2013; Idicula et al. 2016; Justice et al. 2012; Novotny et al. 2013a; Novotny et al. 2016; Rocco et al. 2016). HMGB1 shares no sequence or structural homology to DNABII proteins, yet has been shown to replace DNABII proteins in vitro for several bacterial functions (Paull et al.

1993; Segall et al. 1994). Applicants have demonstrated that while the DNABII proteins stabilize the eDNA dependent extracellular matrix of biofilms, recombinant HMGB1 (rHMGB1) disrupts in vitro preformed bacterial biofilms (Table 1), clear NTHI biofilms from the chinchilla middle ear in an experimental model of otitis media (OM) (FIGS. 1A-1B) and inhibit *Burkholderia cenocepacia* biofilm development in the murine airways that directly resulted in reduced bacterial burden (FIGS. 2A-2D).

Although rHMGB1 was demonstrated to be effective at disrupting biofilms in vitro and in vivo, it is also well documented to induce a robust inflammatory response that can potentially be detrimental to the host. Several post-translational modifications (PTMs) including acetylation, phosphorylation, methylation, glycosylation, ADP-ribosylation, and oxidation of cysteine residues have been described for HMGB1 that modulate its location (nucleus, cytoplasm or extracellular), function, and ability to bind DNA (reviewed in (Kang et al. 2014)). Human HMGB1 contains three cysteine residues at positions 23, 45, and 106 and the oxidation of the cysteine residues impacts its inflammatory properties (Kazama et al. 2008). While HMGB1 containing C106 thiol group and a C23-C45 disulfide bond triggers inflammation, terminally oxidized cysteines promote inflammation resolution (Yang et al. 2012).

Aspects disclosed herein relate to a modified high mobility group-box 1 domain comprising one or more or all substitutions selected from the group of C23S, C45S, and C106S, an isolated or recombinant polynucleotide encoding the modified high mobility group-box 1 domain, a vector comprising the isolated or recombinant polynucleotide, and a composition comprising an effective amount of the modified high mobility group-box 1 domain and/or the aforementioned isolated or recombinant polynucleotide and/or the aforementioned vector. In some embodiments, the modified high mobility group-box 1 domain comprises the substitution C45S. In some embodiments, the modified high mobility group-box 1 domain comprises the substitutions C23S, C45S, and C106S.

Applicants demonstrate herein that C45S recombinant HMGB1 or Modified HMGB1 (C45S) ("mHMGB1 (C45S)") has been shown to disrupt pre-existing biofilms both in vitro and in vivo (in two mammalian models). Dispersal of large amount of bacteria from a biofilm into a planktonic state in vivo could have potential disadvantages in that now these planktonic bacteria may be able to gain access to other sites that they did not have access to before resulting in potential second site infections. Also, this dispersal effect could result in sepsis. None of these consequences has been observed with mHMGB1 and there are means to avoid these potential limitations in addition to the fact that depending on the site of the biofilm infection, these potential pitfalls may be moot.

Further aspects relate to a method for inhibiting, competing or titrating the binding of a deoxyribonucleic acid B II (DNABII) polypeptide to a microbial DNA in a biofilm, comprising or alternatively consisting essentially of, or yet further consisting of contacting the microbial DNA in the biofilm with an effective amount of an isolated or recombinant polypeptide comprising a modified high mobility group-box 1 domain comprising one or more substitutions selected from the group of C23S, C45S, and C106S or any one or more of the compositions disclosed above thereby inhibiting, competing or titrating the binding of the DNABII polypeptide to the microbial DNA. In some embodiments, the modified high mobility group-box 1 domain comprises the substitution C45S. In some embodiments, the modified high mobility group-box 1 domain comprises one or more or all of the substitutions C23S, C45S, and C106S. In some embodiments, the contacting is in vitro or in vivo. In some embodiments, the biofilm is formed by *Burkholderia cenocepacia, Enterobacter* spp., *Staphylococcus aureus, Klebsiella pneumoniae, Acinetobacter baumanii, Pseudomonas aeruginosa, Enterococcus faecium,* Uropathogenic *Escherichia coli* (UPEC), Non-typeable *Haemophilus influenzae* (NTHI), *Aggregatibacter actinomycetemcomitans*. In some embodiments, the method further comprises or alternatively consists essentially of, or yet further consists of administering to a subject in need thereof or optionally coating, the surface with an effective amount of an antibiotic.

Still further aspects relate to a method of preventing formation of a biofilm on a surface, comprising, or alternatively consisting essentially of, or yet further consisting of contacting, optionally coating, the surface with an effective amount of an isolated or recombinant polypeptide comprising a modified high mobility group-box 1 domain comprising one or more substitutions selected from the group of C23S, C45S, and C106S or any one or more of the compositions disclosed above thereby inhibiting, competing or titrating the binding of a DNABII polypeptide to a microbial DNA during biofilm formation. In some embodiments, the modified high mobility group-box 1 domain comprises the substitution C45S. In some embodiments, the modified high mobility group-box 1 domain comprises the substitutions C23S, C45S, and C106S. In some embodiments, the biofilm is formed by *Burkholderia cenocepacia, Enterobacter* spp., *Staphylococcus aureus, Klebsiella pneumoniae, Acinetobacter baumanii, Pseudomonas aeruginosa, Enterococcus faecium,* Uropathogenic *Escherichia coli* (UPEC), Non-typeable *Haemophilus influenzae* (NTHI), *Aggregatibacter actinomycetemcomitans*. In some embodiments, the method further comprises or alternatively consists essentially of, or yet further consists of administering, optionally coating, the surface with an effective amount of an antibiotic.

Additional aspects relate to a method for preventing or treating a microbial infection in a subject that produces a biofilm, comprising or alternatively consisting essentially of, or yet further consisting of administering an effective amount of an isolated or recombinant polypeptide comprising a modified high mobility group-box 1 domain comprising one or more substitutions selected from the group of C23S, C45S, and C106S or any one or more of the compositions disclosed above thereby inhibiting, competing or titrating the binding of a DNABII polypeptide to a microbial DNA. In some embodiments, the modified high mobility group-box 1 domain comprises the substitution C45S. In some embodiments, the modified high mobility group-box 1 domain comprises the substitutions C23S, C45S, and C106S. In some embodiments, the biofilm is formed by *Burkholderia cenocepacia, Enterobacter* spp., *Staphylococcus aureus, Klebsiella pneumoniae, Acinetobacter baumanii, Pseudomonas aeruginosa, Enterococcus faecium,* Uropathogenic *Escherichia coli* (UPEC), Non-typeable *Haemophilus influenzae* (NTHI), *Aggregatibacter actinomycetemcomitans*. In some embodiments, the method further comprises or alternatively consist essentially of, or yet further consists of administering, an effective amount of an antibiotic.

It is appreciated that among the equivalents to a modified high mobility group-box 1 domain are modified high mobility group-box 2, modified high mobility group-box 3, and modified high mobility group-box 4 comprising cysteine to serine substitutions at one or more amino acid positions corresponding to C23S, C45S, and C106S of a modified high mobility group box 1. For modified high mobility group-box 2 the corresponding cysteine residues are found at position 23, 45, and 106; for modified high mobility group-box 3 the corresponding cysteine residues are found at position 23, 45, and 104; and for modified high mobility group-box 4 the corresponding cysteine residues are found at position 45, 104, 164, and 178. Thus, Applicants believe the aforementioned aspects disclosed with respect to a modified high mobility group-box 1 comprising one or more substitutions selected from the group of C23S, C45S, and C106S are equally applicable to the aforementioned high mobility group-box species with one or more cysteine to serine substitutions at the mentioned positions, e.g. a modified high mobility group-box 2 comprising one or more substitutions selected from the group of C23S, C45S, and C106S; a modified high mobility group-box 3 comprising one or more substitutions selected from the group of C23S, C45S, and C104S; and a modified high mobility group-box 4 comprising one or more substitutions selected from the group of C45S, C104S, C164S, and C178S.

BRIEF DESCRIPTION OF THE DRAWINGS

(FIG. 2D) Lungs were collected 72 hpi. Tissue was fixed and embedded in paraffin, sectioned and stained with H&E. All panels show a magnification of 10×. Note that mHMGB1 (C45S) treatment resulted in significant decreases in B. cenocepacia CFUs and inflammatory cell infiltration in vivo compared to rHMGB1.

FIG. 7 shows that mHMGB1 (C45 S) promotes bacterial clearance but does not increase airway inflammation in mice infected with B. cenocepacia. C57BL/6 mice were infected with $10^7$ CFU i.t., and simultaneously received 5 mg rHMGB1 or mHMGB1 (C45 S). (FIG. 7A) Aggregates of B. cenocepacia were visible by fluorescence microscopy in sections probed with an α-B. cenocepacia antibody. After 18 h, (FIG. 7B) CFUs were quantified in BAL, and (FIG. 7C) BAL cells were stained with α-CD45, CD11b, and Ly-6G to measure neutrophil migration. Bars represent SD. *$P<0.05$. (FIG. 7D) Lung tissue collected 72 hpi was fixed and embedded in paraffin, sectioned and stained with H&E. 10× magnification. mHMGB1 (C45 S) treatment resulted in significant decreases in B. cenocepacia CFUs and inflammatory cell infiltration in vivo compared to rHMGB1.

DETAILED DESCRIPTION

Definitions

Figure 1A:
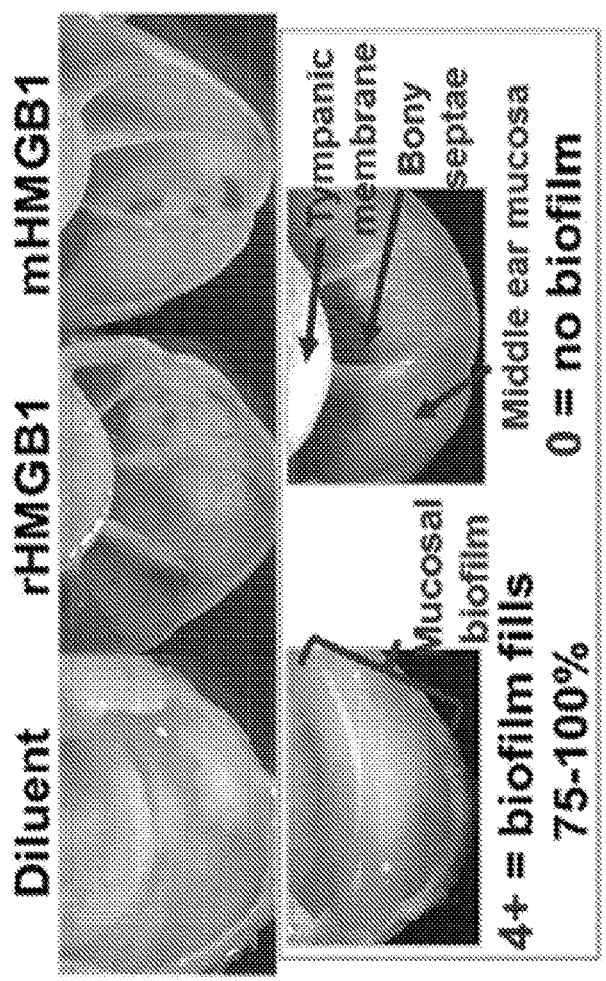
FIGS. 1A-1B show that rHMGB1 and mHMGB1 (C45S) promote bacterial clearance in an established experimental OM animal model. Diluent, 5 μg rHMGB1, or 5 mHMGB1 (C45S) were delivered directly to the middle ears of chinchillas at 4 and 5 days post infection with NTHI. Animals were sacrificed 24 h later and their middle ears were imaged (FIG. 1A) and blindly scored (FIG. 1B) based on the criteria described in the bottom of FIG. 1A. Bars represent SEM. ***$P<0.001$. Images and scoring demonstrate HMGB1 was able to clear pre-formed NTHI biofilms in vivo.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All technical and patent publications cited herein are incorporated herein by reference in their entirety. Nothing herein is to be construed as an admission that the invention is not entitled to antedate such disclosure by virtue of prior invention. See, e.g., Green and Sambrook eds. (2012) Molecular Cloning: A Laboratory Manual, 4$^{th}$ edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press);

MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, $6^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (IRL Press (1986)); Grandi ed. (2007) In Vitro Transcription and Translation Protocols, $2^{nd}$ edition; Guisan ed. (2006) Immobilization of Enzymes and Cells; Perbal (1988) A Practical Guide to Molecular Cloning, $2^{nd}$ edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, $4^{th}$ edition; and Herzenberg et al. eds (1996) Weir's Handbook of Experimental Immunology, $5^{th}$ edition; and the more recent editions each thereof available at the time of filing.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention. Embodiments defined by each of these transition terms are within the scope of this invention.

A "biofilm" intends a thin layer or an organized community of microorganisms that at times can adhere to the surface of a structure, that may be organic or inorganic, together with the polymers, such as DNA, that they secrete and/or release. The biofilms are very resistant to microbiotics and antimicrobial agents. They live on gingival tissues, teeth and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control estimate that over 65% of nosocomial (hospital-acquired) infections are caused by biofilms. Fungal biofilms also frequently contaminate medical devices. They cause chronic vaginal infections and lead to life-threatening systemic infections in people with hobbled immune systems. Biofilms also are involved in numerous diseases. For instance, cystic fibrosis patients have *Pseudomonas* infections that often result in antibiotic resistant biofilms.

A "DNABII polypeptide or protein" intends a DNA binding protein or polypeptide that is composed of DNA-binding domains and thus have a specific or general affinity for DNA. In one aspect, they bind DNA in the minor grove. Non-limiting examples of DNABII proteins are an integration host factor (IHF) protein and a histone-like protein from *E. coli* strain U93 (HU). Other DNA binding proteins that can be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813).

An "integration host factor" or "IHF" protein is a bacterial protein that is used by bacteriophages to incorporate their DNA into the host bacteria. These are DNA binding proteins that function in genetic recombination as well as in transcription and translational regulation. They also bind extracellular microbial DNA. The genes that encode the IHF protein subunits in *E. coli* are himA (Genbank accession No.: POA6X7.1) and himD (POA6Y1.1) genes.

"HU" or "histone-like protein from *E. coli* strain U93" refers to a class of heterodimeric proteins typically associated with *E. coli*. HU proteins are known to bind DNA junctions. Related proteins have been isolated from other microorganisms. The complete amino acid sequence of *E. coli* HU was reported by Laine et al. (1980) Eur. J. Biochem. 103(3):447-481. Antibodies to the HU protein are commercially available from Abcam.

"Microbial DNA" intends single or double stranded DNA from a microorganism that produces a biofilm.

"Inhibiting, preventing or breaking down" a biofilm intends the prophylactic or therapeutic reduction in the structure of a biofilm. In one aspect, the terms "inhibiting, competing or titrating" intend a reduction in the formation of the DNA/protein matrix (for example as shown in FIG. 1) that is a component of a microbial biofilm.

A "bent polynucleotide" intends a double strand polynucleotide that contains a small loop on one strand which does not pair with the other strand and any polynucleotide where the end to end distance is reduced beyond natural thermal fluctuations, i.e., that is bending beyond the persistence length of 150 bp for native B-form double stranded DNA. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9 or 10 bases.

A "subject" of diagnosis or treatment is a cell or an animal such as a mammal or a human. Non-human animals subject to diagnosis or treatment and are those subject to infections or animal models, for example, simians, murines, such as, rats, mice, chinchilla, canine, such as dogs, leporids, such as rabbits, livestock, sport animals and pets.

The term "protein", "peptide" and "polypeptide" are used interchangeably and in their broadest sense refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. The 20 amino acids found naturally in the human body shown in the table below with each of their three letter abbreviations, one letter abbreviations, structures, and corresponding codons:

| | | | | |
|---|---|---|---|---|
| non-polar, aliphatic residues | | | | |
| Glycine | Gly | G | 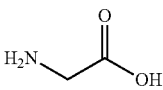 | GGU GGC GGA GGG |
| Alanine | Ala | A | 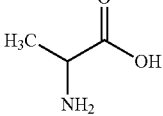 | GCU GCC GCA GCG |
| Valine | Val | V | 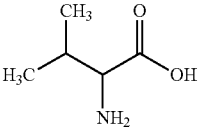 | GUU GUC GUA GUG |
| Leucine | Leu | L | 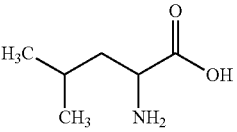 | UUA UUG CUU CUC CUA CUG |
| Isoleucine | Ile | I | 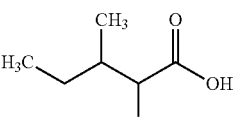 | AUU AUC AUA |
| Proline | Pro | P | 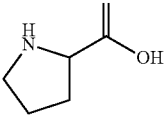 | CCU CCC CCA CCG |
| aromatic residues | | | | |
| Phenylalanine | Phe | F | 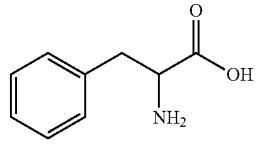 [SMILES: NC(Cc1ccccc1)C(=O)O] | UUU UUC |
| Tyrosine | Tyr | Y | 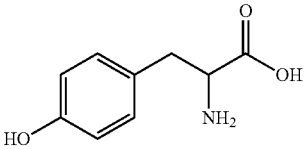 [SMILES: NC(Cc1ccc(O)cc1)C(=O)O] | UAU UAC |
| Tryptophan | Trp | W | 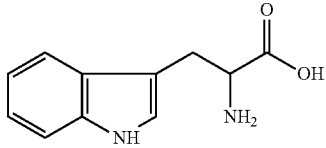 [SMILES: NC(Cc1c[nH]c2ccccc12)C(=O)O] | UGG |

-continued

| | | | | |
|---|---|---|---|---|
| polar, non-charged residues | | | | |
| Serine | Ser | S | 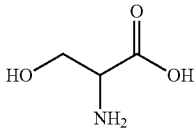 | UCU UCC UCA UCG AGU AGC |
| Threonine | Thr | T | 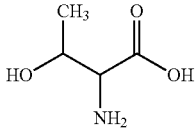 | ACU ACC ACA ACG |
| Cysteine | Cys | C | 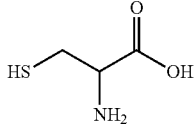 | UGU UGC |
| Methionine | Met | M | 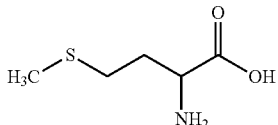 | AUG |
| Asparagine | Asn | N | 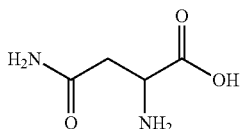 | AAU AAC |
| Glutamine | Gln | Q | 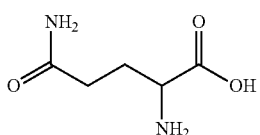 | CAA CAG |

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

The terms "equivalent" or "biological equivalent" are used interchangeably when referring to a particular molecule, biological, or cellular material and intend those having minimal homology while still maintaining desired structure or functionality.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or alternatively about 80% homology or identity and alternatively, at least about 85%, or alternatively at least about 90%, or alternatively at least about 95% or alternatively 98% percent homology or identity and exhibits substantially equivalent biological activity to the reference protein, polypeptide or nucleic acid. In another aspect, the term intends a polynucleotide that hybridizes under conditions of high stringency to the reference polynucleotide or its complement.

A polynucleotide or polynucleotide region (or a polypeptide or polypeptide region) having a certain percentage (for example, 80%, 85%, 90% or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 30% identity or alternatively less than 25% identity, less than 20% identity, or alternatively less than 10% identity with one of the sequences of the present invention.

"Homology" or "identity" or "similarity" can also refer to two nucleic acid molecules that hybridize under stringent conditions to the reference polynucleotide or its complement.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," "treatment" and the like are used herein to mean obtaining a desired pharmacologic and/or physiologic effect. The effect may be prophylactic in terms of completely or partially preventing a disorder or sign or symptom thereof and/or may be therapeutic in terms of a partial or complete cure for a disorder and/or adverse effect attributable to the disorder.

To "prevent" intends to prevent a disorder or effect in vitro or in vivo in a system or subject that is predisposed to the disorder or effect. An example of such is preventing the formation of a biofilm in a system that is infected with a microorganism known to produce one.

"Pharmaceutically acceptable carriers" refers to any diluents, excipients or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like and consistent with conventional pharmaceutical practices.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, nasal administration, injection and topical application.

The term "effective amount" refers to a quantity sufficient to achieve a beneficial or desired result or effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The agents and compositions can be used in the manufacture of medicaments and for the treatment of humans and other animals by administration in accordance with conventional procedures, such as an active ingredient in pharmaceutical compositions.

An agent of the present invention can be administered for therapy by any suitable route of administration. It will also be appreciated that the preferred route will vary with the condition and age of the recipient and the disease being treated.

An example of a solid phase support include glass, polystyrene, polypropylene, polyethylene, dextran, nylon, amylases, natural and modified celluloses, polyacrylamides, gabbros and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead or cylindrical, as in the inside surface of a test tube or the external surface of a rod. Alternatively, the surface may be flat such as a sheet, test strip, etc. or alternatively polystyrene beads. Those skilled in the art will know many other suitable carriers for binding antibody or antigen or will be able to ascertain the same by use of routine experimentation.

As used herein, the terms "antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-IHF, anti-HU, anti-OMP P5, for example, refers to a monoclonal or polyclonal antibody that binds and/or has an affinity to a particular protein. For example, "anti-IHF" refers to an antibody that binds to the IHF protein. The specific antibody may have affinity or bind to proteins other than the protein it was raised against. For example, anti-IHF, while specifically raised against the IHF protein, may also bind other proteins that are related either through sequence homology or through structure homology.

The antibodies can be polyclonal, monoclonal, multispecific (e.g., bispecific antibodies), and antibody fragments, so long as they exhibit the desired biological activity. Antibodies can be isolated from any suitable biological source, e.g., murine, rat, sheep and canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}Sn$, $^{117}Sn$ and $^{119}Sn$, a non-radioactive isotopes such as $^{13}C$ and $^{15}N$, polynucleotide or protein such as an antibody so as to generate a "labeled" composition. The term also includes sequences conjugated to the polynucleotide that will provide a signal upon expression of the inserted sequences, such as green fluorescent protein (GFP) and the like. While the term "label" generally intends compositions covalently attached to the composition to be detected, it specifically excludes naturally occurring nucleosides and amino acids that are known to fluoresce under certain conditions (e.g. temperature, pH, etc.) and generally any natural fluorescence that may be present in the composition to be detected. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multi-specific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285-320). A synthetic or altered antigen disclosed herein is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the melanoma specific antigen gp100.

The term "passive immunity" refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

"Immune response" broadly refers to the antigen-specific responses of lymphocytes to foreign substances. The terms "immunogen" and "immunogenic" refer to molecules with the capacity to elicit an immune response. All immunogens are antigens; however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

The term "modulate an immune response" includes inducing (increasing, eliciting) an immune response; and reducing (suppressing) an immune response. An immunomodulatory method (or protocol) is one that modulates an immune response in a subject.

The term "vector" refers to a polynucleotide (usually DNA) used to artificially carry foreign genetic material to another cell where it can be replicated or expressed. Non-limiting exemplary vectors include plasmids, viral vectors, cosmids, and artificial chromosomes. Such vectors may be derived from a variety of sources, including bacterial and viral sources. A non-limiting exemplary viral source for a plasmid is adeno-associated virus.

As used herein, the term "recombinant expression system" refers to a genetic construct or constructs for the expression of certain genetic material formed by recombination; the term "construct" in this regard is interchangeable with the term "vector" as defined herein.

An "HMG domain," "high mobility group (HMG) box domain," or "HMGB" refers to an amino acid sequence that is involved in binding DNA (Stros et al., Cell Mol Life Sci. 64(19-20):2590-606 (2007)). "In one embodiment, the structure of the HMG-box domain consists of three helices in an irregular array. In another embodiment, an HMG-box domain enables a protein to bind non-B-type DNA conformations (kinked or unwound) with high affinity. HMG-box domains can be found in high mobility group proteins, which are involved in the regulation of DNA-dependent processes such as transcription, replication and DNA repair, all of which require changing the conformation of chromatin (Thomas (2001) Biochem. Soc. Trans. 29(Pt 4):395-401). HMGB1" is a high mobility group box (HMGB) 1 protein that is reported to bind to and distort the minor groove of DNA. Recombinant or isolated protein and polypeptide are commercially available from Atgenglobal, ProSpecBio, Protein1 and Abnova.

HMG-box proteins are found in a variety of eukaryotic organisms and can be broadly divided into two groups, based on sequence-dependent and sequence-independent DNA recognition; the former usually contain one HMG-box motif, while the latter can contain multiple HMG-box motifs. Non-limiting examples of polypeptides comprising an HMG-box domain include HMG1(HMGB1), HMG2 (HMGB2), HMGB3 and HMGB4 non-histone components of chromatin; SRY (sex determining region Y protein) involved in differential gonadogenesis; the SOX family of transcription factors (Harley et al. (2003) Endocr. Rev. 24(4):466-87); sequence-specific LEF1 (lymphoid enhancer binding factor 1) and TCF-1 (T-cell factor 1) involved in regulation of organogenesis and thymocyte differentiation (Labbé et al. (2000) Proc. Natl. Acad. Sci. USA 97(15): 8358-63); structure-specific recognition protein SSRP involved in transcription and replication; MTF1 mitochondrial transcription factor; nucleolar transcription factors UBF 1/2 (upstream binding factor) involved in transcription by RNA polymerase I; Abf2 yeast ARS-binding factor (Cho et al. (2001) Biochim. Biophys. Acta. 1522(3):175-86);

yeast transcription factors lxr1, Rox1, Nhp6b and Spp41; mating type proteins (MAT) involved in the sexual reproduction of fungi (Barve et al. (2003) Fungal Genet. Biol. 39(2):151-67); and the YABBY plant-specific transcription factors.

Exemplary sequences of polypeptides comprising an HMG-box domain include NP_002119 (human HMGB1), NP_001124160 (human HMGB2), NP_005333 (human HMGB3) and NP_660206 (human HMGB4). Amino acid residues from about 9 to about 76 of the human HMGB1, for example, form an HMG-box domain and amino acid residues from about 90 to about 138 form another HMG-box domain. An HMGB1 fragment that contains either of these two HMG-box domains, for example, also constitutes a polypeptide comprising an HMG-box domain, within the meaning of the present disclosure. In the examples described herein, a recombinant HMGB1 (derived from a human and recombinantly expressed and purified in *E. coli*) is used as a comparator to mHMGB1 (C45S) and has the sequence:

MGKGDPKKPRGKMSSYAFFVQTCREEHKKKHPDASVNFSEFSKKCSERWK

TMSAKEKGKFEDMAKADKARYEREMKTYIPPKGETKKKFKDPNAPKRPPS

AFFLFCSEYRPKIKGEHPGLSIGDVAKKLGEMWNNTAADDKQPYEKKAAK

LKEKYEKDIAAYRAKGKPDAAKKGVVKAEKSKKKKEEEEGEEDEEDEEEE

EDEEDEDEEEDDDDE

The term "modified high mobility group-box 1 domain" as used herein refers to an HMGB1 that has been mutated, e.g., via substitutions of the cysteine residues at positions 23, 45, and/or 106 based on the consensus sequence polypeptide of HMGB1 derived from a human:

MGKGDPKKPRGKMSSYAFFVQTCREEHKKKHPDASVNFSEFSKKCSERWK

TMSAKEKGKFEDMAKADKARYEREMKTYIPPKGETKKKFKDPNAPKRPPS

AFFLFCSEYRPKIKGEHPGLSIGDVAKKLGEMWNNTAADDKQPYEKKAAK

LKEKYEKDIAAYRAKGKPDAAKKGVVKAEKSKKKKEEEEGEEDEEDEEEE

EDEEDEDEEEDDDDE

Non-limiting exemplary sequences of modified high mobility group-box 1 domains include but are not limited to:

mHMGB1 (C23S):
MGKGDPKKPRGKMSSYAFFVQTSREEHKKKHPDASVNFSEFSKKCSERWK

TMSAKEKGKFEDMAKADKARYEREMKTYIPPKGETKKKFKDPNAPKRPPS

AFFLFCSEYRPKIKGEHPGLSIGDVAKKLGEMWNNTAADDKQPYEKKAAK

LKEKYEKDIAAYRAKGKPDAAKKGVVKAEKSKKKKEEEEGEEDEEDEEEE

EDEEDEDEEEDDDDE mHMGB1 (C45S):
MGKGDPKKPRGKMSSYAFFVQTCREEHKKKHPDASVNFSEFSKKSSERWK

TMSAKEKGKFEDMAKADKARYEREMKTYIPPKGETKKKFKDPNAPKRPPS

AFFLFCSEYRPKIKGEHPGLSIGDVAKKLGEMWNNTAADDKQPYEKKAAK

LKEKYEKDIAAYRAKGKPDAAKKGVVKAEKSKKKKEEEEGEEDEEDEEEE

EDEEDEDEEEDDDDE mHMGB1 (C106S):
MGKGDPKKPRGKMSSYAFFVQTCREEHKKKHPDASVNFSEFSKKCSERWK

TMSAKEKGKFEDMAKADKARYEREMKTYIPPKGETKKKFKDPNAPKRPPS

AFFLFSSEYRPKIKGEHPGLSIGDVAKKLGEMWNNTAADDKQPYEKKAAK

LKEKYEKDIAAYRAKGKPDAAKKGVVKAEKSKKKKEEEEGEEDEEDEEEE

EDEEDEDEEEDDDDE mHMGB1 (C23S, C45S - double mutant):
MGKGDPKKPRGKMSSYAFFVQTSREEHKKKHPDASVNFSEFSKKSSERWK

TMSAKEKGKFEDMAKADKARYEREMKTYIPPKGETKKKFKDPNAPKRPPS

AFFLFCSEYRPKIKGEHPGLSIGDVAKKLGEMWNNTAADDKQPYEKKAAK

LKEKYEKDIAAYRAKGKPDAAKKGVVKAEKSKKKKEEEEGEEDEEDEEEE

EDEEDEDEEEDDDDE mHMGB1 (C23S, C106S - double mutant):
MGKGDPKKPRGKMSSYAFFVQTSREEHKKKHPDASVNFSEFSKKCSERWK

TMSAKEKGKFEDMAKADKARYEREMKTYIPPKGETKKKFKDPNAPKRPPS

AFFLFSSEYRPKIKGEHPGLSIGDVAKKLGEMWNNTAADDKQPYEKKAAK

LKEKYEKDIAAYRAKGKPDAAKKGVVKAEKSKKKKEEEEGEEDEEDEEEE

EDEEDEDEEEDDDDE mHMGB1 (C45S, C106S - double mutant):
MGKGDPKKPRGKMSSYAFFVQTCREEHKKKHPDASVNFSEFSKKSSERWK

TMSAKEKGKFEDMAKADKARYEREMKTYIPPKGETKKKFKDPNAPKRPPS

AFFLFSSEYRPKIKGEHPGLSIGDVAKKLGEMWNNTAADDKQPYEKKAAK

LKEKYEKDIAAYRAKGKPDAAKKGVVKAEKSKKKKEEEEGEEDEEDEEEE

EDEEDEDEEEDDDDE mHMGB1 (C23S, C45S, C106S - triple mutant):
MGKGDPKKPRGKMSSYAFFVQTSREEHKKKHPDASVNFSEFSKKSSERWK

TMSAKEKGKFEDMAKADKARYEREMKTYIPPKGETKKKFKDPNAPKRPPS

AFFLFSSEYRPKIKGEHPGLSIGDVAKKLGEMWNNTAADDKQPYEKKAAK

LKEKYEKDIAAYRAKGKPDAAKKGVVKAEKSKKKKEEEEGEEDEEDEEEE

EDEEDEDEEEDDDDE

Nucleic acid sequences encoding these modified high mobility group-box 1 domains are also provided herein below:

mHMGB1 (C23S):
ATGGGCAAAGGAGATCCTAAGAAGCCGAGAGGCAAAATGTCATCATATGCATTTTT

TGTGCAAACTAGTCGGGAGGAGCATAAGAAGAAGCACCCAGATGCTTCAGTCAA

CTTCTCAGAGTTTTCTAAGAAGTGCTCAGAGAGGTGGAAGACCATGTCTGCTAAA

GAGAAAGGAAAATTTGAAGATATGGCAAAGGCGGACAAGGCCCGTTATGAAAGA

-continued

```
GAAATGAAAACCTATATCCCTCCCAAAGGGGAGACAAAAAAGAAGTTCAAGGATC

CCAATGCACCCAAGAGGCCTCCTTCGGCCTTCTTCCTCTTCTGCTCTGAGTATCGC

CCAAAAATCAAAGGAGAACATCCTGGCCTGTCCATTGGTGATGTTGCGAAGAAAC

TGGGAGAGATGTGGAATAACACTGCTGCAGATGACAAGCAGCCTTATGAAAGAA

GGCTGCGAAGCTGAAGGAAAAATACGAAAAGGATATTGCTGCATATCGAGCTAAA

GGAAAGCCTGATGCAGCAAAAAAGGGAGTTGTCAAGGCTGAAAAAAGCAAGAA

AAAGAAGGAAGAGGAGGAAGGTGAGGAAGATGAAGAGGATGAGGAGGAGGAG

GAAGATGAAGAAGATGAAGATGAAGAAGAAGATGATGATGATGAA mHMGB1 (C45S):
ATGGGCAAAGGAGATCCTAAGAAGCCGAGAGGCAAAATGTCATCATATGCATTTTT

TGTGCAAACTTGTCGGGAGGAGCATAAGAAGAAGCACCCAGATGCTTCAGTCAA

CTTCTCAGAGTTTTCTAAGAAGAGTTCAGAGAGGTGGAAGACCATGTCTGCTAAA

GAGAAAGGAAAATTTGAAGATATGGCAAAGGCGGACAAGGCCCGTTATGAAGA

GAAATGAAAACCTATATCCCTCCCAAAGGGGAGACAAAAAAGAAGTTCAAGGATC

CCAATGCACCCAAGAGGCCTCCTTCGGCCTTCTTCCTCTTCTGCTCTGAGTATCGC

CCAAAAATCAAAGGAGAACATCCTGGCCTGTCCATTGGTGATGTTGCGAAGAAAC

TGGGAGAGATGTGGAATAACACTGCTGCAGATGACAAGCAGCCTTATGAAAGAA

GGCTGCGAAGCTGAAGGAAAAATACGAAAAGGATATTGCTGCATATCGAGCTAAA

GGAAAGCCTGATGCAGCAAAAAAGGGAGTTGTCAAGGCTGAAAAAAGCAAGAA

AAAGAAGGAAGAGGAGGAAGGTGAGGAAGATGAAGAGGATGAGGAGGAGGAG

GAAGATGAAGAAGATGAAGATGAAGAAGAAGATGATGATGATGAA mHMGB1 (C106S):
ATGGGCAAAGGAGATCCTAAGAAGCCGAGAGGCAAAATGTCATCATATGCATTTTT

TGTGCAAACTTGTCGGGAGGAGCATAAGAAGAAGCACCCAGATGCTTCAGTCAA

CTTCTCAGAGTTTTCTAAGAAGTGCTCAGAGAGGTGGAAGACCATGTCTGCTAAA

GAGAAAGGAAAATTTGAAGATATGGCAAAGGCGGACAAGGCCCGTTATGAAGA

GAAATGAAAACCTATATCCCTCCCAAAGGGGAGACAAAAAAGAAGTTCAAGGATC

CCAATGCACCCAAGAGGCCTCCTTCGGCCTTCTTCCTCTTCAGCTCTGAGTATCGC

CCAAAAATCAAAGGAGAACATCCTGGCCTGTCCATTGGTGATGTTGCGAAGAAAC

TGGGAGAGATGTGGAATAACACTGCTGCAGATGACAAGCAGCCTTATGAAAGAA

GGCTGCGAAGCTGAAGGAAAAATACGAAAAGGATATTGCTGCATATCGAGCTAAA

GGAAAGCCTGATGCAGCAAAAAAGGGAGTTGTCAAGGCTGAAAAAAGCAAGAA

AAAGAAGGAAGAGGAGGAAGGTGAGGAAGATGAAGAGGATGAGGAGGAGGAG

GAAGATGAAGAAGATGAAGATGAAGAAGAAGATGATGATGATGAA mHMGB1 (C23S, C45S - double mutant):
ATGGGCAAAGGAGATCCTAAGAAGCCGAGAGGCAAAATGTCATCATATGCATTTTT

TGTGCAAACTAGTCGGGAGGAGCATAAGAAGAAGCACCCAGATGCTTCAGTCAA

CTTCTCAGAGTTTTCTAAGAAGAGTTCAGAGAGGTGGAAGACCATGTCTGCTAAA

GAGAAAGGAAAATTTGAAGATATGGCAAAGGCGGACAAGGCCCGTTATGAAGA

GAAATGAAAACCTATATCCCTCCCAAAGGGGAGACAAAAAAGAAGTTCAAGGATC

CCAATGCACCCAAGAGGCCTCCTTCGGCCTTCTTCCTCTTCTGCTCTGAGTATCGC

CCAAAAATCAAAGGAGAACATCCTGGCCTGTCCATTGGTGATGTTGCGAAGAAAC
```

-continued

TGGGAGAGATGTGGAATAACACTGCTGCAGATGACAAGCAGCCTTATGAAAAGAA

GGCTGCGAAGCTGAAGGAAAAATACGAAAAGGATATTGCTGCATATCGAGCTAAA

GGAAAGCCTGATGCAGCAAAAAAGGGAGTTGTCAAGGCTGAAAAAAGCAAGAA

AAAGAAGGAAGAGGAGGAAGGTGAGGAAGATGAAGAGGATGAGGAGGAGGAG

GAAGATGAAGAAGATGAAGATGAAGAAGAAGATGATGATGATGAA mHMGB1 (C23S, C106S - double mutant):
ATGGGCAAAGGAGATCCTAAGAAGCCGAGAGGCAAAATGTCATCATATGCATTTTT

TGTGCAAACTAGTCGGGAGGAGCATAAGAAGAAGCACCCAGATGCTTCAGTCAA

CTTCTCAGAGTTTTCTAAGAAGTGCTCAGAGAGGTGGAAGACCATGTCTGCTAAA

GAGAAAGGAAAATTTGAAGATATGGCAAAGGCGGACAAGGCCCGTTATGAAGA

GAAATGAAAACCTATATCCCTCCCAAAGGGGAGACAAAAAAGAAGTTCAAGGATC

CCAATGCACCCAAGAGGCCTCCTTCGGCCTTCTTCCTCTTCAGCTCTGAGTATCGC

CCAAAAATCAAAGGAGAACATCCTGGCCTGTCCATTGGTGATGTTGCGAAGAAC

TGGGAGAGATGTGGAATAACACTGCTGCAGATGACAAGCAGCCTTATGAAAAGAA

GGCTGCGAAGCTGAAGGAAAAATACGAAAAGGATATTGCTGCATATCGAGCTAAA

GGAAAGCCTGATGCAGCAAAAAAGGGAGTTGTCAAGGCTGAAAAAAGCAAGAA

AAAGAAGGAAGAGGAGGAAGGTGAGGAAGATGAAGAGGATGAGGAGGAGGAG

GAAGATGAAGAAGATGAAGATGAAGAAGAAGATGATGATGATGAA mHMGB1 (C45S, C106S - double mutant):
ATGGGCAAAGGAGATCCTAAGAAGCCGAGAGGCAAAATGTCATCATATGCATTTTT

TGTGCAAACTTGTCGGGAGGAGCATAAGAAGAAGCACCCAGATGCTTCAGTCAA

CTTCTCAGAGTTTTCTAAGAAGAGTTCAGAGAGGTGGAAGACCATGTCTGCTAAA

GAGAAAGGAAAATTTGAAGATATGGCAAAGGCGGACAAGGCCCGTTATGAAGA

GAAATGAAAACCTATATCCCTCCCAAAGGGGAGACAAAAAAGAAGTTCAAGGATC

CCAATGCACCCAAGAGGCCTCCTTCGGCCTTCTTCCTCTTCAGCTCTGAGTATCGC

CCAAAAATCAAAGGAGAACATCCTGGCCTGTCCATTGGTGATGTTGCGAAGAAC

TGGGAGAGATGTGGAATAACACTGCTGCAGATGACAAGCAGCCTTATGAAAAGAA

GGCTGCGAAGCTGAAGGAAAAATACGAAAAGGATATTGCTGCATATCGAGCTAAA

GGAAAGCCTGATGCAGCAAAAAAGGGAGTTGTCAAGGCTGAAAAAAGCAAGAA

AAAGAAGGAAGAGGAGGAAGGTGAGGAAGATGAAGAGGATGAGGAGGAGGAG

GAAGATGAAGAAGATGAAGATGAAGAAGAAGATGATGATGATGAA mHMGB1 (C23S, C45S, C106S - triple mutant):
ATGGGCAAAGGAGATCCTAAGAAGCCGAGAGGCAAAATGTCATCATATGCATTTTT

TGTGCAAACTAGTCGGGAGGAGCATAAGAAGAAGCACCCAGATGCTTCAGTCAA

CTTCTCAGAGTTTTCTAAGAAGAGTTCAGAGAGGTGGAAGACCATGTCTGCTAAA

GAGAAAGGAAAATTTGAAGATATGGCAAAGGCGGACAAGGCCCGTTATGAAGA

GAAATGAAAACCTATATCCCTCCCAAAGGGGAGACAAAAAAGAAGTTCAAGGATC

CCAATGCACCCAAGAGGCCTCCTTCGGCCTTCTTCCTCTTCAGCTCTGAGTATCGC

CCAAAAATCAAAGGAGAACATCCTGGCCTGTCCATTGGTGATGTTGCGAAGAAC

TGGGAGAGATGTGGAATAACACTGCTGCAGATGACAAGCAGCCTTATGAAAAGAA

GGCTGCGAAGCTGAAGGAAAAATACGAAAAGGATATTGCTGCATATCGAGCTAAA

GGAAAGCCTGATGCAGCAAAAAAGGGAGTTGTCAAGGCTGAAAAAAGCAAGAA

AAAGAAGGAAGAGGAGGAAGGTGAGGAAGATGAAGAGGATGAGGAGGAGGAG

GAAGATGAAGAAGATGAAGATGAAGAAGAAGATGATGATGATGAA

It is appreciated that the term "modified high mobility group-box 1 domain" further encompasses those equivalents which have at least about 60%, or at least about 65%, or at least about 70%, or at least about 75%, or at least about 80%, or at least about 85%, or at least about 90%, or at least about 95%, or at least about 98% or at least about 99% identical to the HMGB1 consensus sequence and comprise the same substitutions at corresponding positions in the equivalent sequences based on alignment against the HMGB1 consensus sequence.

It is appreciated that among the equivalents to a modified high mobility group-box 1 domain are modified high mobility group-box 2, modified high mobility group-box 3, and modified high mobility group-box 4 comprising cysteine to serine substitutions at one or more amino acid positions corresponding to C23S, C45S, and C106S of a modified high mobility group box 1.

Corresponding amino acid substitutions to yield a modified high mobility group-box 2 can be made at the cysteine residues at positions 23, 45, and/or 106 based on the consensus sequence polypeptide of HMGB2 derived from a human:

MGKGDPNKPRGKMSSYAFFVQTCREEHKKKHPDSSVNFAEFSKKCSERWK

TMSAKEKSKFEDMAKSDKARYDREMKNYVPPKGDKKGKKKDPNAPKRPPS

AFFLFCSEHRPKIKSEHPGLSIGDTAKKLGEMWSEQSAKDKQPYEQKAAK

LKEKYEKDIAAYRAKGKSEAGKKGPGRPTGSKKKNEPEDEEEEEEEEDED

EEEEDEDEE

Non-limiting exemplary sequences a modified high mobility group-box 2 domains include but are not limited to:

mHMGB2 (C23S):
MGKGDPNKPRGKMSSYAFFVQTSREEHKKKHPDSSVNFAEFSKKCSERWK

TMSAKEKSKFEDMAKSDKARYDREMKNYVPPKGDKKGKKKDPNAPKRPPS

AFFLFCSEHRPKIKSEHPGLSIGDTAKKLGEMWSEQSAKDKQPYEQKAAK

LKEKYEKDIAAYRAKGKSEAGKKGPGRPTGSKKKNEPEDEEEEEEEEDED

EEEEDEDEE mHMGB2 (C45S):
MGKGDPNKPRGKMSSYAFFVQTCREEHKKKHPDSSVNFAEFSKKSSERWK

TMSAKEKSKFEDMAKSDKARYDREMKNYVPPKGDKKGKKKDPNAPKRPPS

AFFLFCSEHRPKIKSEHPGLSIGDTAKKLGEMWSEQSAKDKQPYEQKAAK

-continued

LKEKYEKDIAAYRAKGKSEAGKKGPGRPTGSKKKNEPEDEEEEEEEEDED

EEEEDEDEE mHMGB2 (C106S):
MGKGDPNKPRGKMSSYAFFVQTCREEHKKKHPDSSVNFAEFSKKCSERWK

TMSAKEKSKFEDMAKSDKARYDREMKNYVPPKGDKKGKKKDPNAPKRPPS

AFFLFSSEHRPKIKSEHPGLSIGDTAKKLGEMWSEQSAKDKQPYEQKAAK

LKEKYEKDIAAYRAKGKSEAGKKGPGRPTGSKKKNEPEDEEEEEEEEDED

EEEEDEDEE mHMGB2 (C23S, C45S - double mutant):
MGKGDPNKPRGKMSSYAFFVQTSREEHKKKHPDSSVNFAEFSKKSSERWK

TMSAKEKSKFEDMAKSDKARYDREMKNYVPPKGDKKGKKKDPNAPKRPPS

AFFLFCSEHRPKIKSEHPGLSIGDTAKKLGEMWSEQSAKDKQPYEQKAAK

LKEKYEKDIAAYRAKGKSEAGKKGPGRPTGSKKKNEPEDEEEEEEEEDED

EEEEDEDEE mHMGB2 (C23S, C106S - double mutant):
MGKGDPNKPRGKMSSYAFFVQTSREEHKKKHPDSSVNFAEFSKKCSERWK

TMSAKEKSKFEDMAKSDKARYDREMKNYVPPKGDKKGKKKDPNAPKRPPS

AFFLFSSEHRPKIKSEHPGLSIGDTAKKLGEMWSEQSAKDKQPYEQKAAK

LKEKYEKDIAAYRAKGKSEAGKKGPGRPTGSKKKNEPEDEEEEEEEEDED

EEEEDEDEE mHMGB2 (C45S, C106S - double mutant):
MGKGDPNKPRGKMSSYAFFVQTCREEHKKKHPDSSVNFAEFSKKSSERWK

TMSAKEKSKFEDMAKSDKARYDREMKNYVPPKGDKKGKKKDPNAPKRPPS

AFFLFSSEHRPKIKSEHPGLSIGDTAKKLGEMWSEQSAKDKQPYEQKAAK

LKEKYEKDIAAYRAKGKSEAGKKGPGRPTGSKKKNEPEDEEEEEEEEDED

EEEEDEDEE mHMGB2 (C23S, C45S, C106S - triple mutant):
MGKGDPNKPRGKMSSYAFFVQTSREEHKKKHPDSSVNFAEFSKKSSERWK

TMSAKEKSKFEDMAKSDKARYDREMKNYVPPKGDKKGKKKDPNAPKRPPS

AFFLFSSEHRPKIKSEHPGLSIGDTAKKLGEMWSEQSAKDKQPYEQKAAK

LKEKYEKDIAAYRAKGKSEAGKKGPGRPTGSKKKNEPEDEEEEEEEEDED

EEEEDEDEE

Nucleic acid sequences encoding these modified high mobility group-box 2 domains are also provided herein below:

mHMGB2 (C23S):
ATGGGTAAAGGAGACCCCAACAAGCCGCGGGGCAAAATGTCCTCGTACGCCTTCT

TCGTGCAGACCAGTCGGGAAGAGCACAAGAAGAAACACCCGGACTCTTCCGTCA

ATTTCGCGGAATTCTCCAAGAAGTGTTCGGAGAGATGGAAGACCATGTCTGCAAA

GGAGAAGTCGAAGTTTGAAGATATGGCAAAAAGTGACAAAGCTCGCTATGACAG

```
GGAGATGAAAAATTACGTTCCTCCCAAAGGTGATAAGAAGGGGAAGAAAAAGGA

CCCCAATGCTCCTAAAAGGCCACCATCTGCCTTCTTCCTGTTTTGCTCTGAACATC

GCCCAAAGATCAAAAGTGAACACCCTGGCCTATCCATTGGGGATACTGCAAAGAA

ATTGGGTGAAATGTGGTCTGAGCAGTCAGCCAAAGATAAACAACCATATGAACAG

AAAGCAGCTAAGCTAAAGGAGAAATATGAAAAGGATATTGCTGCATATCGTGCCA

AGGGCAAAAGTGAAGCAGGAAAGAAGGGCCCTGGCAGGCCAACAGGCTCAAAG

AAGAAGAACGAACCAGAAGATGAGGAGGAGGAGGAGGAAGAAGAAGATGAAGA

TGAGGAGGAAGAGGATGAAGATGAAGAATAA mHMGB2 (C45S):
ATGGGTAAAGGAGACCCCAACAAGCCGCGGGGCAAAATGTCCTCGTACGCCTTCT

TCGTGCAGACCTGCCGGGAAGAGCACAAGAAGAAACACCCGGACTCTTCCGTCA

ATTTCGCGGAATTCTCCAAGAAGAGTTCGGAGAGATGGAAGACCATGTCTGCAAA

GGAGAAGTCGAAGTTTGAAGATATGGCAAAAAGTGACAAAGCTCGCTATGACAG

GGAGATGAAAAATTACGTTCCTCCCAAAGGTGATAAGAAGGGGAAGAAAAAGGA

CCCCAATGCTCCTAAAAGGCCACCATCTGCCTTCTTCCTGTTTTGCTCTGAACATC

GCCCAAAGATCAAAAGTGAACACCCTGGCCTATCCATTGGGGATACTGCAAAGAA

ATTGGGTGAAATGTGGTCTGAGCAGTCAGCCAAAGATAAACAACCATATGAACAG

AAAGCAGCTAAGCTAAAGGAGAAATATGAAAAGGATATTGCTGCATATCGTGCCA

AGGGCAAAAGTGAAGCAGGAAAGAAGGGCCCTGGCAGGCCAACAGGCTCAAAG

AAGAAGAACGAACCAGAAGATGAGGAGGAGGAGGAGGAAGAAGAAGATGAAGA

TGAGGAGGAAGAGGATGAAGATGAAGAATAA mHMGB2 (C106S):
ATGGGTAAAGGAGACCCCAACAAGCCGCGGGGCAAAATGTCCTCGTACGCCTTCT

TCGTGCAGACCTGCCGGGAAGAGCACAAGAAGAAACACCCGGACTCTTCCGTCA

ATTTCGCGGAATTCTCCAAGAAGTGTTCGGAGAGATGGAAGACCATGTCTGCAAA

GGAGAAGTCGAAGTTTGAAGATATGGCAAAAAGTGACAAAGCTCGCTATGACAG

GGAGATGAAAAATTACGTTCCTCCCAAAGGTGATAAGAAGGGGAAGAAAAAGGA

CCCCAATGCTCCTAAAAGGCCACCATCTGCCTTCTTCCTGTTAGCTCTGAACATC

GCCCAAAGATCAAAAGTGAACACCCTGGCCTATCCATTGGGGATACTGCAAAGAA

ATTGGGTGAAATGTGGTCTGAGCAGTCAGCCAAAGATAAACAACCATATGAACAG

AAAGCAGCTAAGCTAAAGGAGAAATATGAAAAGGATATTGCTGCATATCGTGCCA

AGGGCAAAAGTGAAGCAGGAAAGAAGGGCCCTGGCAGGCCAACAGGCTCAAAG

AAGAAGAACGAACCAGAAGATGAGGAGGAGGAGGAGGAAGAAGAAGATGAAGA

TGAGGAGGAAGAGGATGAAGATGAAGAATAA mHMGB2 (C23S, C45S - double mutant):
ATGGGTAAAGGAGACCCCAACAAGCCGCGGGGCAAAATGTCCTCGTACGCCTTCT

TCGTGCAGACCAGTCGGGAAGAGCACAAGAAGAAACACCCGGACTCTTCCGTCA

ATTTCGCGGAATTCTCCAAGAAGAGTTCGGAGAGATGGAAGACCATGTCTGCAAA

GGAGAAGTCGAAGTTTGAAGATATGGCAAAAAGTGACAAAGCTCGCTATGACAG

GGAGATGAAAAATTACGTTCCTCCCAAAGGTGATAAGAAGGGGAAGAAAAAGGA

CCCCAATGCTCCTAAAAGGCCACCATCTGCCTTCTTCCTGTTTTGCTCTGAACATC

GCCCAAAGATCAAAAGTGAACACCCTGGCCTATCCATTGGGGATACTGCAAAGAA
```

ATTGGGTGAAATGTGGTCTGAGCAGTCAGCCAAAGATAAACAACCATATGAACAG

AAAGCAGCTAAGCTAAAGGAGAAATATGAAAAGGATATTGCTGCATATCGTGCCA

AGGGCAAAAGTGAAGCAGGAAAGAAGGGCCCTGGCAGGCCAACAGGCTCAAAG

AAGAAGAACGAACCAGAAGATGAGGAGGAGGAGGAGGAAGAAGAAGATGAAGA

TGAGGAGGAAGAGGATGAAGATGAAGAATAA mHMGB2 (C23S, C106S - double mutant):
ATGGGTAAAGGAGACCCCAACAAGCCGCGGGGCAAAATGTCCTCGTACGCCTTCT

TCGTGCAGACCAGTCGGGAAGAGCACAAGAAGAAACACCCGGACTCTTCCGTCA

ATTTCGCGGAATTCTCCAAGAAGTGTTCGGAGAGATGGAAGACCATGTCTGCAAA

GGAGAAGTCGAAGTTTGAAGATATGGCAAAAAGTGACAAAGCTCGCTATGACAG

GGAGATGAAAAATTACGTTCCTCCCAAAGGTGATAAGAAGGGGAAGAAAAAGGA

CCCCAATGCTCCTAAAAGGCCACCATCTGCCTTCTTCCTGTTTAGCTCTGAACATC

GCCCAAAGATCAAAAGTGAACACCCTGGCCTATCCATTGGGGATACTGCAAAGAA

ATTGGGTGAAATGTGGTCTGAGCAGTCAGCCAAAGATAAACAACCATATGAACAG

AAAGCAGCTAAGCTAAAGGAGAAATATGAAAAGGATATTGCTGCATATCGTGCCA

AGGGCAAAAGTGAAGCAGGAAAGAAGGGCCCTGGCAGGCCAACAGGCTCAAAG

AAGAAGAACGAACCAGAAGATGAGGAGGAGGAGGAGGAAGAAGAAGATGAAGA

TGAGGAGGAAGAGGATGAAGATGAAGAATAA mHMGB2 (C45S, C106S - double mutant):
ATGGGTAAAGGAGACCCCAACAAGCCGCGGGGCAAAATGTCCTCGTACGCCTTCT

TCGTGCAGACCTGCCGGGAAGAGCACAAGAAGAAACACCCGGACTCTTCCGTCA

ATTTCGCGGAATTCTCCAAGAAGAGTTCGGAGAGATGGAAGACCATGTCTGCAAA

GGAGAAGTCGAAGTTTGAAGATATGGCAAAAAGTGACAAAGCTCGCTATGACAG

GGAGATGAAAAATTACGTTCCTCCCAAAGGTGATAAGAAGGGGAAGAAAAAGGA

CCCCAATGCTCCTAAAAGGCCACCATCTGCCTTCTTCCTGTTTAGCTCTGAACATC

GCCCAAAGATCAAAAGTGAACACCCTGGCCTATCCATTGGGGATACTGCAAAGAA

ATTGGGTGAAATGTGGTCTGAGCAGTCAGCCAAAGATAAACAACCATATGAACAG

AAAGCAGCTAAGCTAAAGGAGAAATATGAAAAGGATATTGCTGCATATCGTGCCA

AGGGCAAAAGTGAAGCAGGAAAGAAGGGCCCTGGCAGGCCAACAGGCTCAAAG

AAGAAGAACGAACCAGAAGATGAGGAGGAGGAGGAGGAAGAAGAAGATGAAGA

TGAGGAGGAAGAGGATGAAGATGAAGAATAA mHMGB2 (C23S, C45S, C106Z - triple mutant):
ATGGGTAAAGGAGACCCCAACAAGCCGCGGGGCAAAATGTCCTCGTACGCCTTCT

TCGTGCAGACCAGTCGGGAAGAGCACAAGAAGAAACACCCGGACTCTTCCGTCA

ATTTCGCGGAATTCTCCAAGAAGAGTTCGGAGAGATGGAAGACCATGTCTGCAAA

GGAGAAGTCGAAGTTTGAAGATATGGCAAAAAGTGACAAAGCTCGCTATGACAG

GGAGATGAAAAATTACGTTCCTCCCAAAGGTGATAAGAAGGGGAAGAAAAAGGA

CCCCAATGCTCCTAAAAGGCCACCATCTGCCTTCTTCCTGTTTAGCTCTGAACATC

GCCCAAAGATCAAAAGTGAACACCCTGGCCTATCCATTGGGGATACTGCAAAGAA

ATTGGGTGAAATGTGGTCTGAGCAGTCAGCCAAAGATAAACAACCATATGAACAG

AAAGCAGCTAAGCTAAAGGAGAAATATGAAAAGGATATTGCTGCATATCGTGCCA

AGGGCAAAAGTGAAGCAGGAAAGAAGGGCCCTGGCAGGCCAACAGGCTCAAAG

-continued
```
AAGAAGAACGAACCAGAAGATGAGGAGGAGGAGGAGGAAGAAGAAGATGAAGA

TGAGGAGGAAGAGGATGAAGATGAAGAATAA
```

Corresponding amino acid substitutions to yield a modified high mobility group-box 3 can be made at the cysteine residues at positions 23, 45, and/or 104 based on the consensus sequence polypeptide of HMGB3 derived from a human:

```
MAKGDPKKPKGKMSAYAFFVQTCREEHKKKNPEVPVNFAEFSKKCSERWK

TMSGKEKSKFDEMAKADKVRYDREMKDYGPAKGGKKKKDPNAPKRPPSGF

FLFCSEFRPKIKSTNPGISIGDVAKKLGEMWNNLNDSEKQPYITKAAKLK

EKYEKDVADYKSKGKFDGAKGPAKVARKKVEEEDEEEEEEEEEEEEEDE
```

Non-limiting exemplary sequences a modified high mobility group-box 2 domains include but are not limited to:

```
mHMGB3 (C23S):
MAKGDPKKPKGKMSAYAFFVQTSREEHKKKNPEVPVNFAEFSKKCSERWK

TMSGKEKSKFDEMAKADKVRYDREMKDYGPAKGGKKKKDPNAPKRPPSGF

FLFCSEFRPKIKSTNPGISIGDVAKKLGEMWNNLNDSEKQPYITKAAKLK

EKYEKDVADYKSKGKFDGAKGPAKVARKKVEEEDEEEEEEEEEEEEEDE mHMGB3 (C45S):
MAKGDPKKPKGKMSAYAFFVQTCREEHKKKNPEVPVNFAEFSKKSSERWK

TMSGKEKSKFDEMAKADKVRYDREMKDYGPAKGGKKKKDPNAPKRPPSGF

FLFCSEFRPKIKSTNPGISIGDVAKKLGEMWNNLNDSEKQPYITKAAKLK

EKYEKDVADYKSKGKFDGAKGPAKVARKKVEEEDEEEEEEEEEEEEEDE mHMGB3 (C104S):
MAKGDPKKPKGKMSAYAFFVQTCREEHKKKNPEVPVNFAEFSKKCSERWK

TMSGKEKSKFDEMAKADKVRYDREMKDYGPAKGGKKKKDPNAPKRPPSGF

FLFSSEFRPKIKSTNPGISIGDVAKKLGEMWNNLNDSEKQPYITKAAKLK

EKYEKDVADYKSKGKFDGAKGPAKVARKKVEEEDEEEEEEEEEEEEEDE mHMGB3 (C23S, C45S - double mutant):
MAKGDPKKPKGKMSAYAFFVQTSREEHKKKNPEVPVNFAEFSKKSSERWK

TMSGKEKSKFDEMAKADKVRYDREMKDYGPAKGGKKKKDPNAPKRPPSGF

FLFCSEFRPKIKSTNPGISIGDVAKKLGEMWNNLNDSEKQPYITKAAKLK

EKYEKDVADYKSKGKFDGAKGPAKVARKKVEEEDEEEEEEEEEEEEEDE mHMGB3 (C23S, C104S - double mutant):
MAKGDPKKPKGKMSAYAFFVQTSREEHKKKNPEVPVNFAEFSKKCSERWK

TMSGKEKSKFDEMAKADKVRYDREMKDYGPAKGGKKKKDPNAPKRPPSGF

FLFSSEFRPKIKSTNPGISIGDVAKKLGEMWNNLNDSEKQPYITKAAKLK

EKYEKDVADYKSKGKFDGAKGPAKVARKKVEEEDEEEEEEEEEEEEEDE mHMGB3 (C45S, C104S - double mutant):
MAKGDPKKPKGKMSAYAFFVQTCREEHKKKNPEVPVNFAEFSKKSSERWK

TMSGKEKSKFDEMAKADKVRYDREMKDYGPAKGGKKKKDPNAPKRPPSGF

FLFSSEFRPKIKSTNPGISIGDVAKKLGEMWNNLNDSEKQPYITKAAKLK

EKYEKDVADYKSKGKFDGAKGPAKVARKKVEEEDEEEEEEEEEEEEEDE mHMGB3 (C23S, C45S, C104S - triple mutant):
MAKGDPKKPKGKMSAYAFFVQTSREEHKKKNPEVPVNFAEFSKKSSERWK

TMSGKEKSKFDEMAKADKVRYDREMKDYGPAKGGKKKKDPNAPKRPPSGF

FLFSSEFRPKIKSTNPGISIGDVAKKLGEMWNNLNDSEKQPYITKAAKLK

EKYEKDVADYKSKGKFDGAKGPAKVARKKVEEEDEEEEEEEEEEEEEDE
```

Nucleic acid sequences encoding these modified high mobility group-box 2 domains are also provided herein below:

```
mHMGB3 (C23S):
ATGGCTAAAGGTGACCCCAAGAAACCAAAGGGCAAGATGTCCGCTTATGCCTTCT

TTGTGCAGACAAGTCAGAGAAGAACATAAGAAGAAAAACCCAGAGGTCCCTGTC

AATTTTGCGGAATTTTCCAAGAAGTGCTCTGAGAGGTGGAAGACGATGTCCGGGA

AAGAGAAATCTAAATTTGATGAAATGGCAAAGGCAGATAAAGTGCGCTATGATCG

GGAAATGAAGGATTATGGACCAGCTAAGGGAGGCAAGAAGAAGAAGGATCCTAA

TGCTCCCAAAAGGCCACCGTCTGGATTCTTCCTGTTCTGTTCAGAATTCCGCCCCA

AGATCAAATCCACAAACCCCGGCATCTCTATTGGAGACGTGGCAAAAAAGCTGGG

TGAGATGTGGAATAATTTAAATGACAGTGAAAAGCAGCCTTACATCACTAAGGCG

GCAAAGCTGAAGGAGAAGTATGAGAAGGATGTTGCTGACTATAAGTCGAAAGGA

AAGTTTGATGGTGCAAAGGGTCCTGCTAAAGTTGCCCGGAAAAAGGTGGAAGAG

GAAGATGAAGAAGAGGAGGAGGAAGAAGAGGAGGAGGAGGAGGAGGATG

AATAA
``` mHMGB3 (C45S):
ATGGCTAAAGGTGACCCCAAGAAACCAAAGGGCAAGATGTCCGCTTATGCCTTCT

TTGTGCAGACATGCCAGAGAAGAACATAAGAAGAAAAACCCAGAGGTCCCTGTC

AATTTTGCGGAATTTTCCAAGAAGAGTTCTGAGAGGTGGAAGACGATGTCCGGGA

AAGAGAAATCTAAATTTGATGAAATGGCAAAGGCAGATAAAGTGCGCTATGATCG

GGAAATGAAGGATTATGGACCAGCTAAGGGAGGCAAGAAGAAGAAGGATCCTAA

TGCTCCCAAAAGGCCACCGTCTGGATTCTTCCTGTTCTGTTCAGAATTCCGCCCCA

AGATCAAATCCACAAACCCCGGCATCTCTATTGGAGACGTGGCAAAAAAGCTGGG

TGAGATGTGGAATAATTTAAATGACAGTGAAAAGCAGCCTTACATCACTAAGGCG

GCAAAGCTGAAGGAGAAGTATGAGAAGGATGTTGCTGACTATAAGTCGAAAGGA

AAGTTTGATGGTGCAAAGGGTCCTGCTAAAGTTGCCCGGAAAAAGGTGGAAGAG

GAAGATGAAGAAGAGGAGGAGGAAGAAGAGGAGGAGGAGGAGGAGGAGGATG

AATAA mHMGB3 (C104S):
ATGGCTAAAGGTGACCCCAAGAAACCAAAGGGCAAGATGTCCGCTTATGCCTTCT

TTGTGCAGACATGCCAGAGAAGAACATAAGAAGAAAAACCCAGAGGTCCCTGTC

AATTTTGCGGAATTTTCCAAGAAGTGCTCTGAGAGGTGGAAGACGATGTCCGGGA

AAGAGAAATCTAAATTTGATGAAATGGCAAAGGCAGATAAAGTGCGCTATGATCG

GGAAATGAAGGATTATGGACCAGCTAAGGGAGGCAAGAAGAAGAAGGATCCTAA

TGCTCCCAAAAGGCCACCGTCTGGATTCTTCCTGTTCAGCTCAGAATTCCGCCCCA

AGATCAAATCCACAAACCCCGGCATCTCTATTGGAGACGTGGCAAAAAAGCTGGG

TGAGATGTGGAATAATTTAAATGACAGTGAAAAGCAGCCTTACATCACTAAGGCG

GCAAAGCTGAAGGAGAAGTATGAGAAGGATGTTGCTGACTATAAGTCGAAAGGA

AAGTTTGATGGTGCAAAGGGTCCTGCTAAAGTTGCCCGGAAAAAGGTGGAAGAG

GAAGATGAAGAAGAGGAGGAGGAAGAAGAGGAGGAGGAGGAGGAGGAGGATG

AATAA mHMGB3 (C23S, C45S - double mutant):
ATGGCTAAAGGTGACCCCAAGAAACCAAAGGGCAAGATGTCCGCTTATGCCTTC

TTTGTGCAGACAAGTCAGAGAAGAACATAAGAAGAAAAACCCAGAGGTCCCTGT

CAATTTTGCGGAATTTTCCAAGAAGAGTTCTGAGAGGTGGAAGACGATGTCCGG

GAAAGAGAAATCTAAATTTGATGAAATGGCAAAGGCAGATAAAGTGCGCTATGA

TCGGGAAATGAAGGATTATGGACCAGCTAAGGGAGGCAAGAAGAAGAAGGATC

CTAATGCTCCCAAAAGGCCACCGTCTGGATTCTTCCTGTTCTGTTCAGAATTCCGC

CCCAAGATCAAATCCACAAACCCCGGCATCTCTATTGGAGACGTGGCAAAAAAG

CTGGGTGAGATGTGGAATAATTTAAATGACAGTGAAAAGCAGCCTTACATCACT

AAGGCGGCAAAGCTGAAGGAGAAGTATGAGAAGGATGTTGCTGACTATAAGTCG

AAAGGAAAGTTTGATGGTGCAAAGGGTCCTGCTAAAGTTGCCCGGAAAAAGGTG

GAAGAGGAAGATGAAGAAGAGGAGGAGGAAGAAGAGGAGGAGGAGGAGGAGG

AGGATGAATAA mHMGB3 (C23S, C104S - double mutant):
ATGGCTAAAGGTGACCCCAAGAAACCAAAGGGCAAGATGTCCGCTTATGCCTTC

TTTGTGCAGACAAGTCAGAGAAGAACATAAGAAGAAAAACCCAGAGGTCCCTGT

-continued

CAATTTTGCGGAATTTTCCAAGAAGTGCTCTGAGAGGTGGAAGACGATGTCCGG

GAAAGAGAAATCTAAATTTGATGAAATGGCAAAGGCAGATAAAGTGCGCTATGA

TCGGGAAATGAAGGATTATGGACCAGCTAAGGGAGGCAAGAAGAAGAAGGATC

CTAATGCTCCCAAAAGGCCACCGTCTGGATTCTTCCTGTTCAGCTCAGAATTCCG

CCCCAAGATCAAATCCACAAACCCCGGCATCTCTATTGGAGACGTGGCAAAAAA

GCTGGGTGAGATGTGGAATAATTTAAATGACAGTGAAAAGCAGCCTTACATCAC

TAAGGCGGCAAAGCTGAAGGAGAAGTATGAGAAGGATGTTGCTGACTATAAGTC

GAAAGGAAAGTTTGATGGTGCAAAGGGTCCTGCTAAAGTTGCCCGGAAAAAGGT

GGAAGAGGAAGATGAAGAAGAGGAGGAGGAAGAAGAGGAGGAGGAGGAGGAG

GAGGATGAATAA mHMGB3 (C45S, C104S - double mutant):
ATGGCTAAAGGTGACCCCAAGAAACCAAAGGGCAAGATGTCCGCTTATGCCTTCT

TTGTGCAGACATGCCAGAGAAGAACATAAGAAGAAAAACCCAGAGGTCCCTGTC

AATTTTGCGGAATTTTCCAAGAAGAGTTCTGAGAGGTGGAAGACGATGTCCGGGA

AAGAGAAATCTAAATTTGATGAAATGGCAAAGGCAGATAAAGTGCGCTATGATCG

GGAAATGAAGGATTATGGACCAGCTAAGGGAGGCAAGAAGAAGAAGGATCCTAA

TGCTCCCAAAAGGCCACCGTCTGGATTCTTCCTGTTCAGCTCAGAATTCCGCCCCA

AGATCAAATCCACAAACCCCGGCATCTCTATTGGAGACGTGGCAAAAAAGCTGGG

TGAGATGTGGAATAATTTAAATGACAGTGAAAAGCAGCCTTACATCACTAAGGCG

GCAAAGCTGAAGGAGAAGTATGAGAAGGATGTTGCTGACTATAAGTCGAAAGGA

AAGTTTGATGGTGCAAAGGGTCCTGCTAAAGTTGCCCGGAAAAAGGTGGAAGAG

GAAGATGAAGAAGAGGAGGAGGAAGAAGAGGAGGAGGAGGAGGAGGAGGATG

AATAA mHMGB3 (C23S, C45S, C104S - triple mutant):
ATGGCTAAAGGTGACCCCAAGAAACCAAAGGGCAAGATGTCCGCTTATGCCTTCT

TTGTGCAGACAAGTCAGAGAAGAACATAAGAAGAAAAACCCAGAGGTCCCTGTC

AATTTTGCGGAATTTTCCAAGAAGAGTTCTGAGAGGTGGAAGACGATGTCCGGGA

AAGAGAAATCTAAATTTGATGAAATGGCAAAGGCAGATAAAGTGCGCTATGATCG

GGAAATGAAGGATTATGGACCAGCTAAGGGAGGCAAGAAGAAGAAGGATCCTAA

TGCTCCCAAAAGGCCACCGTCTGGATTCTTCCTGTTCAGCTCAGAATTCCGCCCCA

AGATCAAATCCACAAACCCCGGCATCTCTATTGGAGACGTGGCAAAAAAGCTGGG

TGAGATGTGGAATAATTTAAATGACAGTGAAAAGCAGCCTTACATCACTAAGGCG

GCAAAGCTGAAGGAGAAGTATGAGAAGGATGTTGCTGACTATAAGTCGAAAGGA

AAGTTTGATGGTGCAAAGGGTCCTGCTAAAGTTGCCCGGAAAAAGGTGGAAGAG

GAAGATGAAGAAGAGGAGGAGGAAGAAGAGGAGGAGGAGGAGGAGGAGGATG

AATAA

Corresponding amino acid substitutions to yield a modified high mobility group-box 2 can be made at the cysteine residues at positions 45, 104, 164, and/or 178 based on the consensus sequence polypeptide of HMGB2 derived from a human:

MGKEIQLKPKANVSSYVHFLLNYRNKFKEQQPNTYVGFKEFSRKCSEKWR

SISKHEKAKYEALAKLDKARYQEEMMNYVGKRKKRRKRDPQEPRRPPSSF

-continued

LLFCQDHYAQLKRENPNWSVVQVAKATGKMWSTATDLEKHPYEQRVALLR

AKYFEELELYRKQCNARKKYRMSARNRCRGKRVRQS

Non-limiting exemplary sequences a modified high mobility group-box 2 domains include but are not limited to:

mHMGB4 (C45S):
MGKEIQLKPKANVSSYVHFLLNYRNKFKEQQPNTYVGFKEFSRKSSEKWRSISKHEK

AKYEALAKLDKARYQEEMMNYVGKRKKRRKRDPQEPRRPPSSFLLFCQDHYAQLK

RENPNWSVVQVAKATGKMWSTATDLEKHPYEQRVALLRAKYFEELELYRKQCNARK

KYRMSARNRCRGKRVRQS mHMGB4 (C104S):
MGKEIQLKPKANVSSYVHFLLNYRNKFKEQQPNTYVGFKEFSRKCSEKWRSISKHEK

AKYEALAKLDKARYQEEMMNYVGKRKKRRKRDPQEPRRPPSSFLLFSQDHYAQLK

RENPNWSVVQVAKATGKMWSTATDLEKHPYEQRVALLRAKYFEELELYRKQCNARK

KYRMSARNRCRGKRVRQS mHMGB4 (C164S):
MGKEIQLKPKANVSSYVHFLLNYRNKFKEQQPNTYVGFKEFSRKCSEKWRSISKHEK

AKYEALAKLDKARYQEEMMNYVGKRKKRRKRDPQEPRRPPSSFLLFCQDHYAQLK

RENPNWSVVQVAKATGKMWSTATDLEKHPYEQRVALLRAKYFEELELYRKQSNARK

KYRMSARNRCRGKRVRQS mHMGB4 (C178S):
MGKEIQLKPKANVSSYVHFLLNYRNKFKEQQPNTYVGFKEFSRKCSEKWRSISKHEK

AKYEALAKLDKARYQEEMMNYVGKRKKRRKRDPQEPRRPPSSFLLFCQDHYAQLK

RENPNWSVVQVAKATGKMWSTATDLEKHPYEQRVALLRAKYFEELELYRKQCNARK

KYRMSARNRSRGKRVRQS mHMGB4 (C45S, C104S - double mutant):
MGKEIQLKPKANVSSYVHFLLNYRNKFKEQQPNTYVGFKEFSRKSSEKWRSISKHEK

AKYEALAKLDKARYQEEMMNYVGKRKKRRKRDPQEPRRPPSSFLLFSQDHYAQLK

RENPNWSVVQVAKATGKMWSTATDLEKHPYEQRVALLRAKYFEELELYRKQCNARK

KYRMSARNRCRGKRVRQS mHMGB4 (C45S, C164S - double mutant):
MGKEIQLKPKANVSSYVHFLLNYRNKFKEQQPNTYVGFKEFSRKSSEKWRSISKHEK

AKYEALAKLDKARYQEEMMNYVGKRKKRRKRDPQEPRRPPSSFLLFCQDHYAQLK

RENPNWSVVQVAKATGKMWSTATDLEKHPYEQRVALLRAKYFEELELYRKQSNARK

KYRMSARNRCRGKRVRQS mHMGB4 (C45S, C178S - double mutant):
MGKEIQLKPKANVSSYVHFLLNYRNKFKEQQPNTYVGFKEFSRKSSEKWRSISKHEK

AKYEALAKLDKARYQEEMMNYVGKRKKRRKRDPQEPRRPPSSFLLFCQDHYAQLK

RENPNWSVVQVAKATGKMWSTATDLEKHPYEQRVALLRAKYFEELELYRKQCNARK

KYRMSARNRSRGKRVRQS mHMGB4 (C104S, C164S - double mutant):
MGKEIQLKPKANVSSYVHFLLNYRNKFKEQQPNTYVGFKEFSRKCSEKWRSISKHEK

AKYEALAKLDKARYQEEMMNYVGKRKKRRKRDPQEPRRPPSSFLLFSQDHYAQLK

RENPNWSVVQVAKATGKMWSTATDLEKHPYEQRVALLRAKYFEELELYRKQSNARK

KYRMSARNRCRGKRVRQS mHMGB4 (C104S, C178S - double mutant):
MGKEIQLKPKANVSSYVHFLLNYRNKFKEQQPNTYVGFKEFSRKCSEKWRSISKHEK

AKYEALAKLDKARYQEEMMNYVGKRKKRRKRDPQEPRRPPSSFLLFSQDHYAQLK

RENPNWSVVQVAKATGKMWSTATDLEKHPYEQRVALLRAKYFEELELYRKQCNARK

KYRMSARNRSRGKRVRQS mHMGB4 (C164S, C178S - double mutant):
MGKEIQLKPKANVSSYVHFLLNYRNKFKEQQPNTYVGFKEFSRKCSEKWRSISKHEK

AKYEALAKLDKARYQEEMMNYVGKRKKRRKRDPQEPRRPPSSFLLFCQDHYAQLK

RENPNWSVVQVAKATGKMWSTATDLEKHPYEQRVALLRAKYFEELELYRKQSNARK

KYRMSARNRSRGKRVRQS mHMGB4 (C45S, C104S, C164S - triple mutant):
MGKEIQLKPKANVSSYVHFLLNYRNKFKEQQPNTYVGFKEFSRKSSEKWRSISKHEK

AKYEALAKLDKARYQEEMMNYVGKRKKRRKRDPQEPRRPPSSFLLFSQDHYAQLK

RENPNWSVVQVAKATGKMWSTATDLEKHPYEQRVALLRAKYFEELELYRKQSNARK

KYRMSARNRCRGKRVRQS mHMGB4 (C45S, C104S, C178S - triple mutant):
MGKEIQLKPKANVSSYVHFLLNYRNKFKEQQPNTYVGFKEFSRKSSEKWRSISKHEK

AKYEALAKLDKARYQEEMMNYVGKRKKRRKRDPQEPRRPPSSFLLFSQDHYAQLK

RENPNWSVVQVAKATGKMWSTATDLEKHPYEQRVALLRAKYFEELELYRKQCNARK

KYRMSARNRSRGKRVRQS mHMGB4 (C45S, C164S, C178S - triple mutant):
MGKEIQLKPKANVSSYVHFLLNYRNKFKEQQPNTYVGFKEFSRKSSEKWRSISKHEK

AKYEALAKLDKARYQEEMMNYVGKRKKRRKRDPQEPRRPPSSFLLFCQDHYAQLK

RENPNWSVVQVAKATGKMWSTATDLEKHPYEQRVALLRAKYFEELELYRKQSNARK

KYRMSARNRSRGKRVRQS mHMGB4 (C104S, C164S, C178S) - triple mutant):
MGKEIQLKPKANVSSYVHFLLNYRNKFKEQQPNTYVGFKEFSRKCSEKWRSISKHEK

AKYEALAKLDKARYQEEMMNYVGKRKKRRKRDPQEPRRPPSSFLLFSQDHYAQLK

RENPNWSVVQVAKATGKMWSTATDLEKHPYEQRVALLRAKYFEELELYRKQSNARK

KYRMSARNRSRGKRVRQS mHMGB4 (C45S, C104S, C164S, C178S - quadruple mutant):
MGKEIQLKPKANVSSYVHFLLNYRNKFKEQQPNTYVGFKEFSRKSSEKWRSISKHEK

AKYEALAKLDKARYQEEMMNYVGKRKKRRKRDPQEPRRPPSSFLLFSQDHYAQLK

RENPNWSVVQVAKATGKMWSTATDLEKHPYEQRVALLRAKYFEELELYRKQSNARK

KYRMSARNRSRGKRVRQS

Nucleic acid sequences encoding these modified high mobility group-box 2 domains are also provided herein below:

mHMGB4 (C45S):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGAGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCTGCCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACATGTAAT

GCCAGGAAGAAGTACCGAATGTCAGCTAGAAACCGGTGCAGAGGGAAAAGAGTC

AGGCAGAGCTGA mHMGB4 (C104S):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGTGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTAGTCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACATGTAAT

GCCAGGAAGAAGTACCGAATGTCAGCTAGAAACCGGTGCAGAGGGAAAAGAGTC

AGGCAGAGCTGA mHMGB4 (C164S):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGTGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCTGCCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACAAGTAA

TGCCAGGAAGAAGTACCGAATGTCAGCTAGAAACCGGTGCAGAGGGAAAAGAGT

CAGGCAGAGCTGA mHMGB4 (C178S):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGTGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCTGCCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACATGTAAT

GCCAGGAAGAAGTACCGAATGTCAGCTAGAAACCGCAGCAGAGGGAAAAGAGT

CAGGCAGAGCTGA mHMGB4 (C45S, C104S - double mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGAGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCAGTCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACATGTAAT

GCCAGGAAGAAGTACCGAATGTCAGCTAGAAACCGGTGCAGAGGGAAAAGAGTC

AGGCAGAGCTGA mHMGB4 (C45S, C164S - double mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGAGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCTGCCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACAAGTAA

TGCCAGGAAGAAGTACCGAATGTCAGCTAGAAACCGGTGCAGAGGGAAAAGAGT

CAGGCAGAGCTGA mHMGB4 (C45S, C178S - double mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGAGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCTGCCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACATGTAAT

GCCAGGAAGAAGTACCGAATGTCAGCTAGAAACCGCAGCAGAGGGAAAAGAGT

CAGGCAGAGCTGA mHMGB4 (C104S, C164S - double mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGTGTTCGGAAAAATGGAGATCCATCTCAAAGCATGA

```
AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCAGTCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACAAGTAA

TGCCAGGAAGAAGTACCGAATGTCAGCTAGAAACCGGTGCAGAGGGAAAAGAGT

CAGGCAGAGCTGA mHMGB4 (C104S, C178S - double mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGTGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCAGTCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACATGTAAT

GCCAGGAAGAAGTACCGAATGTCAGCTAGAAACCGGAGCAGAGGGAAAAGAGT

CAGGCAGAGCTGA mHMGB4 (C164S, C178S - double mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGTGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCTGCCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACAAGTAA

TGCCAGGAAGAAGTACCGAATGTCAGCTAGAAACCGGAGCAGAGGGAAAAGAG

TCAGGCAGAGCTGA mHMGB4 (C45S, C104S, C164S - triple mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAAGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCAGTCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACAAGTAA
```

```
TGCCAGGAAGAAGTACCGAATGTCAGCTAGAAACCGGTGCAGAGGGAAAAGAGT

CAGGCAGAGCTGA mHMGB4 (C45S, C104S, C178S - triple mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGAGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCAGTCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACATGTAAT

GCCAGGAAGAAGTACCGAATGTCAGCTAGAAACCGGAGCAGAGGGAAAAGAGT

CAGGCAGAGCTGA mHMGB4 (C45S, C164S, C178S - triple mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGAGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCTGCCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACAAGTAA

TGCCAGGAAGAAGTACCGAATGTCAGCTAGAAACCGGAGCAGAGGGAAAAGAG

TCAGGCAGAGCTGA mHMGB4 (C104S, C164S, C178S) - triple mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGTGTTCGGAAAAATGGAGATCCATCTCAAAGCATGA

AAAGGCCAAATATGAAGCCCTGGCCAAACTCGACAAAGCCCGATACCAGGAAGA

AATGATGAATTATGTTGGCAAGAGGAAGAAACGGAGAAAGCGGGATCCCCAGGA

ACCCAGACGGCCTCCATCATCCTTCCTACTCTTCAGTCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACAAGTAA

TGCCAGGAAGAAGTACCGAATGTCAGCTAGAAACCGGAGCAGAGGGAAAAGAG

TCAGGCAGAGCTGA mHMGB4 (C45S, C104S, C164S, C178S - quadruple mutant):
ATGGGAAAAGAAATCCAGCTAAAGCCTAAGGCAAATGTCTCTTCTTACGTTCACTT

TTTGCTGAATTACAGAAACAAATTCAAGGAGCAGCAGCCAAATACCTATGTTGGCT

TTAAAGAGTTCTCTAGAAAGAGTTCGGAAAAATGGAGATCCATCTCAAAGCATGA

AAAGGCCAAATATGAAGCCCTGGCCAAACTCGACAAAGCCCGATACCAGGAAGA
```

-continued

```
AATGATGAATTATGTTGGCAAGAGGAAGAAACGGAGAAAGCGGGATCCCCAGGA

ACCCAGACGGCCTCCATCATCCTTCCTACTCTTCAGTCAAGACCACTATGCTCAGC

TGAAGAGGGAGAACCCGAACTGGTCGGTGGTGCAGGTGGCCAAGGCCACAGGG

AAGATGTGGTCAACAGCGACAGACCTGGAGAAGCACCCTTATGAGCAAAGAGTG

GCTCTCCTGAGAGCTAAGTACTTCGAGGAACTTGAACTCTACCGTAAACAAGTAA

TGCCAGGAAGAAGTACCGAATGTCAGCTAGAAACCGCAGCAGAGGGAAAAGAG

TCAGGCAGAGCTGA
```

Modes for Carrying Out the Disclosure

Applicants demonstrate herein that while the DNABII proteins stabilize the eDNA dependent extracellular matrix of biofilms, recombinant HMGB1 (rHMGB1) disrupts in vitro preformed bacterial biofilms (Table 1), clear NTHI biofilms from the chinchilla middle ear in an experimental model of otitis media (OM) (FIGS. 1A-1B) and inhibit *Burkholderia cenocepacia* biofilm development in the murine airways that directly resulted in reduced bacterial burden (FIGS. 2A-2D).

Although rHMGB1 was demonstrated to be effective at disrupting biofilms in vitro and in vivo, it is also well documented to induce a robust inflammatory response that can potentially be detrimental to the host. Several post-translational modifications (PTMs) including acetylation, phosphorylation, methylation, glycosylation, ADP-ribosylation, and oxidation of cysteine residues have been described for HMGB1 that modulate its location (nucleus, cytoplasm or extracellular), function, and ability to bind DNA (reviewed in (Kang et al. 2014)). Human HMGB1 contains three cysteine residues at positions 23, 45, and 106 and the oxidation of the cysteine residues impacts its inflammatory properties (Kazama et al. 2008). While HMGB1 containing C106 thiol group and a C23-C45 disulfide bond triggers inflammation, terminally oxidized cysteines promote inflammation resolution (Yang et al. 2012).

In the disclosed study, Applicants generated a variant form of HMGB1 (mHMGB1) wherein Applicants substituted the cysteine at position 45 with serine (C45S). Applicants demonstrated that while mHMGB1 (C45S) is effective at disrupting in vitro preformed biofilms formed by multiple human pathogens, clearing NTHI biofilms in an experimental model of OM and reducing the *B. cenocepacia* bacterial burden in the murine airways, it failed to enhance the inflammatory response. Applicants' data suggest that Applicants have generated a HMGB1 variant (mHMGB1) that retains the desirable antibiofilm function against multiple human pathogens but is defective at mounting the undesirable robust pro-inflammatory response. Moreover, this study suggests that other equivalent modifications of HMGB1, such as C23S and C106S may yield similar results. Thus, Applicants generate a triple-mutant HMGB1 comprising the modifications C23S, C45S, and C106S and further mutant HMGB1 comprising one or more modifications selected from the group of C23S, C45S, and C106S.

Applicants' approach is an improvement over current technologies in that it does not rely upon compounds with bactericidal activities, which apply additional pressures on bacteria to develop resistance mechanisms, but rather targets the biofilm extracellular matrix resulting in disruption of biofilms leading to resolution of disease in the absence of excessive inflammation.

This method and composition of matter is useful in the treatment of multiple, diverse biofilm-mediated infections including but not limited to otitis media, urinary tract infections, pneumonia, gingivitis, peri-implantitis, periodontitis, cystic fibrosis, endocarditis and burn wound infections.

This method and composition of matter, in combination with an antibiotic or other antimicrobial, is useful to "sterilize" the target site of device insertion to prevent device-associated infections.

C45S recombinant HMGB1 or Modified HMGB1 (C45S) ("mHMGB1 (C45S)") has been shown to disrupt pre-existing biofilms both in vitro and in vivo (in two mammalian models). Dispersal of large amount of bacteria from a biofilm into a planktonic state in vivo could have potential disadvantages in that now these planktonic bacteria may be able to gain access to other sites that they did not have access to before resulting in potential second site infections. Also, this dispersal effect could result in sepsis. None of these consequences has been observed with mHMGB1 and there are means to avoid these potential limitations in addition to the fact that depending on the site of the biofilm infection, these potential pitfalls may be moot. Indeed, it appears that the C45S mutation increases the affinity of the molecule to branched DNA structures (extracellular DNA within bacterial biofilms are believed to contain these structures) and also attenuates its inflammatory response and hence gives a better therapeutic response.

Accordingly, aspects disclosed herein relate to a modified high mobility group-box 1 domain comprising one or more or all substitutions selected from the group of C23S, C45S, and C106S, an isolated or recombinant polynucleotide encoding the modified high mobility group-box 1 domain, a vector comprising the isolated or recombinant polynucleotide, and a composition comprising an effective amount of the modified high mobility group-box 1 domain and/or the aforementioned isolated or recombinant polynucleotide and/or the aforementioned vector. In one aspect the polynucleotide is DNA, and in another aspect the polynucleotide is RNA. Also provided are the recombinant methods to produce the mHMGB1 polypeptides by expressing the polynucleotides in prokaryotic or eukaryotic systems. In a further aspect, the protein produced in the system is isolated. Thus, this disclosure also provides polypeptides produced in prokaryotic and eukaryotic host cell systems. In some embodiments, the modified high mobility group-box 1 domain comprises the substitution C45S. In some embodiments, the modified high mobility group-box 1 domain comprises the substitutions C23S, C45S, and C106S.

Further aspects relate to a method for inhibiting, competing or titrating the binding of a deoxyribonucleic acid B II (DNABII) polypeptide to a microbial DNA in a biofilm, comprising contacting the microbial DNA in the biofilm with an effective amount of an isolated or recombinant polypeptide comprising a modified high mobility group-box 1 domain comprising one or more substitutions selected from the group of C23S, C45S, and C106S or any one or more of the compositions disclosed above thereby inhibiting, competing or titrating the binding of the DNABII polypeptide to the microbial DNA. In some embodiments, the modified high mobility group-box 1 domain comprises the substitution C45S. In some embodiments, the modified high mobility group-box 1 domain comprises the substitutions C23S, C45S, and C106S. In some embodiments, the contacting is in vitro or in vivo. In some embodiments, the biofilm is formed by *Burkholderia cenocepacia, Enterobacter* spp., *Staphylococcus aureus, Klebsiella pneumoniae, Acinetobacter baumanii, Pseudomonas aeruginosa, Enterococcus faecium*, Uropathogenic *Escherichia coli* (UPEC), Non-typeable *Haemophilus influenzae* (NTHI), and/or *Aggregatibacter actinomycetemcomitans*. In some embodiments, the method further comprises administering, optionally coating, the surface with an effective amount of an antibiotic.

Still further aspects relate to a method of preventing formation of a biofilm on a surface, comprising contacting, optionally coating, the surface with an effective amount of an isolated or recombinant polypeptide comprising a modified high mobility group-box 1 domain comprising one or more or all substitutions selected from the group of C23S, C45S, and C106S or any one or more of the compositions disclosed above thereby inhibiting, competing or titrating the binding of a DNABII polypeptide to a microbial DNA during biofilm formation. In some embodiments, the modified high mobility group-box 1 domain comprises the substitution C45S. In some embodiments, the modified high mobility group-box 1 domain comprises the substitutions C23S, C45S, and C106S. In some embodiments, the contacting is in vitro or in vivo. In some embodiments, the biofilm is formed by *Burkholderia cenocepacia, Enterobacter* spp., *Staphylococcus aureus, Klebsiella pneumoniae, Acinetobacter baumanii, Pseudomonas aeruginosa, Enterococcus faecium*, Uropathogenic *Escherichia coli* (UPEC), Non-typeable *Haemophilus influenzae* (NTHI), and/or *Aggregatibacter actinomycetemcomitans*. In some embodiments, the method further comprises administering, optionally coating, the surface with an effective amount of an antibiotic.

Additional aspects relate to a method for preventing or treating a microbial infection in a subject that produces a biofilm, comprising administering an effective amount of an isolated or recombinant polypeptide comprising a modified high mobility group-box 1 domain comprising one or more substitutions selected from the group of C23S, C45S, and C106S or any one or more of the compositions disclosed above thereby inhibiting, competing or titrating the binding of a DNABII polypeptide to a microbial DNA. In some embodiments, the modified high mobility group-box 1 domain comprises the substitution C45S. In some embodiments, the modified high mobility group-box 1 domain comprises the substitutions C23S, C45S, and C106S. In some embodiments, the biofilm is formed by *Burkholderia cenocepacia, Enterobacter* spp., *Staphylococcus aureus, Klebsiella pneumoniae, Acinetobacter baumanii, Pseudomonas aeruginosa, Enterococcus faecium*, Uropathogenic *Escherichia coli* (UPEC), Non-typeable *Haemophilus influenzae* (NTHI), and/or *Aggregatibacter actinomycetemcomitans*. In some embodiments, the method further comprises administering, an effective amount of an antibiotic.

It is appreciated that among the equivalents to a modified high mobility group-box 1 domain are modified high mobility group-box 2, modified high mobility group-box 3, and modified high mobility group-box 4 comprising cysteine to serine substitutions at one or more amino acid positions corresponding to C23S, C45S, and C106S of a modified high mobility group box 1. For modified high mobility group-box 2 the corresponding cysteine residues are found at position 23, 45, and 106; for modified high mobility group-box 3 the corresponding cysteine residues are found at position 23, 45, and 104; and for modified high mobility group-box 4 the corresponding cysteine residues are found at position 45, 104, 164, and 178. Thus, Applicants believe the aforementioned aspects disclosed with respect to a modified high mobility group-box 1 comprising one or more substitutions selected from the group of C23S, C45S, and C106S are equally applicable to the aforementioned high mobility group-box species with one or more cysteine to serine substitutions at the mentioned positions, e.g., a modified high mobility group-box 2 comprising one or more substitutions selected from the group of C23S, C45S, and C106S; a modified high mobility group-box 3 comprising one or more substitutions selected from the group of C23S, C45S, and C104S; and a modified high mobility group-box 4 comprising one or more substitutions selected from the group of C45S, C104S, C164S, and C178S.

Modes of Carrying Out the Disclosure

Polypeptides

Aspects disclosed herein relate to a modified high mobility group-box 1 domain comprising one or more substitutions selected from the group of C23S, C45S, and C106S. In some embodiments, the modified high mobility group-box 1 domain comprises the substitution C45S. In some embodiments, the modified high mobility group-box 1 domain comprises one, two or all three substitutions C23S, C45S, and C106S.

It is appreciated that among the equivalents to a modified high mobility group-box 1 domain are modified high mobility group-box 2, modified high mobility group-box 3, and modified high mobility group-box 4 comprising cysteine to serine substitutions at one or more amino acid positions corresponding to C23S, C45S, and C106S of a modified high mobility group box 1. For modified high mobility group-box 2 the corresponding cysteine residues are found at position 23, 45, and 106; for modified high mobility group-box 3 the corresponding cysteine residues are found at position 23, 45, and 104; and for modified high mobility group-box 4 the corresponding cysteine residues are found at position 45, 104, 164, and 178. Thus, Applicants believe the aforementioned polypeptide aspects disclosed with respect to a modified high mobility group-box 1 comprising one or more substitutions selected from the group of C23S, C45S, and C106S are equally applicable to the aforementioned high mobility group-box species with one or more cysteine to serine substitutions at the mentioned positions, e.g., a modified high mobility group-box 2 comprising one or more substitutions selected from the group of C23S, C45S, and C106S; a modified high mobility group-box 3 comprising one or more substitutions selected from the group of C23S, C45S, and C104S; and a modified high mobility group-box 4 comprising one or more substitutions selected from the group of C45S, C104S, C164S, and C178S.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody and standard techniques such as gel filtration, ion-exchange, reversed-phase and affinity chromatography. For such methodology, see for example Deutscher et al. (1999) Guide To Protein Purification: Methods In Enzymology (Vol. 182, Academic Press). Accordingly, this invention also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

Alternatively, the proteins and polypeptides can be obtained by well-known recombinant methods or mutagenesis as described, for example, in for example Sambrook et al. (2012) supra, using the host cell and vector systems described herein.

The polypeptides of this invention also can be combined with various solid phase carriers, such as an implant, a stent, a paste, a gel, a dental implant or a medical implant or liquid phase carriers, such as beads, sterile or aqueous solutions, pharmaceutically acceptable carriers, suspensions or emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of E. coli, mutant derivatives of cholera toxin, CPG oligonucleotides and adjuvants derived from squalene.

Polynucleotides and Vectors

Aspects disclosed herein relate to an isolated or recombinant polynucleotide encoding the modified high mobility group-box 1 domain comprising one or more substitutions selected from the group of C23S, C45S, and C106S and/or a vector comprising the isolated or recombinant polynucleotide. In some embodiments, the modified high mobility group-box 1 domain comprises the substitution C45S. In some embodiments, the modified high mobility group-box 1 domain comprises the substitutions C23S, C45S, and C106S.

In general methods of packaging genetic material such as DNA or RNA into one or more vectors is well known in the art. In some embodiments, the modified high mobility group-box 1 domain comprises the substitution C45S. In some embodiments, the modified high mobility group-box 1 domain comprises the substitutions C23S, C45S, and C106S. For example, the genetic material may be packaged using a packaging vector and cell lines and introduced via traditional recombinant methods.

It is appreciated that among the equivalents to a modified high mobility group-box 1 domain are modified high mobility group-box 2, modified high mobility group-box 3, and modified high mobility group-box 4 comprising cysteine to serine substitutions at one or more amino acid positions corresponding to C23S, C45S, and C106S of a modified high mobility group box 1. For modified high mobility group-box 2 the corresponding cysteine residues are found at position 23, 45, and 106; for modified high mobility group-box 3 the corresponding cysteine residues are found at position 23, 45, and 104; and for modified high mobility group-box 4 the corresponding cysteine residues are found at position 45, 104, 164, and 178. Thus, Applicants believe the isolated polynucleotide and vector aspects disclosed with respect to a modified high mobility group-box 1 comprising one or more substitutions selected from the group of C23S, C45S, and C106S are equally applicable to the aforementioned high mobility group-box species with one or more cysteine to serine substitutions at the mentioned positions, e.g., a modified high mobility group-box 2 comprising one or more substitutions selected from the group of C23S, C45S, and C106S; a modified high mobility group-box 3 comprising one or more substitutions selected from the group of C23S, C45S, and C104S; and a modified high mobility group-box 4 comprising one or more substitutions selected from the group of C45S, C104S, C164S, and C178S.

In some embodiments, the packaging vector may include, but is not limited to retroviral vector, lentiviral vector, adenoviral vector, and adeno-associated viral vector (optionally AAV8). The packaging vector contains elements and sequences that facilitate the delivery of genetic materials into cells. For example, the retroviral constructs are packaging plasmids comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3'LTR, but encodes a foreign polyadenylation site, for example the SV40 polyadenylation site, and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter.

The retroviral packaging plasmid may consist of two retroviral helper DNA sequences encoded by plasmid based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytrophic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell. Similar vector based systems may employ other vectors such as sleeping beauty vectors or transposon elements.

The resulting packaged expression systems may then be introduced via an appropriate route of administration, discussed in detail with respect to the method aspects disclosed herein.

Compositions

Further aspects relate to a composition comprising an effective amount of the modified high mobility group-box 1 domain one or more substitutions selected from the group of C23S, C45S, and C106S and/or the aforementioned isolated or recombinant polynucleotide and/or the aforementioned vector. In some embodiments, the modified high mobility group-box 1 domain comprises the substitution C45S. In some embodiments, the modified high mobility group-box 1 domain comprises the substitutions C23S, C45S, and C106S.

It is appreciated that among the equivalents to a modified high mobility group-box 1 domain are modified high mobility group-box 2, modified high mobility group-box 3, and modified high mobility group-box 4 comprising cysteine to serine substitutions at one or more amino acid positions corresponding to C23S, C45S, and C106S of a modified high mobility group box 1. For modified high mobility group-box 2 the corresponding cysteine residues are found at position 23, 45, and 106; for modified high mobility group-box 3 the corresponding cysteine residues are found at position 23, 45, and 104; and for modified high mobility group-box 4 the corresponding cysteine residues are found at position 45, 104, 164, and 178. Thus, Applicants believe the composition aspects disclosed with respect to a modified high mobility group-box 1 comprising one or more substitutions selected from the group of C23S, C45S, and C106S are equally applicable to the aforementioned high mobility group-box species with one or more cysteine to serine substitutions at the mentioned positions, e.g. a modified high mobility group-box 2 comprising one or more substitutions selected from the group of C23S, C45S, and C106S; a modified high mobility group-box 3 comprising one or more substitutions selected from the group of C23S, C45S, and C104S; and a modified high mobility group-box 4 comprising one or more substitutions selected from the group of C45S, C104S, C164S, and C178S.

Briefly, pharmaceutical compositions of the present disclosure including but not limited to any one of the claimed compositions may comprise a modified high mobility group-box 1 domain as described herein, in combination with one or more pharmaceutically or physiologically acceptable carriers, diluents or excipients.

Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding antibodies, or will be able to ascertain such, using routine experimentation.

Such compositions may also comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Administration of the compositions can be effected in one dose, continuously or intermittently throughout the course of treatment. Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the agents are known in the art. In a further aspect, the cells and composition of the disclosure can be administered in combination with other treatments.

The vectors, recombinant expression systems, and/or compositions are administered to the host using methods known in the art. This administration of the compositions of the disclosure can be done to generate an animal model of the desired disease, disorder, or condition for experimental and screening assays.

Briefly, pharmaceutical compositions of the present disclosure including but not limited to any one of the claimed compositions may comprise one or more vectors or recombinant expression systems as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Pharmaceutical compositions of the present disclosure may be administered in a manner appropriate to the disease, disorder, or condition to be treated or prevented. The quantity and frequency of administration will be determined by such factors as the condition of the patient, and the type and severity of the patient's disease, although appropriate dosages may be determined by clinical trials.

Therapeutic Methods

Aspects disclosed herein relate to therapeutic methods. For example, aspects relate to a method for inhibiting, competing or titrating the binding of a deoxyribonucleic acid B II (DNABII) polypeptide to a microbial DNA in a biofilm, comprising contacting the microbial DNA in the biofilm with an effective amount of an isolated or recombinant polypeptide comprising a modified high mobility group-box 1 domain comprising one or more substitutions selected from the group of C23S, C45S, and C106S or any one or more of the compositions disclosed above thereby inhibiting, competing or titrating the binding of the DNABII polypeptide to the microbial DNA. In some embodiments, the modified high mobility group-box 1 domain comprises the substitution C45S. In some embodiments, the modified high mobility group-box 1 domain comprises the substitutions C23S, C45S, and C106S. In some embodiments, the contacting is in vitro or in vivo.

Further aspects relate to a method of preventing formation of a biofilm on a surface, comprising contacting, optionally coating, the surface with an effective amount of an isolated or recombinant polypeptide comprising a modified high mobility group-box 1 domain comprising one or more substitutions selected from the group of C23S, C45S, and C106S or any one or more of the compositions disclosed above thereby inhibiting, competing or titrating the binding of a DNABII polypeptide to a microbial DNA during biofilm formation. In some embodiments, the modified high mobility group-box 1 domain comprises the substitution C45S. In some embodiments, the modified high mobility group-box 1 domain comprises the substitutions C23S, C45S, and C106S. In some embodiments, the contacting is in vitro or in vivo.

Additional aspects relate to a method for preventing or treating a microbial infection in a subject that produces a biofilm, comprising administering an effective amount of an isolated or recombinant polypeptide comprising a modified high mobility group-box 1 domain comprising one or more substitutions selected from the group of C23S, C45S, and C106S or any one or more of the compositions disclosed above thereby inhibiting, competing or titrating the binding of a DNABII polypeptide to a microbial DNA. In some embodiments, the modified high mobility group-box 1 domain comprises the substitution C45S. In some embodiments, the modified high mobility group-box 1 domain comprises the substitutions C23S, C45S, and C106S.

In some aspect, the polypeptide comprising a modified high mobility group-box 1 domain comprising one or more substitutions selected from the group of C23S, C45S, and C106S comprises or alternatively consists essentially of, or yet further consists of a biological equivalent to any polypeptide recited above.

It is appreciated that among the equivalents to a modified high mobility group-box 1 domain are modified high mobility group-box 2, modified high mobility group-box 3, and modified high mobility group-box 4 comprising cysteine to serine substitutions at one or more amino acid positions corresponding to C23S, C45S, and C106S of a modified high mobility group box 1. For modified high mobility group-box 2 the corresponding cysteine residues are found at position 23, 45, and 106; for modified high mobility group-box 3 the corresponding cysteine residues are found at position 23, 45, and 104; and for a modified high mobility group-box 4 the corresponding cysteine residues are found at position 45, 104, 164, and 178. Thus, Applicants believe the method aspects disclosed with respect to a modified high mobility group-box 1 comprising one or more substitutions selected from the group of C23S, C45S, and C106S are equally applicable to the aforementioned high mobility group-box species with one or more cysteine to serine substitutions at the mentioned positions, e.g., a modified high mobility group-box 2 comprising one or more substitutions selected from the group of C23S, C45S, and C106S; a modified high mobility group-box 3 comprising one or more substitutions selected from the group of C23S, C45S, and C104S; and a modified high mobility group-box 4 comprising one or more substitutions selected from the group of C45S, C104S, C164S, and C178S.

In some aspects, the isolated or recombinant protein is a mammalian protein. In a particular aspect, the mammalian protein is a human protein.

Any of the above method can further comprise or alternatively consists essentially of, or yet further consists of administering to the subject an effective amount of one or more of an antimicrobial, an antigenic peptide or an adjuvant. The subject, in one aspect, is a non-human animal or a human patient.

The polypeptide is administered by a method comprising topically, transdermally, sublingually, rectally, vaginally, ocularly, subcutaneous, intramuscularly, intraperitoneally, urethrally, intranasally, by inhalation or orally.

In some aspects, the subject is a pediatric patient and the polypeptide is administered in a formulation for the pediatric patient.

In any of the above embodiments, the biofilm can comprise microbial DNA from a microorganism identified in Table 1.

In one embodiment, the polypeptide is administered locally to the microbial infection.

In one embodiment, the present disclosure provides a method for inducing or providing an immune response in a subject in need thereof, comprising or alternatively consisting essentially of, or yet further consisting of administering to the subject an effective amount of a the modified high mobility group-box 1 domain comprising one or more substitutions selected from the group of C23S, C45S, and C106S. In another embodiment, the administration is local to where the immune response is desired. Examples of modified high mobility group-box 1 domains comprising one or more substitutions selected from the group of C23S, C45S, and C106S are described above. In some embodiments, the modified high mobility group-box 1 domain comprises the substitution C45S. In some embodiments, the modified high mobility group-box 1 domain comprises the substitutions C23S, C45S, and C106S.

The isolated or recombinant protein can be a mammalian protein or in a particular aspect, a human protein. The subject, in some aspects, is a non-human animal or a human patient.

The agents and compositions of this invention can be concurrently or sequentially administered with other antimicrobial agents and/or surface antigens. In one particular aspect, administration is locally to the site of the infection. Other non-limiting examples of administration include by one or more method comprising transdermally, sublingually, rectally, vaginally, ocularly, subcutaneous, intramuscularly, intraperitoneally, intranasally, by inhalation or orally.

Also provided, in one embodiment, is use of any of the above described polypeptide comprising or alternatively consisting essentially of, or yet further consisting of modified high mobility group-box 1 domain comprising one or more substitutions selected from the group of C23S, C45S, and C106S for the manufacture of a medicament in breaking down a biofilm or inhibiting, preventing or treating a microbial infection that produces a biofilm. In some embodiments, the modified high mobility group-box 1 domain comprises the substitution C45S. In some embodiments, the modified high mobility group-box 1 domain comprises the substitutions C23S, C45S, and C106S.

For some of these methods the contacting can be performed in vitro or in vivo. When the contacting is in vitro, the method provides a means to determine efficacy of the agents of this invention prior to animal or clinical studies and can be used to determine if the agents of this invention work synergistically with additional antimicrobials. When performed in vivo in an animal model, the method provides a means to determine efficacy of the agents of this invention prior to studies in human patients and can be used to determine if the agents of this invention work synergistically with additional antimicrobials, e.g., antibiotics.

Microbial infections and disease that can be treated by the methods of this invention include infection by the organisms identified in Table 1, e.g., *Burkholderia cenocepacia, Enterobacter* spp., *Staphylococcus aureus, Klebsiella pneumoniae, Acinetobacter baumanii, Pseudomonas aeruginosa, Enterococcus faecium*, Uropathogenic *Escherichia coli* (UPEC), Non-typeable *Haemophilus influenzae* (NTHI), or *Aggregatibacter actinomycetemcomitans*. These microbial infections may be present in the upper, mid or lower airway (otitis, sinusitis or bronchitis) but also exacerbations of chronic obstructive pulmonary disease (COPD), chronic cough, complications of and/or primary cause of cystic fibrosis (CF) and community acquired pneumonia (CAP).

Infections might also occur in the oral cavity (caries, periodontitis) and caused by *Streptococcus mutans, Porphyromonas gingivalis, Aggregatibacter actinomycetemcomitans*. Infections might also be localized to the skin (abscesses, 'staph' infections, impetigo, secondary infection of burns, Lyme disease) and caused by *Staphylococcus aureus, Staphylococcus epidermidis, Pseudomonas aeruginosa* and *Borrelia burdorferi*. Infections of the urinary tract (UTI) can also be treated and are typically caused by *Escherichia coli*. Infections of the gastrointestinal tract (GI) (diarrhea, cholera, gall stones, gastric ulcers) are typically caused by *Salmonella enterica* serovar, *Vibrio cholerae* and *Helicobacter pylori*. Infections of the genital tract include and are typically caused by *Neisseria gonorrhoeae*. Infections can be of the bladder or of an indwelling device caused by *Enterococcus faecalis*. Infections associated with implanted prosthetic devices, such as artificial hip or knee replacements or dental implants or medical devices such as pumps or monitoring systems, typically caused by a variety of bacteria, can be treated by the methods of this invention. These devices can be coated or conjugated to an agent as described herein.

Infections caused by *Streptococcus agalactiae* are the major cause of bacterial septicemia in newborns. Such infections can also be treated by the methods of this invention. Likewise, infections caused by *Neisseria meningitidis* which can cause meningitis can also be treated.

Thus, routes of administration applicable to the methods of the invention include intranasal, intramuscular, intratracheal, subcutaneous, intradermal, topical application, intravenous, rectal, nasal, oral and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes. In general, routes of administration suitable for the methods of the invention include, but are not limited to, enteral, parenteral or inhalational routes.

Parenteral routes of administration other than inhalation administration include, but are not limited to, topical, transdermal, subcutaneous, intramuscular, intraorbital, intracapsular, intraspinal, intrasternal and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The compounds of the invention can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods of the invention, the active will be administered orally on a continuous, daily basis, at least once per day (QD) and in various embodiments two (BID), three (TID) or even four times a day. Typically, the therapeutically effective daily dose will be at least about 1 mg, or at least about 10 mg, or at least about 100 mg or about 200-about 500 mg and sometimes, depending on the compound, up to as much as about 1 g to about 2.5 g.

Dosing of can be accomplished in accordance with the methods of the invention using capsules, tablets, oral suspension, suspension for intra-muscular injection, suspension for intravenous infusion, gel or cream for topical application or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Combination Therapy

The compositions and related methods of the present invention may be used in combination with the administration of other therapies. These include, but are not limited to, the administration of DNase enzymes, antibiotics, antimicrobials, or other antibodies.

In some embodiments, the methods and compositions include a deoxyribonuclease (DNase) enzyme that acts synergistically with a composition of this disclosure, e.g., a DNase. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current invention include minocycline, amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. One example of an antibody useful in combination with the methods and compositions described herein is an antibody directed against an unrelated outer membrane protein (e.g., OMP P5). Treatment with this antibody alone does not debulk a biofilm in vitro. Combined therapy with this antibody and a biofilm reducing agent results in a greater effect than that which could be achieved by either reagent used alone at the same concentration. Other antibodies that may produce a synergistic effect when combined with a biofilm reducing agent or methods to reduce a biofilm include anti-rsPilA, anti-OMP26, anti-OMP P2, and anti-whole OMP preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formulation or as a separate formulation.

Antibodies and Derivatives Thereof

This disclosure also provides an antibody that binds and/or specifically recognizes a modified high mobility group-box 1 comprising one or more substitutions selected from the group of C23S, C45S, and C106S disclosed herein.

It is appreciated that among the equivalents to a modified high mobility group-box 1 domain are modified high mobility group-box 2, modified high mobility group-box 3, and modified high mobility group-box 4 comprising cysteine to serine substitutions at one or more amino acid positions corresponding to C23S, C45S, and C106S of a modified high mobility group box 1. For modified high mobility group-box 2 the corresponding cysteine residues are found at position 23, 45, and 106; for modified high mobility group-box 3 the corresponding cysteine residues are found at position 23, 45, and 104; and for a modified high mobility group-box 4 the corresponding cysteine residues are found at position 45, 104, 164, and 178. Thus, Applicants believe the antibody aspects disclosed with respect to a modified high mobility group-box 1 comprising one or more substitutions selected from the group of C23S, C45S, and C106S are equally applicable to the aforementioned high mobility group-box species with one or more cysteine to serine substitutions at the mentioned positions, e.g. a modified high mobility group-box 2 comprising one or more substitutions selected from the group of C23S, C45S, and C106S; a modified high mobility group-box 3 comprising one or more substitutions selected from the group of C23S, C45S, and C104S; and a modified high mobility group-box 4 comprising one or more substitutions selected from the group of C45S, C104S, C164S, and C178S.

The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof. In one aspect, the fragment comprises, or alternatively consists essentially of, or yet further consists of the CDR of the antibody, examples of such are provided herein. In one aspect, the antibody is detectably labeled or further comprises a detectable label conjugated to it. Also provided is a hybridoma cell line that produces a monoclonal antibody disclosed herein. Compositions comprising or alternatively consisting essentially of or yet further, consisting of one or more of the above embodiments are further provided herein. Further provided are polynucleotides that encode the amino acid sequence of the antibodies and fragments as well as methods to produce recombinantly or chemically synthesize the antibody polypeptides and fragments thereof. The antibody polypeptides can be produced in a eukaryotic or prokaryotic cell, or by other methods known in the art and described herein.

Antibodies also can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, those at the following web addresses e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161) that are capable of producing a repertoire of human antibodies, as known in the art and/or as described herein. Such techniques, include, but are not limited to, ribosome display, e.g., Wanes et al. (1997) Proc. Natl. Acad. Sci. USA, 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052, Wen et al, (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al, (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody or fragment thereof disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fe-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or to reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e., the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

In some of the aspects of the antibodies provided herein, the antibody binds a DNABII protein with a dissociation constant ($K_D$) of less than $10^{-4}$M, $10^{-5}$M, $10^{-6}$ M, $10^{-7}$M, $10^{-8}$M, $10^{-9}$M, $10^{-10}$ M, $10^{-11}$ M, or $10^{-12}$ M.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody is selected from the group consisting of Fab, F(ab')2, Fab', scF$_v$, and F$_v$.

In some of the aspects of the antibodies provided herein, the antibody comprises an Fc domain. In some of the aspects of the antibodies provided herein, the antibody is a rabbit antibody. In some of the aspects of the antibodies provided herein, the antibody is a human or humanized antibody or is non-immunogenic in a human.

In some of the aspects of the antibodies provided herein, the antibody comprises a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.

2) Amino acids with acidic side chains: aspartic acid, glutamic acid

3) Amino acids with uncharged polar side chains: asparagine, glutamine, serine, threonine, tyrosine.

4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind with similar specificity and sensitivity profiles as the disclosed antibodies. This may be tested by way of the binding assays.

The constant regions of antibodies may also be varied. For example, antibodies may be provided with Fc regions of any isotype: IgA (IgA1, IgA2), IgD, IgE, IgG (IgG1, IgG2, IgG3, IgG4) or IgM. Non-limiting examples of constant region sequences include:

Human IgD constant region, Uniprot: P01880

SEQ ID NO. 37

APTKAPDVFPIISGCRHPKDNSPVVLACLITGYHPTSVTVTWYMGTQSQPQRTFPEIQ

RRDSYYMTSSQLSTPLQQWRQGEYKCVVQHTASKSKKEIFRWPESPKAQASSVPTA

QPQAEGSLAKATTAPATTRNTGRGGEEKKKEKEKEEQEERETKTPECPSHTQPLGVY

LLTPAVQDLWLRDKATFTCFVVGSDLKDAHLTWEVAGKVPTGGVEEGLLERHSNG

SQSQHSRLTLPRSLWNAGTSVTCTLNHPSLPPQRLMALREPAAQAPVKLSLNLLASS

DPPEAASWLLCEVSGFSPPNILLMWLEDQREVNTSGFAPARPPPQPGSTTFWAWSVL

RVPAPPSPQPATYTCVVSHEDSRTLLNASRSLEVSYVTDHGPMK

Human IgG1 constant region, Uniprot: P01857

SEQ ID NO. 38

ASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

Human IgG2 constant region, Uniprot: P01859

SEQ ID NO. 39

ASTKGPSVFPLAPCSRSTSESTAALGCLVKDYFPEPVTVSWNSGALTSGVHTFPAVLQ

SSGLYSLSSVVTVPSSNFGTQTYTCNVDHKPSNTKVDKTVERKCCVECPPCPAPPVA

GPSVFLFPPKPKDTLMISRTPEVTCVVVDVSHEDPEVQFNWYVDGVEVHNAKTKPR

EEQFNSTFRVVSVLTVVHQDWLNGKEYKCKVSNKGLPAPIEKTISKTKGQPREPQVY

TLPPSREEMTKNQVSLTCLVKGFYPSDISVEWESNGQPENNYKTTPPMLDSDGSFFL

YSKLTVDKSRWQQGNVFSCSVMHEALHNHYTQKSLSLSPGK

Human IgG3 constant region, Uniprot: P01860

SEQ ID NO. 40

ASTKGPSVFPLAPCSRSTSGGTAALGCLVKDYFPEPVTVSWNSGALTSGVHTFPAVL

QSSGLYSLSSVVTVPSSSLGTQTYTCNVNHKPSNTKVDKRVELKTPLGDTTHTCPRC

PEPKSCDTPPPCPRCPEPKSCDTPPPCPRCPEPKSCDTPPPCPRCPAPELLGGPSVFLFPP

KPKDTLMISRTPEVTCVVVDVSHEDPEVQFKWYVDGVEVHNAKTKPREEQYNSTFR

VVSVLTVLHQDWLNGKEYKCKVSNKALPAPIEKTISKTKGQPREPQVYTLPPSREEM

TKNQVSLTCLVKGFYPSDIAVEWESSGQPENNYNTTPPMLDSDGSFFLYSKLTVDKS

RWQQGNIFSCSVMHEALHNRFTQKSLSLSPGK

Human IgM constant region, Uniprot: P01871

SEQ ID NO. 41

GSASAPTLFPLVSCENSPSDTSSVAVGCLAQDFLPDSITLSWKYKNNSDISSTRGFPSV

LRGGKYAATSQVLLPSKDVMQGTDEHVVCKVQHPNGNKEKNVPLPVIAELPPKVSV

FVPPRDGFFGNPRKSKLICQATGFSPRQIQVSWLREGKQVGSGVTTDQVQAEAKESG

PTTYKVTSTLTIKESDWLGQSMFTCRVDHRGLTFQQNASSMCVPDQDTAIRVFAIPPS

FASIFLTKSTKLTCLVTDLTTYDSVTISWTRQNGEAVKTHTNISESHPNATFSAVGEAS

ICEDDWNSGERFTCTVTHTDLPSPLKQTISRPKGVALHRPDVYLLPPAREQLNLRESA

TITCLVTGFSPADVFVQWMQRGQPLSPEKYVTSAPMPEPQAPGRYFAHSILTVSEEE

WNTGETYTCVAHEALPNRVTERTVDKSTGKPTLYNVSLVMSDTAGTCY

-continued

```
Human IgG4 constant region, Uniprot: P01861
                                                      SEQ ID NO. 42
ASTKGPSVFPLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCPSCPAPEFLG

GPSVFLFPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGK

Human IgA1 constant region, Uniprot: P01876
                                                      SEQ ID NO. 43
ASPTSPKVFPLSLCSTQPDGNVVIACLVQGFFPQEPLSVTWSESGQGVTARNFPPSQD

ASGDLYTTSSQLTLPATQCLAGKSVTCHVKHYTNPSQDVTVPCPVPSTPPTPSPSTPP

TPSPSCCHPRLSLHRPALEDLLLGSEANLTCTLTGLRDASGVTFTWTPSSGKSAVQGP

PERDLCGCYSVSSVLPGCAEPWNHGKTFTCTAAYPESKTPLTATLSKSGNTFRPEVH

LLPPPSEELALNELVTLTCLARGFSPKDVLVRWLQGSQELPREKYLTWASRQEPSQG

TTTFAVTSILRVAAEDWKKGDTFSCMVGHEALPLAFTQKTIDRLAGKPTHVNVSVV

MAEVDGTCY

Human IgA2 constant region, Uniprot: P01877
                                                      SEQ ID NO. 44
ASPTSPKVFPLSLDSTPQDGNVVVACLVQGFFPQEPLSVTWSESGQNVTARNFPPSQD

ASGDLYTTSSQLTLPATQCPDGKSVTCHVKHYTNPSQDVTVPCPVPPPPPCCHPRLSL

HRPALEDLLLGSEANLTCTLTGLRDASGATFTWTPSSGKSAVQGPPERDLCGCYSVS

SVLPGCAQPWNHGETFTCTAAHPELKTPLTANITKSGNTFRPEVHLLPPPSEELALNE

LVTLTCLARGFSPKDVLVRWLQGSQELPREKYLTWASRQEPSQGTTTFAVTSILRVA

AEDWKKGDTFSCMVGHEALPLAFTQKTIDRMAGKPTHVNVSVVMAEVDGTCY

Human Ig kappa constant region, Uniprot: P01834
                                                      SEQ ID NO. 45
TVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC
```

In some aspects of the antibodies provided herein, the antibody contains structural modifications to facilitate rapid binding and cell uptake and/or slow release. In some aspects, the DNABII antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

The antibodies, fragments, and equivalents thereof can be combined with a carrier, e.g., a pharmaceutically acceptable carrier or other agents to provide a formulation for use and/or storage.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762 and 6,180,370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000: 1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al, which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Pat. Publication US 2006/0211088; PCT Publication WO 2007/059782; U.S. Pat. No. 5,831,012).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Ed segments ($V_H$-$C_H$1-VH-$C_H$1) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58:671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects disclosed herein, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677, 425) and amino acid mutations in the Fc hinge region to decrease die biological half-life of the antibody (U.S. Pat. No. 6,165,745).

Additionally, the antibodies disclosed herein may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell with altered glycosylation mechanism (Shields et al., 2002 J. Biol. Chem. 277:26733-26740; Umana et al., 1999 Nat. Biotech. 17:176-180).

The antibodies disclosed herein can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies disclosed herein (EP 0154316 and EP 0401384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0486525.

The antibodies or fragments thereof of the present disclosure may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}$I, $^{131}$I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al., 1984 Anal. Biochem. 142: 68-78); sulfhydral groups (Koyama 1994 Chem. Abstr. 120: 217262t) of amino acid residues and carbohydrate groups (Rodwell et al. 1986 PNAS USA 83: 2632-2636; Quadri et al. 1993 Nucl. Med. Biol. 20: 559-570).

Further, the antibodies or fragments thereof of the present disclosure may be conjugated to a therapeutic agent. Suitable therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabinc, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alphasarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrietocin, phenomycin, enomycin toxins and mixed toxins.

Additional suitable conjugated molecules include ribonuclease (RNase), DNase, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intra-molecularly or inter-molecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity. Suitable conjugated molecules may further include any protein that binds to DNA provided that it does not create or stabilize biofilm architecture; it is envisioned that at least a subset of such proteins may facilitate the kinetics of binding for the agents disclosed herein.

The functional nucleic acid molecules may act as effectors, inhibitors, modulators, and stimulators of a specific activity possessed by a target molecule, or the functional nucleic acid molecules may possess a de novo activity independent of any other molecules.

The therapeutic agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al. 1994 Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995)).

Techniques for conjugating therapeutic agents to antibodies are well known (Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates" 1982 Immunol. Rev. 62:119-58), The antibodies disclosed herein or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or non-covalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-I-carboxylate (sulfo-SMCC) (Karpovsky et al., 1984 J. Exp. Med. 160:1686; Liu et al., 1985 Proc. Natl. Acad. Sci. USA 82:8648). When the binding molecules are antibodies, they can be conjugated by sulfhydryl bonding of the C-terminus hinge regions of the two heavy chains.

The antibodies disclosed herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes disclosed herein. Those skilled in the art will know of other suitable carriers for binding monoclonal antibodies, or will be able to ascertain such, using routine experimentation.

Antibodies disclosed herein can be used to purify the polypeptides disclosed herein and to identify biological equivalent polypeptide and/or polynucleotides. They also can be used to identify agents that modify the function of the polypeptides disclosed herein. These antibodies include polyclonal antisera, monoclonal antibodies, and various reagents derived from these preparations that are familiar to those practiced in the art and described above.

Antibodies that neutralize the activities of proteins encoded by identified genes can also be used in vivo and in vitro to demonstrate function by adding such neutralizing antibodies into in vivo and in vitro test systems. They also are useful as pharmaceutical agents to modulate the activity of polypeptides disclosed herein.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

Further, in some embodiments, the antibodies disclosed herein may be used to visualize and/or detect biofilms. In such embodiments, the antibodies may be detectably labeled, e.g., with a radioisotope, an enzyme which generates a detectable product, a fluorescent protein, and the like or conjugated to other moieties, such as members of specific binding pairs, e.g., biotin (member of biotin-avidin specific binding pair), and the like. Detectably labeled antibodies may then be introduced to the sample suspected of being colonized by a biofilm and visualized and/or detected through microscopy or other methods known to detect the relevant label, e.g., spectroscopy, cytometry, or other common techniques. Conjugated antibodies or unlabeled antibodies may likewise be identified through known analytical methods targeting the conjugated moiety or antibody, respectively. For example, in some embodiments, a detectably labeled secondary antibody specific to the isotype of the antibodies disclosed herein may be used in the visualization and/or detection of a biofilm.

Kits

Kits containing the agents and instructions necessary to perform the in vitro and in vivo methods as described herein also are claimed. Accordingly, the invention provides kits for performing these methods which may include the modified high mobility group-box 1 domain disclosed herein as well as instructions for carrying out the methods of this invention such as collecting tissue and/or performing the screen and/or analyzing the results and/or administration of an effective amount thereof as defined herein. These can be used alone or in combination with other suitable antimicrobial agents.

In one embodiment, the present disclosure provides a kit comprising a polypeptide comprising a modified high mobility group-box 1 domain comprising one or more substitutions selected from the group of C23S, C45S, and C106S and instructions for use in breaking down a biofilm or inhibiting, preventing or treating a microbial infection that produces a biofilm. Examples of modified high mobility group-box 1 domains comprising one or more substitutions selected from the group of C23S, C45S, and C106S are described above. In some embodiments, the modified high mobility group-box 1 domain comprises the substitution C45S. In some embodiments, the modified high mobility group-box 1 domain comprises the substitutions C23S, C45S, and C106S. In one embodiment, the kit further comprises one or more of an adjuvant, an antigenic peptide or an antimicrobial. In yet another embodiment, the kit further comprises a carrier selected from the group of a liquid carrier, a pharmaceutically acceptable carrier, a solid phase carrier, a pharmaceutically acceptable carrier, an implant, a stent, a paste, a gel, a dental implant or a medical implant.

It is appreciated that among the equivalents to a modified high mobility group-box 1 domain are modified high mobility group-box 2, modified high mobility group-box 3, and modified high mobility group-box 4 comprising cysteine to serine substitutions at one or more amino acid positions corresponding to C23S, C45S, and C106S of a modified high mobility group box 1. For modified high mobility group-box 2 the corresponding cysteine residues are found at position 23, 45, and 106; for modified high mobility group-box 3 the corresponding cysteine residues are found at position 23, 45, and 104; and for modified high mobility group-box 4 the corresponding cysteine residues are found at position 45, 104, 164, and 178. Thus, Applicants believe the kit aspects disclosed with respect to a modified high mobility group-box 1 comprising one or more substitutions selected from the group of C23S, C45S, and C106S are equally applicable to the aforementioned high mobility group-box species with one or more cysteine to serine substitutions at the mentioned positions, e.g. a modified high mobility group-box 2 comprising one or more substitutions selected from the group of C23S, C45S, and C106S; a modified high mobility group-box 3 comprising one or more substitutions selected from the group of C23S, C45S, and C104S; and a modified high mobility group-box 4 comprising one or more substitutions selected from the group of C45S, C104S, C164S, and C178S.

The following example is intended to illustrate, but not limit the invention.

EXAMPLES

Example 1—mHMGB1 (C45S) Testing

Applicants added HMGB1 at 0.1, 1 and 5 µg/ml at seeding and at 24h to a biofilm formed by Uropathogenic *E. coli* UTI89. Observed a dose-dependent disruption of UPEC biofilms when added at seeding and at 24h. Based on this information, Applicants hereby disclose a method for inhibiting, competing or titrating the binding of a deoxyribonucleic acid B II (DNABII) polypeptide to a microbial DNA in a biofilm, comprising, or alternatively consisting essentially of, or yet further consisting of, contacting the microbial DNA in the biofilm with an effective amount of an isolated or recombinant polypeptide comprising a modified high mobility group-box 1 domain (mHMGB1) comprising a C45S substitution thereby inhibiting, competing or titrating the binding of the DNABII polypeptide to the microbial DNA. The contacting can be accomplished in vitro or in vivo. Non-limiting examples of organisms that promote our cause the biofilm include one or more of *Burkholderia cenocepacia*, *Enterobacter* spp., *Staphylococcus aureus*, *Klebsiella pneumoniae*, *Acinetobacter baumanii*, *Pseudomonas aeruginosa*, *Enterococcus faecium*, Uropathogenic *Escherichia coli* (UPEC), Non-typeable *Haemophilus influenzae* (NTHI), and/or *Aggregatibacter actinomycetemcomitans*.

Figure 1B:
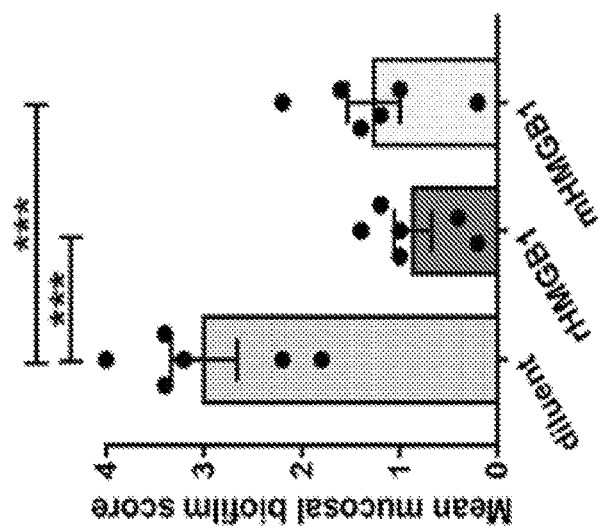
Figure 2A:
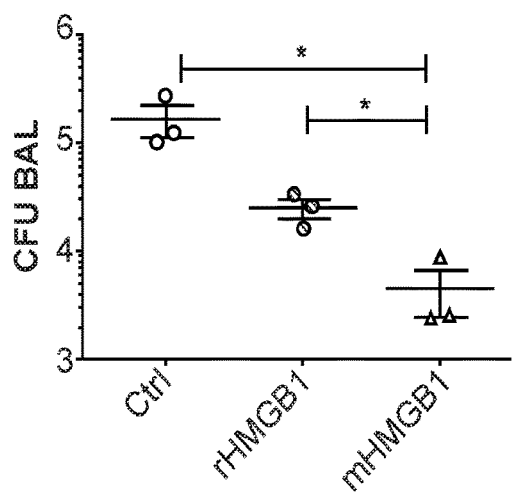
FIGS. 2A-2D show that mHMGB1 (C45S) promotes bacterial clearance and does not increase the inflammatory response in airways of mice infected with B. cenocepacia. C57BL/6 mice were infected with $10^7$ CFU i.t., and simultaneously received rHMGB1 or mHMGB1 (C45S). After 18 h, (FIG. 2A) B. cenocepacia CFUs were quantified in BAL, (FIG. 2B) total host cells infiltrating into the lung were enumerated in BAL, and (FIG. 2C) BAL cells were stained with anti CD45, CD11b and Ly-6G to measure neutrophil migration. Bars represent standard deviation. *$P<0.05$; **$P<0.005$.
Figure 2B:
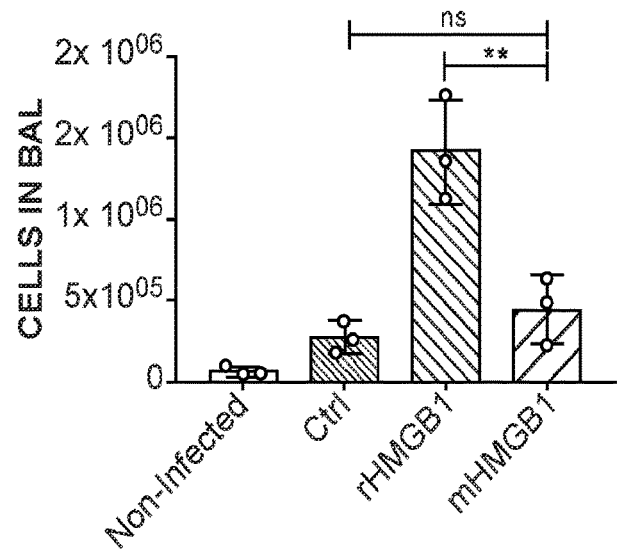
Figure 2C:
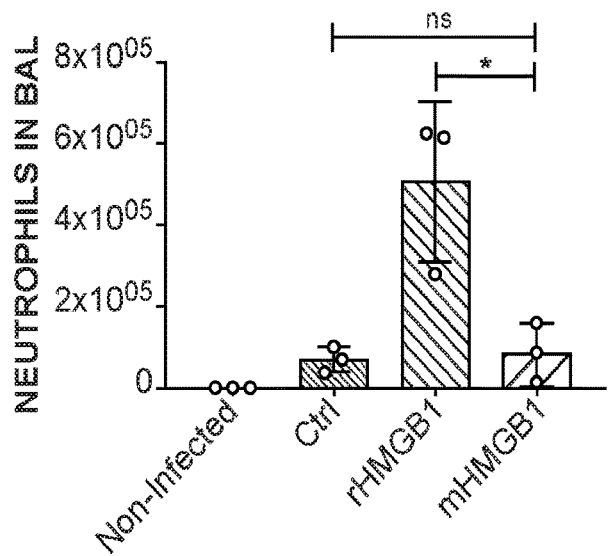
Figure 2D:
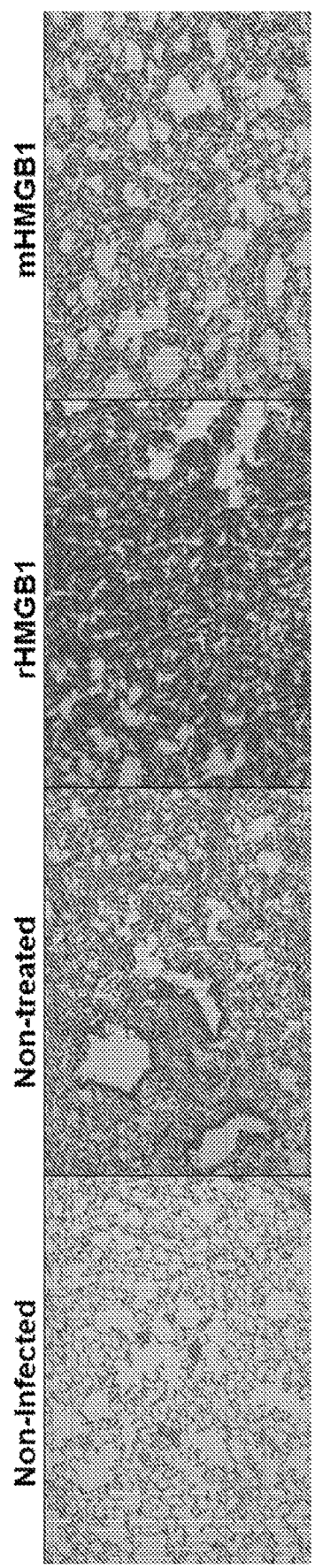
Figure 3:
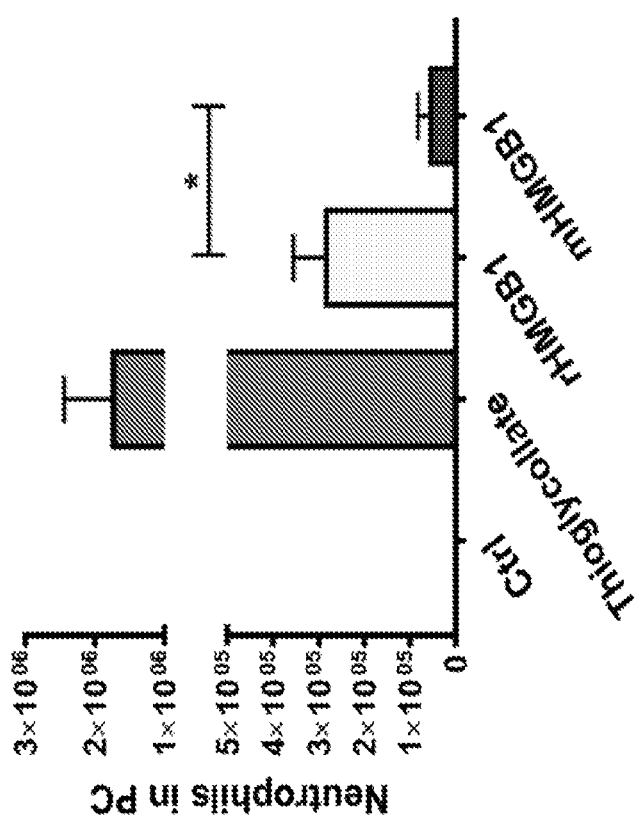
FIG. 3 shows that mHMGB1 (C45 S) does not promote neutrophil migration in the peritoneal cavity. C57BL/6 mice were injected with 4% thioglycollate, rHMGB1, or mHMGB1 (C45S) in the peritoneum. Cells within the peritoneal exudate were stained with anti CD45, CD11b and Ly-6G to determine the total number of neutrophils in the peritoneal cavity (PC). Bars represent SEM. *$P<0.05$. Note that mHMGB1 (C45S) lacks the inflammatory activities of rHMGB1.
Figures 4A, 4C:
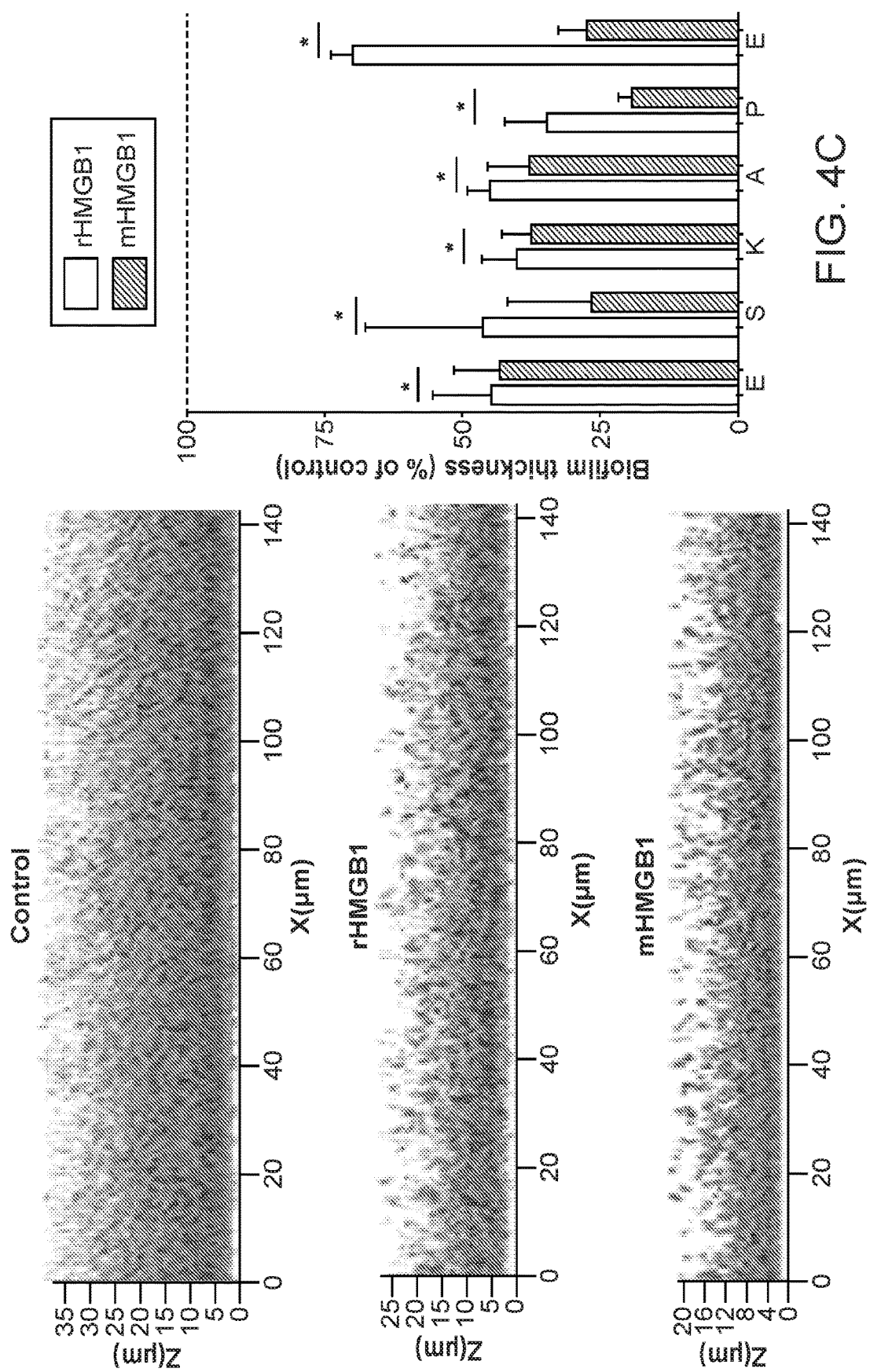
FIG. 4 shows the anti-biofilm effect of HMGB1 variants on bacterial pathogens. Indicated HMGB1 isoforms (200 nM) were added at 24 h to the respective in vitro preformed bacterial biofilm. After 16 h of incubation, biofilms were stained with LIVE/DEAD®, then visualized via CLSM. Images were analyzed by Comstat to calculate average thickness and biomass. Representative images for UPEC are shown in (FIG. 4A). Percent change in average thickness compared to control is shown in (FIG. 4B) and (FIG. 4C). 800 nM rHMGB1 and 200 nM mHMGB1 (C45S) was used for S. aureus (ESKAPE) biofilm treatment. 800 nM rHMGB1 and mHMGB1 (C45 S) was used for treatment of E. faecium (ESKAPE) biofilms, which were incubated with the respective protein for 1 h as opposed to 16 h. Biomass (not shown) showed identical trends. Bars represent the SEM. Statistical significance compared to control was assessed with unpaired t-tests, *$P<0.05$. HMGB1 and its variant were able to significantly disrupt established biofilms.
Figure 5:
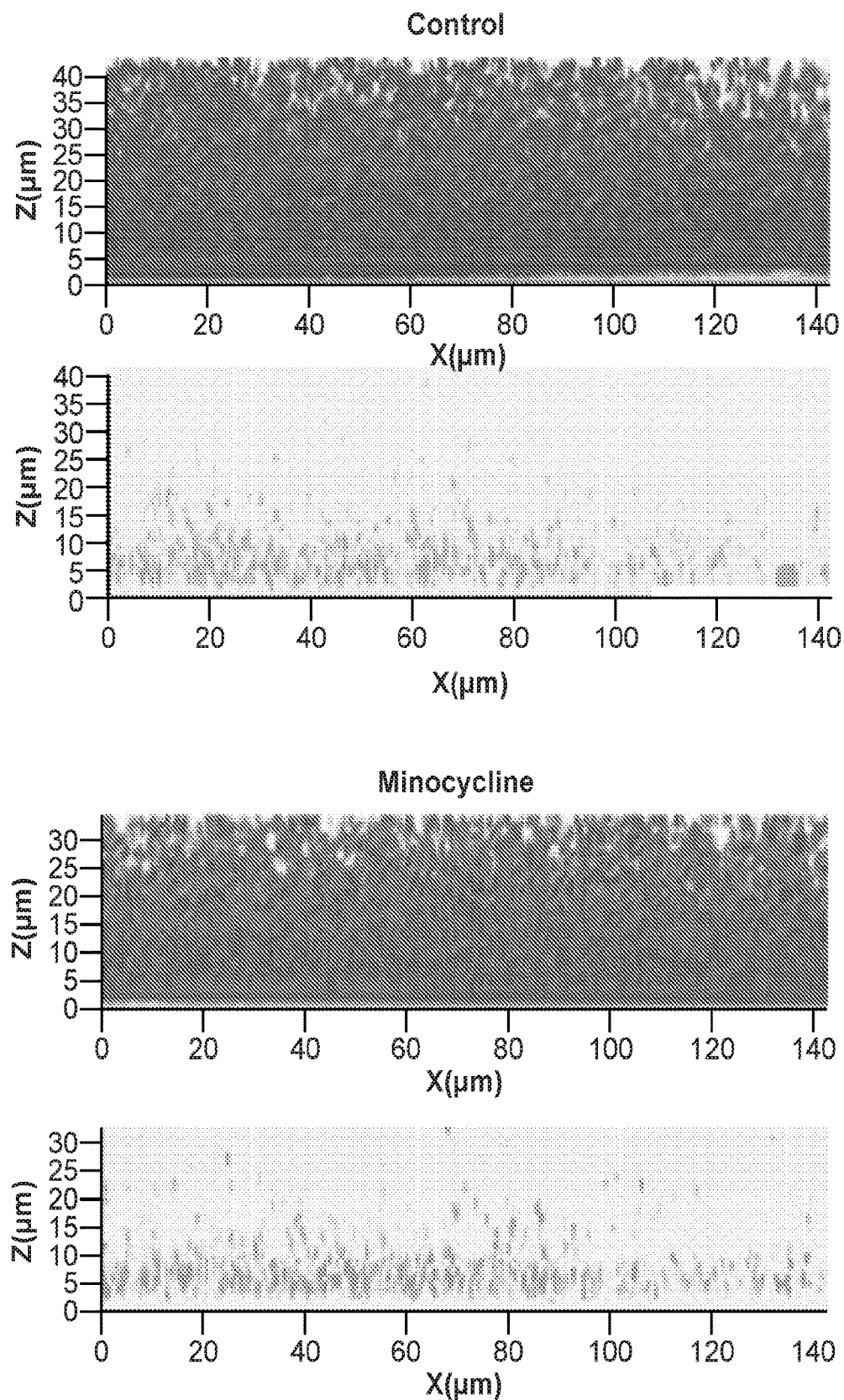
FIG. 5 shows that mHMGB1 (C45 S) potentiates antibiotic-mediated killing. B. cenocepacia biofilms were pre-formed for 24 h and then incubated with minocycline (1 mg/ml), mHMGB1 (C45S) (200 nM), or mHMGB1 (C45S) (200 nM)+minocycline (1 mg/ml) for 16 h. Biofilms were stained with LIVE/DEAD® and imaged via CLSM. Live cells are indicated in the upper half of each image and dead cells in the lower half of each image. Note the increase in dead cells only in the presence of both mHMGB1 (C45S) and minocycline.
Figure 5:
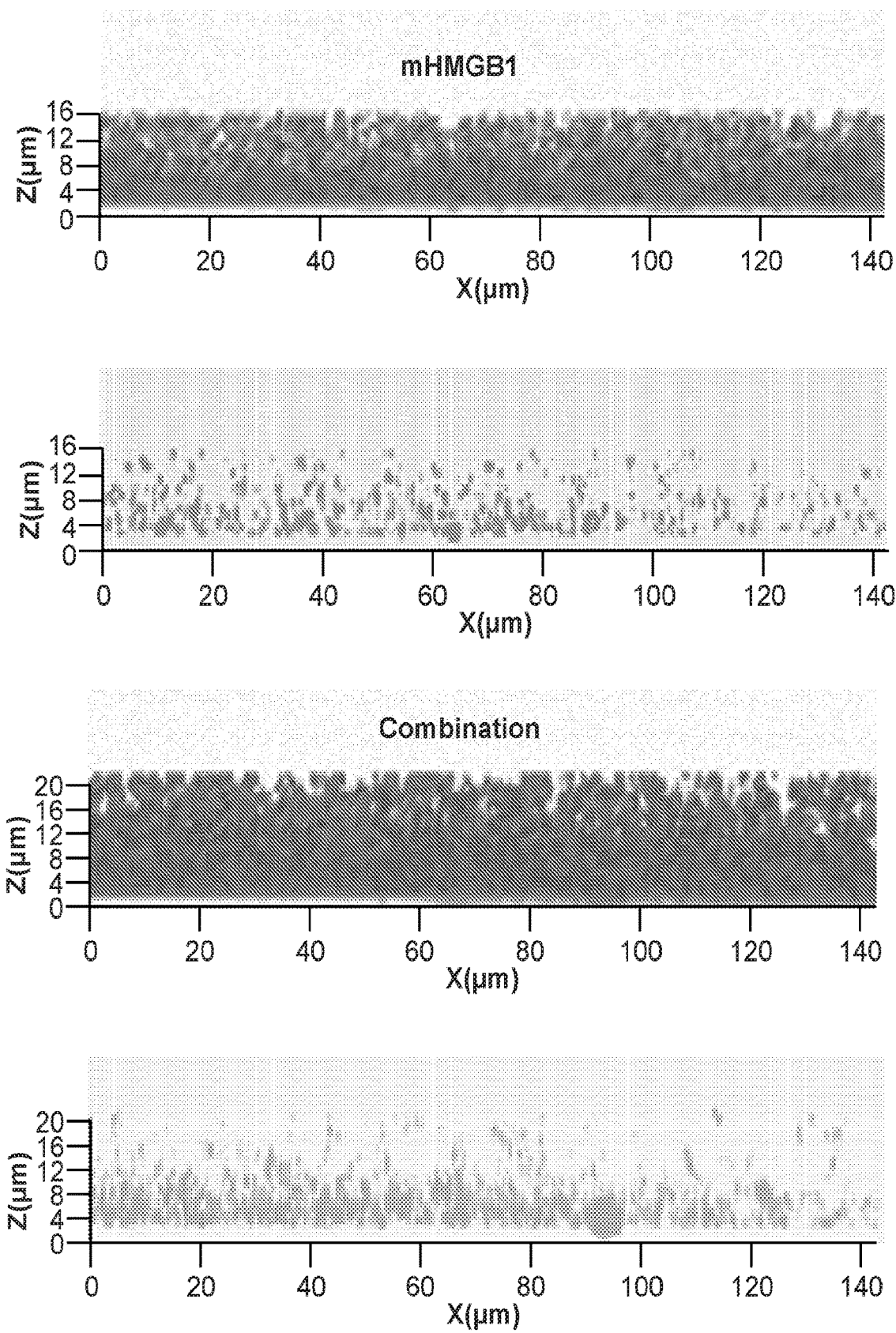
Figure 6B:
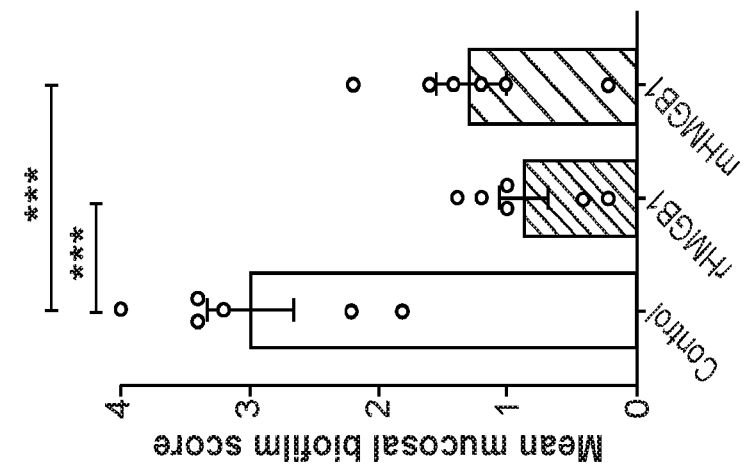
FIG. 6 shows that rHMGB1 and mHMGB1 (C45 S) promote biofilm resolution in an experimental OM animal model. Diluent or 5 μg rHMGB1 or mHMGB1 (C45 S) were delivered directly to middle ears of chinchillas at 4 and 5 days post infection with NTHI. Animals were sacrificed 24 h later, and their middle ears were imaged (FIG. 6A) and blindly scored (FIG. 6B) based on the criteria described in the bottom of (FIG. 6A). Bars represent SEM. ***$P<0.001$. Images and scoring demonstrate HMGB1 promoted clearance of pre-formed NTHI biofilms in vivo.
Figure 6A:
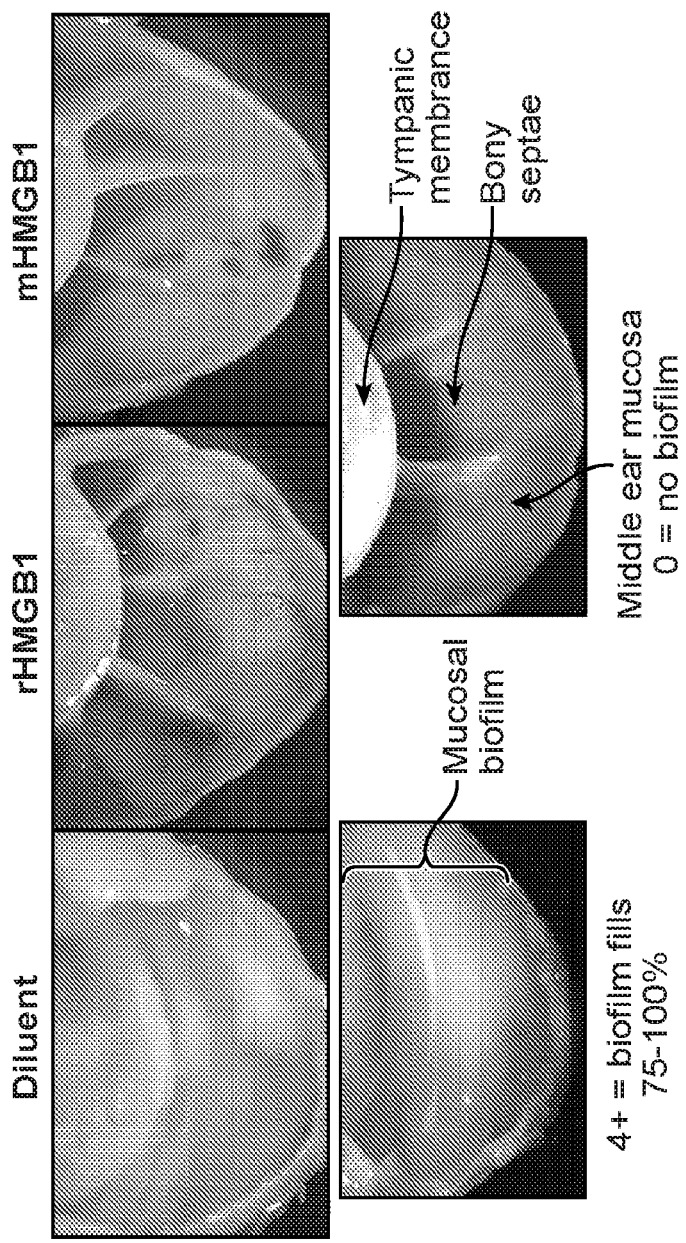

Preliminary Results mHMGB1 (C45S) Retains its Antibiofilm Function In Vitro Against Multiple Human Pathogens To determine the antibiofilm function of the variant HMGB1 (mHMGB1 (C45S)), Applicants expressed and purified human recombinant HMGB1 (rHMGB1) and recombinant variant HMGB1 (mHMGB1 (C45S)) in *E. coli*. In vitro preformed 24-hour biofilms formed by multiple human pathogens as indicated in Table 1 were incubated with 5 µg/ml rHMGB1 or mHMGB1 (C45S) for 16 hours. *Enterococcus faecium* biofilms were incubated with 20 µg/ml rHMGB1 or mHMGB1 (C45S) for 16 hours. Biofilms were washed and stained with LIVE/DEAD® stain and analyzed using a confocal laser scanning microscope and COMSTAT analysis. Applicants observed that mHMGB1 (C45S) was effective at disrupting each of the in vitro preformed biofilms as indicated by significant reduction in average thickness and biomass compared to the control (Table 1). As indicated in Table 1, the antibiofilm activity of mHMGB1 (C45S) was also comparable to that of rHMGB1. These data suggested that substitution of cysteine with serine at position 45 does not alter the antibiofilm activity of human recombinant HMGB1.

mHMGB1 (C45S) Retains its Antibiofilm Function In Vivo in Two Distinct Animal Models but the Inflammatory Response is Significantly Attenuated To determine the antibiofilm function of mHMGB1 (C45S) in vivo, Applicants employed two distinct animal models. In the first model Applicants tested the ability of rHMGB1 and mHMGB1 (C45S) to clear preformed NTHI biofilms in Applicants' well-established chinchilla model of experimental OM (Novotny et al. 2011; 2013b; Novotny et al. 2016). Applicants first established NTHI strain 86-028NP biofilms in the chinchilla middle ear for 4 days. Applicants then treated the 4-day old NTHI biofilm with two doses (day 4 and 5; 5 µg each) of rHMGB1, mHMGB1 (C45S) or diluent. On day 6 the animals were sacrificed and the middle ears were blindly scored for the presence of any remaining biofilm. Animals treated with diluent exhibited a thick mucosal biofilm in the middle ears (FIGS. 1A-1B). Strikingly, rHMGB1 and mHMGB1 (C45S) were very effective at clearing the biofilms from the middle ear as indicated by the visible bony septae (FIGS. 1A-1B). In the second model, Applicants tested the ability of rHMGB1 and mHMGB1 (C45S) to inhibit biofilm development of *Burkholderia cenocepacia* in the murine airways. C57BL/6 mice were infected with $10^7$ CFU of *B. cenocepacia* intratracheally and 5 µg of rHMGB1 or mHMGB1 (C45S) was added simultaneously. After 18 hours, the animals were sacrificed and bronchoalveolar lavage (BAL) and lungs were collected. CFUs (FIG. 2A), total inflammatory infiltrate (FIG. 2B), and total infiltrated neutrophils (FIG. 2C) were enumerated in BAL. rHMGB1 and mHMGB1 (C45S) were effective at reducing the bacterial burden in BAL as compared to the control (FIG. 2A). While rHMGB1 mounted a robust inflammatory response as evident from the increase in total inflammatory infiltrate and neutrophils, mHMGB1 (C45S) exhibited a significantly attenuated inflammatory response (FIGS. 2B, 2C). Applicants also evaluated lung damage at 72 hours post infection and treatment and observed that while lungs treated with rHMGB1 displayed severe inflammation and increased neutrophil response, lungs treated with mHMGB1 (C45S) more resembled uninfected mouse lungs (FIG. 2D). Lastly, Applicants validated the inflammatory activity of rHMGB1 and mHMGB1 (C45S) in an in vivo chemotaxis model to determine the ability to recruit neutrophils (Orlova et al. 2007; Penzo et al. 2010). C57BL/6 mice were injected with 5 µg of either mHMGB1 (C45S) or rHMGB1 or 1 ml of 4% thioglycollate. After 4h, mice were sacrificed and total neutrophils were quantified in peritoneal lavage. As evident in FIG. 3, whereas rHMGB1 induced neutrophil recruitment to the peritoneal cavity, mHMGB1 (C45S) failed to recruit neutrophils. Collectively, these results demonstrated that mHMGB1 (C45S) facilitated clearance of bacteria without the undesirable pro-inflammatory activity of rHMGB1.

TABLE 1

Anti-biofilm effect of rHMGB1 and mHMGB1 (C45S) on multiple bacterial pathogens.

| Organism | rHMGB1 | | mHMGB1 (C45S) | |
|---|---|---|---|---|
| | AT | BM | AT | BM |
| *Burkholderia cenocepacia* | ↓↓↓ | ↓↓↓ | ↓↓↓ | ↓↓↓ |
| *\*Enterobacter* spp. | ↓↓↓ | ↓↓↓ | ↓↓↓ | ↓↓↓ |
| *\*Staphylococcus aureus* | ↔ | ↔ | ↓↓↓ | ↓↓↓ |
| *\*Klebsiella pneumoniae* | ↓↓↓ | ↓↓↓ | ↓↓↓ | ↓↓↓ |
| *\*Acinetobacter baumanii* | ↓↓↓ | ↓↓ | ↓↓↓ | ↓↓↓ |
| *\*Pseudomonas aeruginosa* | ↓↓↓ | ↓↓↓ | ↓↓↓ | ↓↓↓ |
| *\*Enterococcus faecium*[b] | ↓↓↓ | ↓↓↓ | ↓↓ | ↓↓ |
| Uropathogenic *E. coli* | ↓↓ | ↓↓ | ↓↓↓ | ↓↓↓ |
| Nontypeable *Haemophilus influenzae* | ↓ | ↓ | ↓ | ↓ |
| *Aggregatibacter actinomycetemcomitans* | ↓ | ↓ | ↓ | ↓ |

*Members of the ESKAPE pathogens
↓: 20-30% decrease;
↓↓: 31-50% decrease;
↓↓↓: >51% decrease;
↔: No change
[a] All values indicated with arrows had p-values < 0.05
[b] 20 µg/ml rHMGB1 and mHMGB1 (C45S) was used for biofilm treatment.

HMGB1 isoforms (5 µg/ml) were added at 24h to in vitro preformed bacterial biofilms. After 16 h of incubation (40h total), biofilms were washed and stained with LIVE/DEAD® followed by visualization using CLSM. Biofilms were analyzed by Comstat to calculate average thickness[a] (AT) and biomass[a] (BM).

Further experiments were carried out confirming the effects of mHMGB1 (C45S) (FIG. 4-7).

Example 2—Triple-Mutant HMGB1 (C23S, C45S, and C106S) and Other Variants

Applicants generate a triple-mutant HMGB1 comprising C23S, C45S, and C106S substitutions and other variants, such as but not limited to HMGB1 variants comprising C23 S alone, C23S and C45S, C23S and C106S, C45S and C106S, and C106S alone. These modified high mobility group-box 1 domains are tested for efficacy according to the same methods as Example 1. Parallel runs are performed for the HMGB2, HMGB3, and HMGB4 variants disclosed herein, i.e. the single, double, triple, and quadruple mutants for which sequences are provided herein above.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

REFERENCES

Abraham, E., Arcaroli, J., Carmody, A., Wang, H., and Tracey, K. J. (2000) HMG-1 as a mediator of acute lung inflammation. *J Immunol* 165: 2950-4.

Agnello, D., Wang, H., Yang, H., Tracey, K. J., and Ghezzi, P. (2002) HMGB-1, a DNA-binding protein with cytokine activity, induces brain TNF and IL-6 production, and mediates anorexia and taste aversion. *Cytokine* 18: 231-6.

Brandstetter, K. A., Jurcisek, J. A., Goodman, S. D., Bakaletz, L. O., and Das, S. (2013) Antibodies directed against integration host factor mediate biofilm clearance from Nasopore. *Laryngoscope* 123: 2626-32.

Brockson, M. E. et al. (2014) Evaluation of the kinetics and mechanism of action of anti-integration host factor mediated disruption of bacterial biofilms. *Mol Microbiol.*

Davalos, A. R. et al. (2013) p53-dependent release of Alarmin HMGB1 is a central mediator of senescent phenotypes. *J Cell Biol* 201: 613-29.

Devaraj, A., Justice, S. S., Bakaletz, L. O., and Goodman, S. D. (2015) DNABII proteins play a central role in UPEC biofilm structure. *Mol Microbiol.*

Freire, M. O. et al. (2016) A Bacterial Biofilm Induced Oral Osteolytic Infection Can be Successfully Treated by Immuno-Targeting an Extracellular Nucleoid Associated Protein. *Mol Oral Microbiol.*

Gong, W., Li, Y., Chao, F., Huang, G., and He, F. (2009) Amino acid residues 201-205 in C-terminal acidic tail region plays a crucial role in antibacterial activity of HMGB1. *J Biomed Sci* 16: 83.

Goodman, S. D. et al. (2011) Biofilms can be dispersed by focusing the immune system on a common family of bacterial nucleoid-associated proteins. *Mucosal Immunol* 4: 625-37.

Goodwin, G. H., Sanders, C., and Johns, E. W. (1973) A new group of chromatin-associated proteins with a high content of acidic and basic amino acids. *Eur J Biochem* 38: 14-9.

Gustave, J. E., Jurcisek, J. A., McCoy, K. S., Goodman, S. D., and Bakaletz, L. O. (2013) Targeting bacterial integration host factor to disrupt biofilms associated with cystic fibrosis. *J Cyst Fibros* 12: 384-9.

Idicula, W. A. et al. (2016) Identification of biofilms in post-tympanostomy tube otorrhea. *Laryngoscope In Press.*

Justice, S. S. et al. (2012) Aberrant community architecture and attenuated persistence of uropathogenic *Escherichia coli* in the absence of individual IHF subunits. *PLoS One* 7: e48349.

Kang, R. et al. (2014) HMGB1 in health and disease. *Mol Aspects Med* 40: 1-116.

Kazama, H., Ricci, J. E., Herndon, J. M., Hoppe, G., Green, D. R., and Ferguson, T. A. (2008) Induction of immunological tolerance by apoptotic cells requires caspase-dependent oxidation of high-mobility group box-1 protein. *Immunity* 29: 21-32.

Lee, H. et al. (2010) Analysis of nuclear high mobility group box 1 (HMGB1)-binding proteins in colon cancer cells: clustering with proteins involved in secretion and extranuclear function. *J Proteome Res* 9: 4661-70.

Mardente, S. et al. (2012) HMGB1 induces the overexpression of miR-222 and miR-221 and increases growth and motility in papillary thyroid cancer cells. *Oncol Rep* 28: 2285-9.

Melloni, E., Sparatore, B., Patrone, M., Pessino, A., Passalacqua, M., and Pontremoli, S. (1995a) Extracellular release of the 'differentiation enhancing factor', a HMG1 protein type, is an early step in murine erythroleukemia cell differentiation. *FEBS Lett* 368: 466-70.

Melloni, E., Sparatore, B., Patrone, M., Pessino, A., Passalacqua, M., and Pontremoli, S. (1995b) Identity in molecular structure between "differentiation enhancing factor" of murine erythroleukemia cells and the 30 kD heparin-binding protein of developing rat brain. *Biochem Biophys Res Commun* 210: 82-9.

Novotny, L. A., Amer, A. O., Brockson, M. E., Goodman, S. D., and Bakaletz, L. O. (2013a) Structural stability of *Burkholderia cenocepacia* biofilms is reliant on eDNA structure and presence of a bacterial nucleic acid binding protein. *PLoS One* 8: e67629.

Novotny, L. A., Clements, J. D., and Bakaletz, L. O. (2011) Transcutaneous immunization as preventative and therapeutic regimens to protect against experimental otitis media due to nontypeable *Haemophilus influenzae*. *Mucosal Immunol* 4: 456-67.

Novotny, L. A., Clements, J. D., and Bakaletz, L. O. (2013b) Kinetic analysis and evaluation of the mechanisms involved in the resolution of experimental nontypeable *Haemophilus influenzae*-induced otitis media after transcutaneous immunization. *Vaccine* 31: 3417-26.

Novotny, L. A., Jurcisek, J. A., Goodman, S. D., and Bakaletz, L. O. (2016) Monoclonal antibodies against DNA-binding tips of DNABII proteins disrupt biofilms in vitro and induce bacterial clearance in vivo. *EBioMedicine* 10: 33-44.

Orlova, V. V. et al. (2007) A novel pathway of HMGB1-mediated inflammatory cell recruitment that requires Mac-1-integrin. *EMBO J* 26: 1129-39.

Paull, T. T., Haykinson, M. J., and Johnson, R. C. (1993) The nonspecific DNA-binding and -bending proteins HMG1 and HMG2 promote the assembly of complex nucleoprotein structures. *Genes Dev* 7: 1521-34.

Penzo, M. et al. (2010) Inhibitor of NF-kappa B kinases alpha and beta are both essential for high mobility group box 1-mediated chemotaxis [corrected]. *J Immunol* 184: 4497-509.

Pistoia, V. and Raffaghello, L. (2011) Damage-associated molecular patterns (DAMPs) and mesenchymal stem cells: a matter of attraction and excitement. *Eur J Immunol* 41: 1828-31.

Ranzato, E., Patrone, M., Pedrazzi, M., and Burlando, B. (2009) HMGb1 promotes scratch wound closure of HaCaT keratinocytes via ERK1/2 activation. *Mol Cell Biochem* 332: 199-205.

Rocco, C. J., Davey, M. E., Bakaletz, L. O., and Goodman, S. D. (2016) Natural antigenic differences in the functionally equivalent extracellular DNABII proteins of bacterial biofilms provide a means for targeted biofilm therapeutics. *Mol Oral Microbiol.*

Segall, A. M., Goodman, S. D., and Nash, H. A. (1994) Architectural elements in nucleoprotein complexes: interchangeability of specific and non-specific DNA binding proteins. *EMBO J* 13: 4536-48.

Tang, D., Kang, R., Livesey, K. M., Zeh, H. J., 3rd, and Lotze, M. T. (2011) High mobility group box 1 (HMGB1) activates an autophagic response to oxidative stress. *Antioxid Redox Signal* 15: 2185-95.

Wang, H. et al. (1999) HMG-1 as a late mediator of endotoxin lethality in mice. *Science* 285: 248-51.

Yang, D., Chen, Q., Yang, H., Tracey, K. J., Bustin, M., and Oppenheim, J. J. (2007) High mobility group box-1 protein induces the migration and activation of human dendritic cells and acts as an alarmin. *J Leukoc Biol* 81: 59-66.

Yang, H. et al. (2012) Redox modification of cysteine residues regulates the cytokine activity of high mobility group box-1 (HMGB1). *Mol Med* 18: 250-9.

Zetterstrom, C. K., Strand, M. L., and Soder, O. (2006) The high mobility group box chromosomal protein 1 is expressed in the human and rat testis where it may function as an antibacterial factor. *Hum Reprod* 21: 2801-9.

---

What is claimed is:

1. A method for inhibiting, competing or titrating the binding of a deoxyribonucleic acid B II (DNABII) polypeptide to a microbial DNA in a biofilm, comprising contacting the microbial DNA in the biofilm with an effective amount of an isolated or recombinant polypeptide comprising a modified high mobility group-box 1 domain comprising C45S thereby inhibiting, competing or titrating the binding of the DNABII polypeptide to the microbial DNA.

2. The method of claim 1, wherein the modified high mobility group-box 1 domain further comprises the substitutions C23S or C106S.

3. The method of claim 1, wherein the contacting is in vitro or in vivo.

4. The method of claim 1, wherein the biofilm is formed by *Burkholderia cenocepacia, Enterobacter* spp., *Staphylococcus aureus, Klebsiella pneumoniae, Acinetobacter baumanii, Pseudomonas aeruginosa, Enterococcus faecium,*

Uropathogenic *Escherichia coli* (UPEC), Non-typeable *Haemophilus influenzae* (NTHI), or *Aggregatibacter actinomycetemcomitans*.

5. The method of claim 1, wherein the contacting is in vivo in a subject and the method further comprises administering to the subject an effective amount of an antibiotic.

6. The method of claim 5, wherein the subject is suffering from sepsis.

\* \* \* \* \*